United States Patent
Inui et al.

(10) Patent No.: US 10,961,526 B2
(45) Date of Patent: Mar. 30, 2021

(54) TRANSFORMANT, AND METHOD FOR PRODUCING PROTOCATECHUIC ACID OR SALT THEREOF USING SAME

(71) Applicants: RESEARCH INSTITUTE OF INNOVATIVE TECHNOLOGY FOR THE EARTH, Kyoto (JP); SUMITOMO BAKELITE CO., LTD., Tokyo (JP)

(72) Inventors: Masayuki Inui, Kyoto (JP); Kazumi Hiraga, Kyoto (JP); Masako Suda, Kyoto (JP); Takahisa Kogure, Kyoto (JP)

(73) Assignees: RESEARCH INSTITUTE OF INNOVATIVE TECHNOLOGY FOR THE EARTH, Kyoto (JP); SUMITOMO BAKELITE CO., LTD., Tokyo (JP)

(*) Notice: Subject to any disclaimer, the term of this patent is extended or adjusted under 35 U.S.C. 154(b) by 56 days.

(21) Appl. No.: 16/089,567

(22) PCT Filed: Feb. 24, 2017

(86) PCT No.: PCT/JP2017/007233
§ 371 (c)(1),
(2) Date: Sep. 28, 2018

(87) PCT Pub. No.: WO2017/169399
PCT Pub. Date: Oct. 5, 2017

(65) Prior Publication Data
US 2019/0119664 A1    Apr. 25, 2019

(30) Foreign Application Priority Data

Mar. 28, 2016   (JP) ................. 2016-064516

(51) Int. Cl.
| | | |
|---|---|---|
| *C12P 7/42* | (2006.01) | |
| *C12N 9/88* | (2006.01) | |
| *C12N 15/09* | (2006.01) | |
| *C12N 1/00* | (2006.01) | |
| *C12N 9/02* | (2006.01) | |
| *C12R 1/15* | (2006.01) | |

(52) U.S. Cl.
CPC ............... *C12N 9/88* (2013.01); *C12N 1/00* (2013.01); *C12N 9/0073* (2013.01); *C12N 15/09* (2013.01); *C12P 7/42* (2013.01); *C12R 1/15* (2013.01); *C12Y 114/13064* (2013.01); *C12Y 401/0304* (2013.01); *C12Y 402/01118* (2013.01)

(58) Field of Classification Search
None
See application file for complete search history.

(56) References Cited

U.S. PATENT DOCUMENTS

| | | |
|---|---|---|
| 4,500,640 A | 2/1985 | Katsumata et al. |
| 5,272,073 A | 12/1993 | Frost et al. |
| 5,487,987 A | 1/1996 | Frost et al. |
| 5,616,480 A | 4/1997 | Sugimoto et al. |
| 5,616,496 A | 4/1997 | Frost et al. |
| 5,629,181 A | 5/1997 | Frost et al. |
| 6,303,383 B1 | 10/2001 | Nakamura et al. |
| 6,472,190 B1 | 10/2002 | Frost |
| 2007/0087423 A1 | 4/2007 | Murakami et al. |
| 2013/0203139 A1 | 8/2013 | Yukawa et al. |
| 2014/0018511 A1 | 1/2014 | Yunomura et al. |
| 2015/0197775 A1 | 7/2015 | Iida et al. |
| 2017/0073658 A1 | 3/2017 | Yukawa et al. |
| 2018/0044688 A1 | 2/2018 | Inui et al. |

FOREIGN PATENT DOCUMENTS

| | | |
|---|---|---|
| EP | 0 077 548 | 4/1983 |
| EP | 2 957 635 | 12/2015 |
| JP | 57-183799 | 11/1982 |
| JP | 58-67699 | 4/1983 |
| JP | 62-166890 | 7/1987 |
| JP | 05-007491 | 1/1993 |
| JP | 2006-124440 | 5/2006 |
| JP | 2009-065839 | 4/2009 |
| JP | 2009-082064 | 4/2009 |
| JP | 2010-207094 | 9/2010 |
| WO | 2005/010182 | 2/2005 |

(Continued)

OTHER PUBLICATIONS

Gross et al. (JBC, 1955, pp. 781-788).*

(Continued)

*Primary Examiner* — Hope A Robinson
(74) *Attorney, Agent, or Firm* — Wenderoth, Lind & Ponack, L.L.P.

(57) ABSTRACT

Provided is a microorganism that is able to efficiently produce protocatechuic acid or a salt thereof by using a saccharide as a raw material, and a method of efficiently producing protocatechuic acid or a salt thereof by using the microorganism. Provided is a transformant having protocatechuic acid producing ability, subjected to modifications of enhancement of 3-dehydroshikimate dehydratase activity; enhancement of chorismate pyruvate lyase activity; and enhancement of 4-hydroxybenzoate hydroxylase activity. Also provided is a method of producing protocatechuic acid or a salt thereof, including the step of culturing the transformant in a reaction solution containing a saccharide so as to cause the transformant to produce protocatechuic acid or a salt thereof.

17 Claims, 3 Drawing Sheets

Specification includes a Sequence Listing.

(56) References Cited

FOREIGN PATENT DOCUMENTS

| WO | 2012/033112 | 3/2012 |
|---|---|---|
| WO | 2012/128231 | 9/2012 |
| WO | 2014/007273 | 1/2014 |
| WO | 2015/124687 | 8/2015 |
| WO | 2015/174446 | 11/2015 |
| WO | 2016/027870 | 2/2016 |
| WO | 2016/036915 | 3/2016 |

OTHER PUBLICATIONS

Okai et al. (Appl. Microbiol. Biotechnol., 2016, pp. 135-145).*
Liebl et al., "Transfer of Brevibacterium divaricatum DSM 20297$^T$, "Brevibacterium flavum" DSM 20411, "Brevibacterium lactofermentum" DSM 20412 and DSM 1412, and Corynebacterium lilium DSM 20137$^T$ to Corynebacterium glutamicum and Their Distinction by rRNA Gene Restriction Patterns", International Journal of Systematic Bacteriology, 1991, vol. 41, No. 2, pp. 255-260.
Komagata et al., Amino Acid and Nucleic Acid No. 56, vol. 45, No. 10, pp. 944-963 (1987).
Nichols et al., "Clotting and Sequencing of *Escherichia coli* ubiC and Purification of Chorismate Lyase", Journal of Bacteriology, 1992, vol. 174, No. 16, pp. 5309-5316.
Sugimoto et al., "Regulation of Enzymes for Erythrose 4-Phosphate Synthesis in Brevibacterium flavum", Agric. Biol. Chem., 1989, vol. 53, No. 8, pp. 2081-2087.
Sprenger et al., "Transaldolase B of *Escherichia coli* K-12: Cloning of Its Gene, talB, and Characterization of the Enzyme from Recombinant Strains", Journal of Bacteriology, 1995, vol. 177, No. 20, pp. 5930-5936.
Mehdi, S. et al., "Dehydroquinate Synthase from *Escherichia coli*, and Its Substrate 3-Deoxy-D-arabino-heptulosonic acid 7-phosphate.", Methods in Enzymology, 1987, vol. 142, pp. 306-314.
Chaudhuri et al., "3-Dehydroquinate dehydratase from *Escherichia coli*", Methods in Enzymology, 1987, vol. 142, pp. 320-314.
Chaudhuri et al., "Shikimate Dehydratase from *Escherichia coli*", Methods in Enzymology, 1987, vol. 142, pp. 315-320.
Cheng et al., "Structures of Helicobacter *pylori* Shikimate Kinase Reveal a Selective Inhibitor-Induced-Fit Mechanism.", PLoS One, 2012, vol. 7, No. 3, e33481, pp. 1-11.
Kitzing et al., "Spectroscopic and Kinetic Characterization of the Bifunctional Chorismate Synthase from Neurospora crassa", Journal of Biological Chemistry, 2001, vol. 276 No. 46, pp. 42658-42666.
Ikeda et al., "Identification and application of a different glucose uptake system that functions as an alternative to the phosphotransferase system in Corynebacterium glutamicum", Appl. Microbiol. Biotechnol., 2011, vol. 90, pp. 1443-1451.
Lindner et al., "Phosphotransferase System-Independent Glucose Utilization in Corynebacterium glutamicum by Inositol Permeases and Glucokinases", Applied and Environmental Microbiology, 2011, vol. 77, No. 11, pp. 3571-3581.
Jojima et. al., "Identification of a HAD superfamily phosphatase, HdpA, involved in 1,3-dihydroxyacetone production during sugar catabolism in Corynebacterium glutamicum", FEBS Letters, 2012, vol. 586, pp. 4228-4232.

Gawronski et al., "Microtiter assay for glutamine synthetase biosynthetic activity using inorganic phosphate detection", Analytical Biochemistry, 2004, vol. 327, pp. 114-118.
Miwa et al., "Cryptic Plasmids in Glutamic Acid-producing Bacteria", Agric. Biol. Chem., 1984, vol. 48, No. 11, pp. 2901-2903.
Yamaguchi et al., "Determination of the complete nucleotide sequence of the Brevibacterium lactofermentum plasmid pAM330 and the analysis of its genetic information", Nucleic Acids Research, Symposium Series, 1985, vol. 16, pp. 265-267.
Kurusu et al., "Identification of Plasmid Partition Function in Coryneform Bacteria", Applied and Environmental Microbiology, 1991, vol. 57, No. 3, pp. 759-764.
Katsumata et al., "Partoplast Transformation of Glutamate-Producing Bacteria with Plasmid DNA", Journal of Bacteriology, 1984, vol. 159, No. 1, pp. 306-311.
Eikmanns et al.,"A family of Corynebacterium glutamicum/ *Escherichia coli* shuttle vectors for cloning, controlled gene expression, and promoter probing" Gene, 1991, vol. 102, pp. 93-98.
Kurusu et al., "Electroporation-transformation System for Coryneform Bacteria by Auxotrophic Complementation", Agric. Biol. Chem., 1990, vol. 54, No. 2, pp. 443-447.
Inui et al., "Metabolic Analysis of Corynebacterium glutamicum during Lactate and Succinate Productions under Oxygen Deprivation Conditions", Journal of Molecular Microbiology and Biotechnology, 2004, vol. 7, pp. 182-196.
Omumasaba et al., "Corynebacterium glutamicum Glyceraldehyde-3-Phosphate Dehydrogenase Isoforms with Opposite, ATP-Dependent Regulation" Journal of Molecular Microbiology and Biotechnology, 2004, vol. 8, pp. 91-103.
Pfennig et al., "The Dissimilatory Sulfate-Reducing Bacteria", In the Prokaryotes. A Handbook on Habitats Isolation and Identification of Bacteria, Ed. by Starr et al., 1981, Chapter 74, pp. 926-940.
Nougei Kagaku Jitsukensyo, 1990, vol. 3, No. 26, pp. 1188-1200.
Hasegawa et al., "Improvement of the Redox Balance Increases L-Valine Production by Corynebacterium glutamicum under Oxygen Deprivation Conditions", Applied and Environmental Microbiology, 2012, vol. 78, No. 3, pp. 865-875.
Suzuki et al., "Large-Scale Engineering of the Corynebacterium glutamicum Genome", Applied and Environmental Microbiology, 2005, vol. 71, No. 6, pp. 3369-3372.
Inui et al., "Metabolic Engineering of Corynebacterium glutamicum for Fuel Ethanol Production under Oxygen-Deprivation Conditions", Journal of Molecular Microbiology and Biotechnology, 2004, vol. 8, No. 4, pp. 243-254.
Sasaki et al., "Simultaneous utilization of D-cellobiose, D-glucose, and D-xylose by recombinant Corynebacterium glutamicum under oxygen-deprived conditions", Appl Microbiol Biotechnol, 2008, vol. 81, No. 4, pp. 691-699.
Sasaki et al., "Engineering of pentose transport in Corynebacterium glutamicum to improve simultaneous utilization of mixed sugars", Appl Microbiol Biotechnol, 2009, vol. 85, No. 1, pp. 105-115.
Okai et al., "Production of protocatechuic acid by *Corynebacterium glutamicum* expressing chorismate-pyruvate lyase from *Escherichia coli*", Applied Microbiology and Biotechnology, 2016, vol. 100, pp. 135-145.

* cited by examiner

TRANSFORMANT, AND METHOD FOR PRODUCING PROTOCATECHUIC ACID OR SALT THEREOF USING SAME

TECHNICAL FIELD

The present invention relates to a transformant subjected to a specific genetics, thereby being able to efficiently produce protocatechuic acid or a salt thereof by using saccharides as raw materials, and to a method of efficiently producing protocatechuic acid by using this transformant.

BACKGROUND ART

Against the backdrop of global warming and exhaustion of fossil resources, production of chemical products using renewable resources has been recognized to be an important measure with view to realizing a low-carbon society, as new industrial biorefinery, along with biofuel, and has attracted attention.

Protocatechuic acid is a useful compound, as it can be used as an antioxidant by itself, while it serves as a raw material for medicine, agricultural chemicals, flavoring agents and the like.

Conventionally, protocatechuic acid is produced principally by extraction from natural products (agricultural products). With such a producing method, however, it is difficult to mass-produce protocatechuic acid, since there are problems of limited production of natural raw materials and low efficiency of extraction from natural products.

Some of microorganisms are known to have an ability of metabolically degrading a variety of aromatic compounds so as to use the compounds as carbon sources, generating protocatechuic acid as a metabolic intermediate. Considering this, proposed are methods of controlling this metabolism so as to produce a variety of compounds via protocatechuic acid by fermentation processes using saccharides as raw materials. Particularly, a method of producing a large amount of protocatechuic acid inexpensively by using saccharides derived from renewable inedible biomass resources as raw materials is environment-friendly, and the development of the same is desired.

Patent Documents 1, 2 teach methods of producing catechol from saccharides via protocatechuic acid, by using transformants that are obtained by introducing a 3-dehydroshikimate dehydratase gene and a protocatechuate decarboxylase gene derived from bacteria of the genus *Klebsiella*, into bacteria of the genus *Escherichia* or bacteria of the genus *Klebsiella*, which are able to convert a carbon source via an aromatic amino acid biosynthesis common pathway into 3-dehydroshikimate. Patent Document 2, further, teaches that for the production of catechol via protocatechuic acid, shikimate dehydrogenase is preferably inactivated so that the conversion of 3-dehydroshikimate into chorismate is inhibited.

Further, Patent Documents 3, 4 teach methods of producing cis,cis-muconate, or adipate from saccharides via protocatechuic acid, by using transformants that are obtained by introducing a 3-dehydroshikimate dehydratase gene, a protocatechuate decarboxylase gene, and a catechol 1, 2-dioxygenase gene into bacteria of the genus *Escherichia* or bacteria of the genus *Klebsiella*. Patent Documents 4, 5 teach that a certain enzyme on the metabolic pathway from 3-dehydroshikimate to chorismate is preferably inhibited.

Still further, Patent Document 5 teaches methods of producing gallic acid or pyrogallol from saccharides via protocatechuic acid, by using transformants that are obtained by introducing a 3-dehydroshikimate dehydratase gene and a variant-type 4-hydroxybenzoate hydroxylase gene into bacteria of the genus *Escherichia* or bacteria of the genus *Klebsiella*.

These Patent Documents 1 to 5, however, do not intend to produce protocatechuic acid, and it is a problem that the generated protocatechuic acid is converted to catechol, cis, cis-muconate, adipate, or gallate. Besides, practically sufficient efficiency has not been achieved yet in the production of these substances. Further, in microorganisms disclosed in these Patent Documents, pathways thereof for biosynthesizing aromatic amino acids are blocked with a view to improving the productivity of the target compounds. In a case of use of such a microorganism, which therefore has auxotrophy for tryptophan, tyrosine, phenylalanine, para-hydroxybenzoate, para-aminobenzoate, and 2,3-dihydroxybenzoate, these six types of compounds have to be added to medium.

PRIOR ART DOCUMENT

Patent Document

Patent Document 1: U.S. Pat. No. 5,629,181
Patent Document 2: U.S. Pat. No. 5,272,073
Patent Document 3: U.S. Pat. No. 5,487,987
Patent Document 4: U.S. Pat. No. 5,616,496
Patent Document 5: U.S. Pat. No. 6,472,190

SUMMARY OF THE INVENTION

Problem to be Solved by the Invention

It is an object of the present invention to provide a microorganism that efficiently produces protocatechuic acid or a salt thereof by using a saccharide as a raw material, and to provide a method of efficiently producing protocatechuic acid or a salt thereof by using the microorganism.

Means to Solve the Problem

The present inventors have wholeheartedly carried out investigations in order to achieve the object described above and found the following:

(i) Protocatechuic acid is known to be commonly cytotoxic against microorganisms, and there seemed to be a possibility that the productivity is limited by toxicity of produced protocatechuic acid. Then, some microorganisms that have been reported to produce aromatic compounds were compared regarding influences of protocatechuic acid on the growth thereof, and the results indicated that among *Corynebacterium glutamicum, Escherichia coli, Bacillus subtilis, Pseudomonas putida*, and *Rhodococcus erythropolis, Corynebacterium glutamicum* had the highest resistance against protocatechuic acid. More specifically, *Corynebacterium glutamicum* had robust growth capacity and a saccharide consumption capacity even under the presence of 500 mM protocatechuic acid, which is a high concentration, under which the growth of other microorganisms was completely or significantly inhibited. In this way, *Corynebacterium glutamicum* has extremely high resistance against protocatechuic acid, and is therefore particularly suitable for the production of protocatechuic acid or a salt thereof.

(ii) A coryneform bacterium is subjected to the following modifications in combination to enhance the production of protocatechuic acid: (a) a modification of introducing a gene that encodes 3-dehydroshikimate dehydratase into a host microorganism so as to enhance the enzyme activity thereof; and (b) a modification of introducing a gene that encodes chorismate pyruvate lyase, and a gene that encodes 4-hydroxybenzoate hydroxylase, into a host microorganism so as to enhance the enzyme activities thereof. By doing so, the efficiency in the production of protocatechuic acid or a salt thereof from saccharides is synergistically improved, as compared with a case where the modification (a) is performed alone, or a case where the modification (b) is performed alone.

(iii) Further, a coryneform bacterium transformant subjected to both of the modifications (a) and (b) has a noticeably improved efficiency in the production of protocatechuic acid or a salt thereof, while it does not have auxotrophy for aromatic amino acids such as tryptophan, tyrosine, and phenylalanine or para-aminobenzoate since the aromatic amino acid biosynthetic pathway is not blocked, thereby having an advantage that it is not necessary to add these compounds to medium in order to grow the transformant.

(iv) These transformants exhibit particularly high efficiency in the production of protocatechuic acid or a salt thereof in a case where they are subjected to aerobic reaction under such conditions that the transformants substantially do not grow.

The present invention, which has been completed based on the above-described findings, provides a transformant, and a process for producing protocatechuic acid or a salt of the same, which are described below.

Item 1. A transformant having protocatechuic acid producing ability, wherein the transformant is subjected to modifications (A), (B), and (C) below:

(A) enhancement of 3-dehydroshikimate dehydratase activity;

(B) enhancement of chorismate pyruvate lyase activity; and (C) enhancement of 4-hydroxybenzoate hydroxylase activity.

Item 2. The transformant according to Item 1,
wherein the enhancement of 3-dehydroshikimate dehydratase activity is achieved by introducing, into a host, a gene that encodes an enzyme having 3-dehydroshikimate dehydratase activity, the gene being derived from a microorganism belonging to the genus *Corynebacterium*, the genus *Rhodococcus*, the genus *Bacillus*, the genus *Rhodopseudomonas*, the genus *Alteromonas*, the genus *Marinobacter*, the genus *Methylobacterium*, the genus *Pantoea*, the genus *Neurospora*, or the genus *Aspergillus*.

Item 3. The transformant according to Item 2,
wherein the gene that encodes the enzyme having 3-dehydroshikimate dehydratase activity is a gene of *Corynebacterium glutamicum*, *Corynebacterium halotolerans*, *Corynebacterium casei*, *Corynebacterium efficiens*, *Aspergillus niger*, or *Aspergillus oryzae*.

Item 4. The transformant according to Item 2 or 3,
wherein the gene that encodes the enzyme having 3-dehydroshikimate dehydratase activity is encoded by a DNA of (a) or (b) below:

(a) a DNA which consists of a base sequence of SEQ ID NO: 7, 134, 135, 145, 147, or 149; or (b) a DNA which consists of a base sequence having 90% or more of identity with a base sequence of SEQ ID NO: 7, 134, 135, 145, 147, or 149, the DNA encoding a polypeptide having 3-dehydroshikimate dehydratase activity.

Item 5. The transformant according to any one of Items 1 to 4,
wherein the enhancement of chorismate pyruvate lyase activity is achieved by introducing, into a host, a gene that encodes an enzyme having chorismate pyruvate lyase activity, the gene being derived from the genus *Providencia*, or the genus *Cronobacter*.

Item 6. The transformant according to Item 5,
wherein the enhancement of chorismate pyruvate lyase activity is achieved by introducing, into a host, a gene that encodes an enzyme having chorismate pyruvate lyase activity, the gene being derived from *Providencia rustigianii*, *Providencia stuartii*, or *Cronobacter sakazakii*.

Item 7. The transformant according to any one of Items 1 to 6,
wherein the enhancement of chorismate pyruvate lyase activity is achieved by introducing, into a host, a DNA of (c) or (d) below:

(c) a DNA which consists of a base sequence of SEQ ID NO: 9, 128, or 129; or (d) a DNA which consists of a base sequence having 90% or more of identity with a base sequence of SEQ ID NO: 9, 128, or 129, the DNA encoding a polypeptide having chorismate pyruvate lyase activity.

Item 8. The transformant according to any one of Items 1 to 7,
wherein the enhancement of 4-hydroxybenzoate hydroxylase activity is achieved by introducing, into a host, a gene of *Corynebacterium glutamicum* that encodes an enzyme having 4-hydroxybenzoate hydroxylase activity.

Item 9. The transformant according to any one of Items 1 to 8,
wherein the enhancement of 4-hydroxybenzoate hydroxylase activity is achieved by introducing, into a host, a DNA of (e) or (f) below:

(e) a DNA which consists of a base sequence of SEQ ID NO: 8; or (f) a DNA which consists of a base sequence having 90% or more of identity with a base sequence of SEQ ID NO: 8, the DNA encoding a polypeptide having 4-hydroxybenzoate hydroxylase activity.

Item 10. The coryneform bacterium transformant according to any one of Items 1 to 9,
wherein protocatechuic acid-3,4-dioxygenase activity is eliminated, inhibited, or reduced.

Item 11. The transformant according to any one of Items 1 to 10,
wherein activity of at least one enzyme selected from the group consisting of 3-deoxy-D-arabino-heptulosonate-7-phosphate (DAHP) synthase, 3-dehydroquinate synthase, 3-dehydroquinate dehydratase, shikimate dehydrogenase, shikimate kinase, 5-enolpyruvylshikimate-3-phosphate (EPSP) synthase, and chorismate synthase is enhanced.

Item 12. The transformant according to Item 11,
wherein the enhancement of DAHP synthase activity is achieved by introducing, into a host, a DNA of (g) or (h) below, the enhancement of 3-dehydroquinate synthase activity is achieved by introducing, into a host, a DNA of (i) or (j) below, the enhancement of 3-dehydroquinate dehydratase activity is achieved by introducing, into a host, a DNA of (k) or (l) below, the enhancement of shikimate dehydrogenase activity is achieved by introducing, into a host, a DNA of (m) or (n) below, the enhancement of shikimate kinase activity is achieved by introducing, into a host, a DNA of (o) or (p) below, the enhancement of EPSP synthase activity is achieved by introducing, into a host, a DNA of (q) or (r) below, and the enhancement of chorismate synthase activity is achieved by introducing, into a host, a DNA of (s) or (t) below:

(g) a DNA which consists of a base sequence of SEQ ID NO: 2;

(h) a DNA which consists of a base sequence having 90% or more of identity with SEQ ID NO: 2, the DNA encoding a polypeptide having DAHP synthase activity;

(i) a DNA which consists of a base sequence of SEQ ID NO: 153;

(j) a DNA which consists of a base sequence having 90% or more of identity with SEQ ID NO: 153, the DNA encoding a polypeptide having 3-dehydroquinate synthase activity;

(k) a DNA which consists of a base sequence of SEQ ID NO: 5;

(l) a DNA which consists of a base sequence having 90% or more of identity with SEQ ID NO: 5, the DNA encoding a polypeptide having 3-dehydroquinate dehydratase activity;

(m) a DNA which consists of a base sequence of SEQ ID NO: 6;

(n) a DNA which consists of a base sequence having 90% or more of identity with SEQ ID NO: 6, the DNA encoding a polypeptide having shikimate dehydrogenase activity;

(o) a DNA which consists of a base sequence of SEQ ID NO: 154;

(p) a DNA which consists of a base sequence having 90% or more of identity with SEQ ID NO: 154, the DNA encoding a polypeptide having shikimate kinase activity;

(q) a DNA which consists of a base sequence of SEQ ID NO: 155;

(r) a DNA which consists of a base sequence having 90% or more of identity with SEQ ID NO: 155, the DNA encoding a polypeptide having EPSP synthase activity;

(s) a DNA which consists of a base sequence of SEQ ID NO: 156; and (t) a DNA which consists of a base sequence having 90% or more of identity with SEQ ID NO: 156, the DNA encoding a polypeptide having chorismate synthase activity.

Item 13. The transformant according to any one of Items 1 to 12 wherein at least one activity selected from the group consisting of transketolase activity and transaldolase activity is enhanced.

Item 14. The transformant according to Item 13, wherein the enhancement of transketolase activity is achieved by introducing a DNA of (u) or (v) below, and the enhancement of transaldolase activity is achieved by introducing a DNA of (w) or (x) below:

(u) a DNA which consists of a base sequence of SEQ ID NO: 151;

(v) a DNA which consists of a base sequence having 90% or more of identity with SEQ ID NO: 151, the DNA encoding transketolase;

(w) a DNA which consists of a base sequence of SEQ ID NO. SEQ ID NO: 152; and (x) a DNA which consists of a base sequence having 90% or more of identity with SEQ ID NO: 152, the DNA encoding transaldolase.

Item 15. The transformant according to any one of Items 1 to 14, wherein the host is a coryneform bacterium.

Item 16. The transformant according to Item 15, wherein the transformant has simultaneous utilization ability of at least one saccharide selected from the group consisting of glucose, xylose, arabinose, and cellobiose.

Item 17. The transformant according to Item 15 or 16, wherein the coryneform bacterium as a host is a bacterium of the genus *Corynebacterium*.

Item 18. The transformant according to Item 17, wherein the bacterium of the genus *Corynebacterium* as a host is *Corynebacterium glutamicum*.

Item 19. The coryneform bacterium transformant according to Item 18, wherein *Corynebacterium glutamicum* as a host is *Corynebacterium glutamicum* R (FERM BP-18976), ATCC13032, or, ATCC13869.

Item 20. *Corynebacterium glutamicum* PCA4 (Accession Number: NITE BP-02217)

Item 21. A method of producing protocatechuic acid or a salt thereof, wherein the method includes the step of culturing the transformant according to any one of Items 1 to 20 in a reaction solution containing a saccharide so as to cause the transformant to produce protocatechuic acid or a salt thereof.

Item 22. The method according to Item 21, comprising culturing the transformant under conditions that are aerobic and under which the transformant does not grow.

Effect of the Invention

As illustrated in FIG. 1, as a protocatechuic acid biosynthetic pathway in a microorganism, there are the following two types of pathways: (a) a protocatechuic acid producing pathway consisting of conversion of 3-dehydroshikimate into protocatechuic acid, catalyzed by 3-dehydroshikimate dehydratase; and (b) a protocatechuic acid producing pathway consisting of conversion of chorismate (a metabolic end product of a shikimate pathway) into protocatechuic acid, catalyzed by chorismate pyruvate lyase and 4-hydroxybenzoate hydroxylase.

According to the present invention, the above-described two metabolic pathways (a) and (b), which are pathways that diverge at 3-dehydroshikimate and then both lead to the production of protocatechuic acid, are simultaneously strengthened, whereby a noticeable increase is achieved in the production of protocatechuic acid unexpectedly. More specifically, by simultaneously subjecting a coryneform bacterium to the modification of the metabolic pathway (a) that enhances 3-dehydroshikimate dehydratase activity, and the modification of the metabolic pathway (b) that enhances chorismate pyruvate lyase activity and 4-hydroxybenzoate hydroxylase activity, the amount of protocatechuic acid or a salt thereof produced from saccharides synergistically increases, as compared with a case where only the same modification of the metabolic pathway (a) is performed, or a case where only the same modification of the metabolic pathway (b) is performed.

Considering that it is known that inhibiting the conversion from 3-dehydroshikimate to chorismate is more preferable in the method of producing catechol via the production of protocatechuic acid from 3-dehydroshikimate by using 3-dehydroshikimate dehydratase activity (Patent Documents 1 to 5), the effect of the present invention is difficult to predict.

The enhancement of these enzyme activities can be achieved by, for example, placing a gene that encodes the enzyme under the control of an appropriate promoter and introducing the gene into a coryneform bacterium.

Incidentally, a coryneform bacterium has a gene that encodes 3-dehydroshikimate dehydratase, and a gene that encodes 4-hydroxybenzoate hydroxylase, on the chromosome, among the three enzymes described above, but it does not have a gene that encodes chorismate pyruvate lyase. In the examples of the present invention, a gene derived from *Providencia rustigianii*, which we found encodes chorismate pyruvate lyase having high activity, was introduced into a coryneform bacterium as a host, whereby the pathway for protocatechuic acid biosynthesis of (b) was caused to function in the coryneform bacterium.

The present invention made it possible to mass-produce protocatechuic acid, which is useful as a raw material for pharmaceutical products, flavoring agent, polymers and the like, by a fermentation process that causes less environmental loads, at a low cost.

Generally, since the growth of a microorganism is inhibited by cytotoxicity of an aromatic compound such as protocatechuic acid, it was difficult to manufacture protocatechuic acid by using microorganisms. A coryneform bacterium, however, has a significantly high resistance against aromatic compound including protocatechuic acid, and by using a transformant of the present invention, it is possible to efficiently produce protocatechuic acid or a salt thereof at a high concentration. Further, a coryneform bacterium, unlike *Escherichia coli*, does not generate endotoxin, which makes it unnecessary to worry about residues of endotoxin in products. Still further, in the case of the coryneform bacterium, the reaction of generating protocatechuic acid or a salt thereof proceeds without bacteriolysis, even under conditions where coryneform bacteria are filled in a culture vessel at a high cell density and the growth of the same is limited. Saccharides as raw materials therefore are not consumed for growth of the same, which makes the yield of protocatechuic acid or a salt thereof higher. Besides, under the conditions where the growth is limited, it is unnecessary to add an aromatic amino acid, 4-hydroxybenzoate, or the like that are generally required for the growth of microorganisms, to a culture solution, whereby the production costs can be reduced accordingly.

Further, in the cases of the methods disclosed in Patent Documents 1 to 4, the production reaction of chorismate from 3-dehydroshikimate is inhibited, and as a result, a transformant exhibits aromatic amino acid auxotrophy. It is therefore necessary to additionally add aromatic amino acids and aromatic vitamins for growth. This increases the costs of the production of materials by transformants, and further, it can be considered that the growth ability of bacterial cells possibly decreases. On the other hand, in the case of the transformant of the present invention, the production of chorismate is not inhibited and the transformant does not have auxotrophy. It is therefore unnecessary to additionally add aromatic amino acids and aromatic vitamins in bacterial cell growth (culture) for preparing bacterial cells for reaction as well, and the bacterial cells grow more vigorously as compared with strains that exhibit auxotrophy.

MODE FOR CARRYING OUT THE INVENTION

Figure 1:
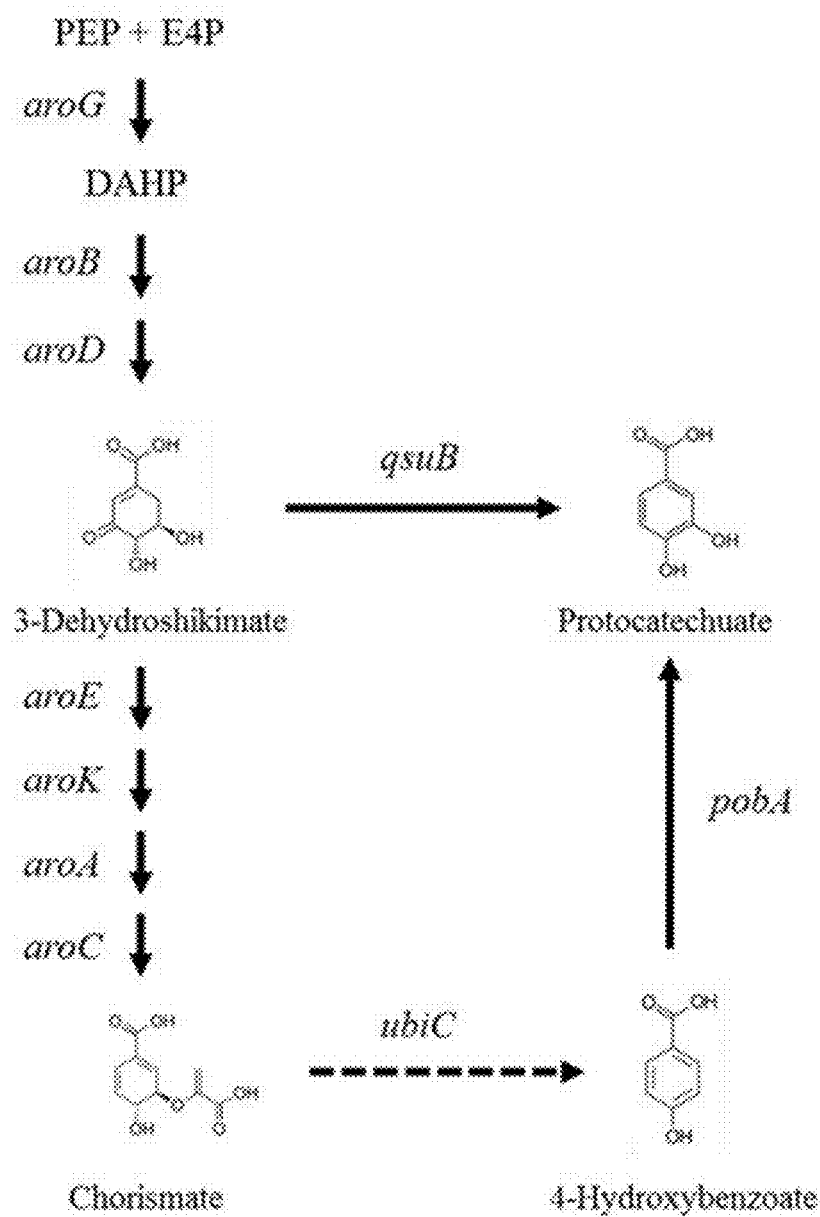
FIG. 1 illustrates a protocatechuic acid producing pathway in a coryneform bacterium. The dotted line indicates a metabolic reaction by a foreign gene product.

The following describes the present invention in detail.
To make the present invention more understandable, the pathway for protocatechuic acid biosynthesis in the coryneform bacterium transformant is schematically illustrated in FIG. 1.

(1) Transformant Having Ability of Producing Protocatechuic Acid or a Salt Thereof Host In the present invention, any microorganism can be used as a host as long as it has an ability of producing protocatechuic acid.

Examples of a preferable host microorganism include bacteria of the genus *Corynebacterium*, bacteria of the genus *Escherichia* (particularly, *Escherichia coli*), bacteria of the genus *Bacillus* (particularly *Bacillus subtilis*), bacteria of the genus *Pseudomonas* (particularly, *Pseudomonas putida*), bacteria of the genus *Brevibacterium*, bacteria of the genus *Streptococcus*, bacteria of the genus *Lactobacillus*, bacteria of the genus *Rhodococcus* (particularly *Rhodococcus erythropolis*, *Rhodococcus opacus*), bacteria of the genus *Streptomyces*, yeasts of the genus *Saccharomyces* (particularly, *Saccharomyces cerevisiae*), yeasts of the genus *Kluyveromyces*, yeasts of the genus *Schizosaccharomyces*, yeasts of the genus *Yarrowia*, yeasts of the genus *Trichosporon*, yeast *Rhodosporidium*, yeasts of the genus *Pichia*, yeasts of the genus *Candida*, fungi of the genus *Neurospora*, fungi of the genus *Aspergillus*, and fungi of the genus *Trichoderma*.

Among these, a coryneform bacterium is preferably used as a host regarding the efficiency in the production of protocatechuic acid or a salt thereof.

The coryneform bacteria are a group of microorganisms defined in Bergey's Manual of Determinative Bacteriology, Vol. 8, 599 (1974), and are not particularly limited as long as they grow under normal aerobic conditions. The specific examples include bacteria of the genus *Corynebacterium*, bacteria of the genus *Brevibacterium*, bacteria of the genus *Arthrobacter*, bacteria of the genus *Mycobacterium* and bacteria of the genus *Micrococcus*. Among the coryneform bacteria, the genus *Corynebacterium* is preferred.

Examples of the genus *Corynebacterium* include *Corynebacterium glutamicum*, *Corynebacterium efficiens*, *Corynebacterium ammoniagenes*, *Corynebacterium halotolerans*, and *Corynebacterium alkanolyticum*.

Among them, *Corynebacterium glutamicum* is preferred for safety and high efficiency in the production of protocatechuic acid. Examples of preferred strains include *Corynebacterium glutamicum* R (FERM BP-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (FERM BP-1497), MJ-233AB-41 (FERM BP-1498). These strains are internationally deposited under the Budapest Treaty, and available to the public.

Among them, strains R (FERM BP-18976), ATCC13032, and ATCC13869 are preferred.

According to molecular biological classification, names of some species of coryneform bacteria, such as *Brevibacterium flavum*, *Brevibacterium lactofermentum*, *Brevibacterium divaricatum*, and *Corynebacterium lilium* are standardized to *Corynebacterium glutamicum* [Liebl, W. et al., Transfer of *Brevibacterium divaricatum* DSM 20297T, "*Brevibacterium flavum*" DSM 20411, "*Brevibacterium lactofermentum*" DSM 20412 and DSM 1412, and *Corynebacterium glutamicum* and their distinction by rRNA gene restriction patterns. Int J Syst Bacteriol. 41:255-260. (1991), Kazuo Komagata et al., "Classification of the coryneform group of bacteria", Fermentation and Industry, 45:944-963 (1987)].

Examples of the genus *Brevibacterium* include *Brevibacterium ammoniagenes* (for example, ATCC6872).

Examples of the genus *Arthrobacter* include *Arthrobacter globiformis* (for example, ATCC8010, ATCC4336, ATCC21056, ATCC31250, ATCC31738, and ATCC35698).

Examples of the genus *Mycobacterium* include *Mycobacterium bovis* (for example, ATCC19210, ATCC27289).

Examples of the genus *Micrococcus* include *Micrococcus freudenreichii* (for example, Strain No. 239 (FERM P-13221)), *Micrococcus leuteus* (for example, Strain No. 240 (FERM P-13222)), *Micrococcus ureae* (for example, IAM1010), and *Micrococcus roseus* (for example, IFO3764).

These strains of the genus *Brevibacterium*, the genus *Arthrobacter*, the genus *Mycobacterium*, and the genus *Micrococcus* are internationally deposited under the Budapest Treaty, and available to the public.

The coryneform bacteria may be, let alone a wild type, a mutant thereof or an artificial recombinant thereof. Examples thereof include strain in which a gene such as lactate dehydrogenase (LDH), phosphoenolpyruvate carboxylase, or malate dehydrogenase is disrupted. Among them, preferred is a disruptant in which a lactate dehydrogenase gene is disrupted. In the disruptant, the lactate dehydrogenase gene is disrupted and the metabolic pathway from pyruvate to lactic acid is blocked. Particularly preferred is a disruptant of *Corynebacterium glutamicum*, especially the strain R (FERM BP-18976) in which the lactate dehydrogenase gene is disrupted.

Such a disruptant can be prepared by a conventional gene engineering process. Such a lactate dehydrogenase disruptant and the preparation process thereof are described in WO 2005/010182 A1, for example.

Figure 2:
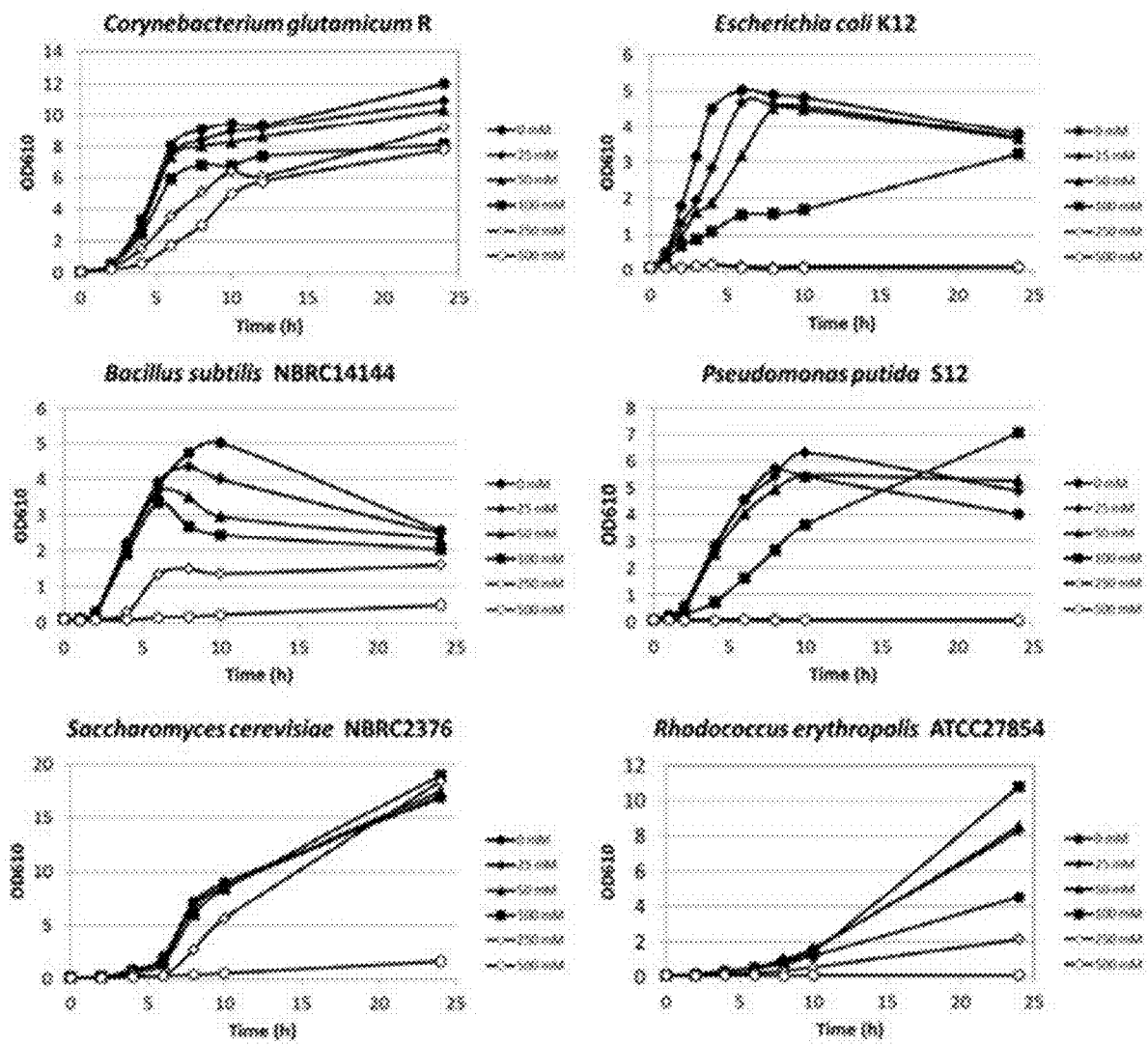
FIG. 2 illustrates influences of protocatechuic acid on growth of various types of microorganisms.
Figure 3:
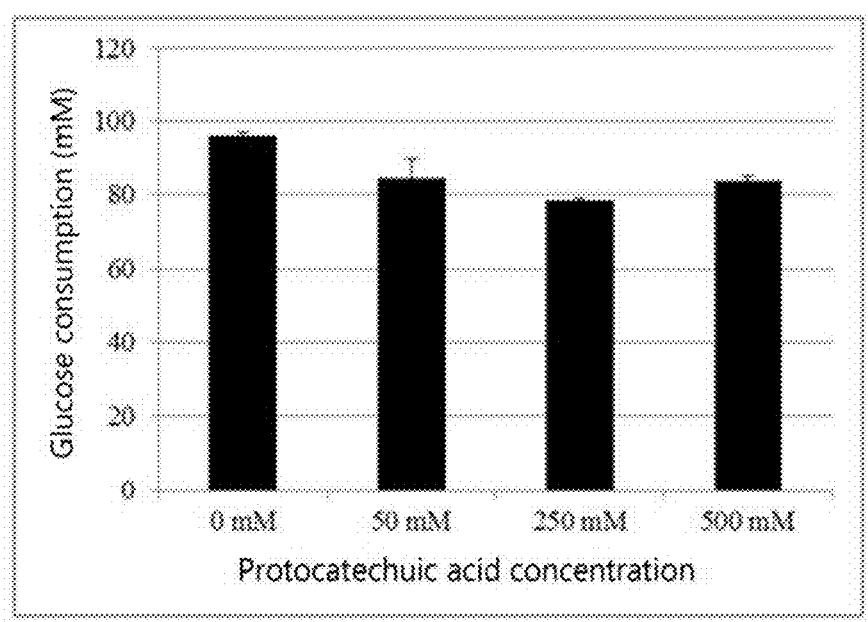
FIG. 3 illustrates influences of protocatechuic acid on saccharide consumption by a coryneform bacterium.

The inventors found that, as shown in FIG. 2, coryneform bacteria have extremely higher protocatechuic acid resistance compared with other bacteria. Besides, as shown in FIG. 3, coryneform bacteria had high saccharide consumption ability even under the presence of a high concentration of protocatechuic acid. In this regard, coryneform bacteria are suitable for the production of protocatechuic acid or a salt thereof by the method of the present invention.

Transgene

A transformant that efficiently generates protocatechuic acid in the present invention can be obtained by enhancing respective enzyme activities of 3-dehydroshikimate dehydratase, chorismate pyruvate lyase, and 4-hydroxybenzoate hydroxylase in a host strain.

3-dehydroshikimate dehydratase catalyzes a reaction of generating protocatechuic acid from 3-dehydroshikimate. Chorismate pyruvate lyase catalyzes a reaction of generating 4-hydroxy benzoate from chorismate. 4-hydroxybenzoate hydroxylase catalyzes a reaction of generating protocatechuic acid by hydroxylating a carbon atom at the third position of the aromatic ring of 4-hydroxy benzoate.

Activities of these enzymes can be enhanced by introducing genes that encode these enzymes into a host microorganism. Further, activities of these enzymes can be enhanced also by mutate or base sequence substitution with respect to a regulatory sequence, a gene coding region, or both of each enzyme gene on a chromosome of a host microorganism. Among these, enhancing the enzyme activities by introducing these enzyme genes into a host microorganism is convenient and efficient.

In a case where a coryneform bacterium is used as a host, this bacterium has, on its chromosome, a 3-dehydroshikimate dehydratase gene, and a 4-hydroxybenzoate hydroxylase gene, but does not have a chorismate pyruvate lyase gene. Further, regarding the 3-dehydroshikimate dehydratase gene and the 4-hydroxybenzoate hydroxylase gene, it can be considered possible that the expression of these genes is induced only under particular culture conditions (under the presence of protocatechuic acid, or a particular aromatic compound). The foregoing three genes, therefore, are preferably introduced into a host coryneform bacterium, as fusion genes placed under the control of a suitable promotor that allows the genes to be highly expressed under culture conditions used.

Though the origin of each gene is not limited particularly, examples of the genes include those of the following microorganisms, considering that they have good efficiency in the production of protocatechuic acid or a salt thereof.

3-dehydroshikimate Dehydratase Gene

Examples of a 3-dehydroshikimate dehydratase gene include genes of bacteria of the genus *Corynebacterium* (particularly, *Corynebacterium glutamicum*, *Corynebacterium casei*, *Corynebacterium efficiens*, *Corynebacterium halotolerans*), bacteria of the genus *Rhodococcus* (particularly, *Rhodococcus opacus*), bacteria of the genus *Mycobacterium* (particularly, *Mycobacterium smegmatis*), bacteria of the genus *Bacillus* (particularly, *Bacillus thuringiensis*), bacteria of the genus *Gluconobacter* (particularly, *Gluconobacter oxydans*), bacteria of the genus *Rhodopseudomonas* (particularly, *Rhodopseudomonas palustris*), bacteria of the genus *Alteromonas* (particularly, *Alteromonas macleodii*), bacteria of the genus *Marinobacter* (particularly, *Marinobacter hydrocarbonoclasticus*), bacteria of the genus *Methylobacterium* (particularly, *Methylobacterium extorquens*), bacteria of the genus *Pseudomonas* (particularly, *Pseudomonas putida*), bacteria of the genus *Acinetobacter* (particularly, *Acinetobacter baylyi*), bacteria of the genus *Pantoea* (particularly, *Pantoea ananatis*), bacteria of the genus *Neurospora* (particularly, *Neurospora crassa*), and bacteria of the genus *Aspergillus* (particularly, *Aspergillus oryzae*, *Aspergillus niger*).

Among these, genes of *Corynebacterium glutamicum*, *Corynebacterium casei*, *Corynebacterium efficiens*, *Corynebacterium halotolerans*, *Rhodococcus opacus*, *Methylobacterium extorquens*, *Neurospora crassa*, *Aspergillus niger*, and *Aspergillus oryzae* are preferable, among which genes of *Corynebacterium glutamicum*, and *Corynebacterium halotolerans* are more preferable.

Examples of the 3-dehydroshikimate dehydratase gene include genes of *Corynebacterium glutamicum*, *Corynebacterium casei*, *Corynebacterium efficiens*, *Corynebacterium halotolerans*, *Rhodococcus opacus*, *Mycobacterium smegmatis*, *Bacillus thuringiensis*, *Gluconobacter oxydans*, *Rhodopseudomonas palustris*, *Alteromonas macleodii*, *Marinobacter hydrocarbonoclasticus*, *Methylobacterium extorquens*, *Pseudomonas putida*, *Acinetobacter baylyi*, *Pantoea ananatis*, *Neurospora crassa*, *Aspergillus oryzae*, and *Aspergillus niger* include genes that have base sequences represented by SEQ ID NO:7, and SEQ ID NOs: 134 to 150.

The 3-dehydroshikimate dehydratase gene of *Corynebacterium glutamicum* of SEQ ID NO: 7 is referred to as qsuB.

Further, a DNA that hybridizes to a DNA which consists of a base sequence complementary to a base sequence of any one of SEQ ID NOs: 7, 134 to 150 under stringent conditions, and encodes a polypeptide having 3-dehydroshikimate dehydratase activity, can be used as well.

In the present invention, "stringent conditions" means conditions in which hybridization is performed in a hybridization solution at a salt concentration of 6×SSC at 50 to 60° C. for 16 hours and then washing with a solution at a salt concentration of 0.1×SSC is performed.

Further, a DNA which consists of a base sequence having 90% or more, preferably 95% or more, more preferably 98% or more of identity with a base sequence of any one of SEQ ID NOs: 7, 134 to 150, and encodes a polypeptide having 3-dehydroshikimate dehydratase activity can be used as well.

In the present invention, the identities of base sequences were calculated using GENETYX Ver. 8 (manufactured by Genetyx Corporation).

The 3-dehydroshikimate dehydratase activity is measured in the following manner: at 33° C., an enzyme solution to be tested is added to a reaction mixture solution composed of 50 mM tris-HCl buffer (pH 7.5), 0.5 mM 3-dehydroshikimate, and 25 mM $MgCl_2$ to allow the reaction to start, and an increase in the absorbance at 290 nm (absorption coefficient=3890/M·cm), indicative of the production of protocatechuic acid, is monitored with a Beckman DU800 spectrophotometer (manufactured by Beckman Coulter). Activity of causing 1 μmol of protocatechuic acid to be produced per minute at 33° C. is assumed to be 1 unit of 3-dehydroshikimate dehydratase activity. When such an activity is detected, it is determined that there is the 3-dehydroshikimate dehydratase activity.

Also, in the present invention, the enhancement of the 3-dehydroshikimate dehydratase activity of a transformant is confirmed by measuring the 3-dehydroshikimate dehydratase activity in a cell extract of the transformant.

Chorismate Pyruvate Lyase Gene

Though the origin of chorismate pyruvate lyase gene is not limited particularly, genes of bacteria of the genus *Providencia* and bacteria of the genus *Cronobacter* are preferable in that they have good efficiency in the production of protocatechuic acid or a salt thereof. Among these, genes of *Providencia rustigianii*, *Providencia stuartii*, and *Cronobacter sakazakii* are more preferable, among which the gene of *Providencia rustigianii* is further more preferable.

Examples of the chorismate pyruvate lyase genes of *Providencia rustigianii*, *Providencia stuartii*, and *Cronobacter sakazakii* include genes having base sequences represented by SEQ ID NOs: 9, 128, and 129.

The chorismate pyruvate lyase gene of *Providencia rustigianii* of SEQ ID NO: 9 is referred to as ubiC.

Further, a DNA that hybridizes to a DNA which consists of a base sequence complementary to a base sequence of any one of SEQ ID NOs: 9, 128, and 129 under stringent conditions, and encodes a polypeptide having chorismate pyruvate lyase activity, can be used as well.

Further, a DNA which consists of a base sequence having 90% or more, preferably 95% or more, more preferably 98% or more of identity with any one of base sequences of SEQ ID NOs: 9, 128, and 129, and encodes a polypeptide having chorismate pyruvate lyase activity can be used as well.

The chorismate pyruvate lyase activity is measured by a method obtained by modifying the method disclosed in "Journal of Bacteriology, 174, 5309-5316, 1992 'Materials and Methods'. More specifically, at 33° C., an enzyme solution to be tested is added to a reaction mixture solution composed of 50 mM tris-HCl buffer (pH 7.5), 20 mM NaCl, 0.2 mM NADH, 0.5 mM chorismate, and 5 U/ml lactate dehydrogenase, to allow the reaction to start. A decrease in absorbance at 340 nm (absorption coefficient=6220/M·cm) in association of the consumption of NADH occurring with a coupling reaction of lactate dehydrogenase using pyruvate as a substrate that is generated by the enzyme activity is monitored with Beckman DU800 spectrophotometer (manufactured by Beckman Coulter, Inc.), and the enzyme activity is calculated from the initial reaction rate. Activity of causing 1 μmol of NADH to be consumed per one minute at 33° C. is assumed to be 1 unit of chorismate pyruvate lyase activity, and when such an activity is detected, it is determined that there is the chorismate pyruvate lyase activity.

Also, in the present invention, the enhancement of the chorismate pyruvate lyase activity of a transformant is confirmed when an increase in the chorismate pyruvate lyase activity in a cell extract of the transformant is detected.

4-hydroxybenzoate Hydroxylase Gene 4-hydroxybenzoate hydroxylase is also referred to as phenol monooxygenase. Though the origin of a 4-hydroxybenzoate hydroxylase gene is not limited particularly, a gene of bacteria of the genus *Corynebacterium*, in particular, *Corynebacterium glutamicum*, is preferable in that it has good efficiency in the production of protocatechuic acid or a salt thereof.

Examples of 4-hydroxybenzoate hydroxylase gene of *Corynebacterium glutamicum* include a gene having a base sequence represented by SEQ ID NO: 8. The 4-hydroxybenzoate hydroxylase gene of *Corynebacterium glutamicum* is referred to as pobA.

A DNA that hybridizes to a DNA which consists of a base sequence complementary to a base sequence of SEQ ID NO:8 under stringent conditions, and encodes a polypeptide having 4-hydroxybenzoate hydroxylase activity, can be used as well.

Further, a DNA which consists of a base sequence having 90% or more, preferably 95% or more, more preferably 98% or more of identity with a base sequence of SEQ ID NO:8, and encodes a polypeptide having 4-hydroxybenzoate hydroxylase activity can be used as well.

The 4-hydroxybenzoate hydroxylase activity is measured in the following manner: at 33° C., an enzyme solution to be tested is added to a reaction mixture solution composed of 50 mM tris-HCl buffer (pH 8.0), 0.2 mM NADPH, and 2 mM 4-hydroxy benzoate to allow the reaction to start, and a decrease in the absorbance at 340 nm (absorption coefficient=6220/M·cm) is monitored with Beckman DU800 spectrophotometer (manufactured by Beckman Coulter), so that the enzyme activity is calculated from an initial reaction rate. Activity of causing 1 μmol of NADPH to be consumed per one minute at 33° C. is assumed to be one unit of 4-hydroxybenzoate hydroxylase activity, and when such an activity is detected, it is determined that there is the 4-hydroxybenzoate hydroxylase activity.

Also, in the present invention, the enhancement of the 4-hydroxybenzoate hydroxylase activity of a transformant is confirmed when an increase in the 4-hydroxybenzoate hydroxylase activity in a cell extract of the transformant is detected.

Enhancement of 3-deoxy-D-arabino-heptulosonate-7-phosphate (DAHP) Synthase Activity The transformant of the present invention preferably has enhanced activity of 3-deoxy-D-arabino-heptulosonate-7-phosphate (DAHP) synthase. The DAHP synthase is an enzyme that generates DAHP as an initial metabolic product of an aromatic compound biosynthesis pathway from erythrose-4-phosphate and phosphoenolpyruvate.

The DAHP synthase activity can be enhanced by introducing a DAHP synthase gene into a host microorganism, or mutatate or sequence substitution with respect to (a regulatory sequence or region, a gene coding region, or both of) a DAHP synthase gene on a chromosome of a host microorganism. Among these, enhancing DAHP synthase activity by introducing a DAHP synthase gene into a host microorganism is convenient and efficient.

Though the origin of a DAHP synthase gene to be introduced is not limited particularly, a gene of bacteria of *Corynebacterium glutamicum* or *Escherichia coli* is preferable in that it has good efficiency in the production of protocatechuic acid or a salt thereof. Among these, a gene derived from *Escherichia coli* is more preferable.

Among the DAHP synthase genes derived from *Escherichia coli*, a DNA (aroG$^{S180F}$) which consists of a base sequence represented by SEQ ID NO: 2 is further more preferable. This gene is gene aroG, which is a DAHP synthase gene derived from *Escherichia coli*, into which a mutation (S180F) that changes the serine at position 180 to phenylalanine is introduced, and a gene product of this exhibits resistance against feedback inhibition by an aromatic compound containing an aromatic amino acid, and high DAHP synthase activity. This was found by the inventors of the present invention by comparative investigation (unpublished).

Further, in the present invention, a DNA which consists of a base sequence having 90% or more, preferably 95% or more, more preferably 98% or more of identity with SEQ ID NO: 2, and encodes a polypeptide having DAHP synthase activity, or a DNA that hybridizes to a DNA which consists of a base sequence complementary to a base sequence of SEQ ID NO: 2 under stringent conditions, and encodes a polypeptide having DAHP synthase activity, can be used as well.

The DAHP synthase activity is measured in the following manner: an enzyme solution to be tested is added to a reaction mixture solution composed of 20 mM bis-tris propane buffer (pH 6.8), 500 μM phosphoenolpyruvate (PEP) sodium, 500 μM erythrose-4-phosphate, and 1 mM manganese chloride to allow the reaction to start, and a decrease in the absorbance at 232 nm (absorption coefficient=2800/M·cm) in association with PEP is monitored with Beckman DU800 spectrophotometer (manufactured by Beckman Coulter), so that the enzyme activity is calculated from an initial reaction rate. Activity of causing 1 μmol of PEP to be consumed per one minute at 33° C. is assumed to be one unit of DAHP synthase activity, and when such an activity is detected, it is determined that there is the DAHP synthase activity. Also, in the present invention, the enhancement of the DAHP synthase activity of a transformant is confirmed when an increase in the value indicating the DAHP synthase activity in a cell extract of the transformant is detected.

Enhancement of the Activities of Transketolase and Transaldolase

The transformant of the present invention preferably has enhanced transketolase activity, or enhanced transketolase activity and transaldolase activity.

In saccharide metabolism, transketolase catalyzes two types of reactions. In the non-oxidative pentose phosphate pathway, transketolase catalyzes, as the first type of reactions, the conversion from D-xylulose-5-phosphate to glyceraldehyde-3-phosphate and the conversion from D-ribose-5-phosphate (R5P) to sedoheptulose-7-phosphate (S7P). These reactions are reversible and conjugated. Also, transketolase catalyzes, as the second type of reactions, the conversion from D-fructose-6-phosphate (F6P) to erythrose-4-phosphate (E4P) and the conversion from glyceraldehyde-3-phosphate to D-xylulose-5-phosphate. These reactions are reversible and conjugated.

Also, in saccharide metabolism, transaldolase catalyzes the conversion from glyceraldehyde-3-phosphate to erythrose-4-phosphate, and the conversion from sedoheptulose-7-phosphate to D-fructose-6-phosphate. These reactions are conjugated.

Thus, transketolase and transaldolase play important roles in the production of erythrose-4-phosphate, which is one of the precursors of aromatic compound biosynthesis. It is therefore expected that enhancement of these enzyme activities increases intracellularly supplied erythrose-4-phosphate and this results in an increase in metabolic flux to an aromatic compound biosynthesis pathway, which improves the productivity of protocatechuic acid.

Transketolase activity and transaldolase activity can be enhanced by introducing a transketolase gene and a transaldolase gene into a host microorganism, or by mutatate or sequence substitution with respect to a regulatory sequence, a gene coding region, or both of each of the transketolase gene or the transaldolase gene on a chromosome of a host microorganism. Among these, enhancing the enzyme activities by introducing the transketolase gene or the transaldolase gene into a host microorganism is convenient and efficient.

Though the origins of the transfect transketolase gene and the transaldolase gene to be introduced are not limited particularly, a transfect transketolase gene and a transaldolase gene of bacteria of the genus *Corynebacterium*, in particular, *Corynebacterium glutamicum*, are preferable in that they have good efficiency in the production of protocatechuic acid or a salt thereof.

Examples of the transketolase gene of *Corynebacterium glutamicum* include the DNA which consists of the base sequence of SEQ ID NO: 151 (tkt), and examples of the transaldolase gene of *Corynebacterium glutamicum* include the DNA which consists of the base sequence of SEQ ID NO: 152 (tal).

In the present invention, a DNA which consists of a base sequence having 90% or more, in particular 95% or more, in particular 98% or more of identity with the base sequence of SEQ ID NO: 151 or 152 and which encodes a polypeptide having transketolase activity or transaldolase activity can also be used.

In the present invention, a DNA that hybridizes to a DNA which consists of a base sequence complementary to a base sequence of SEQ ID NO: 151 or 152 under stringent conditions and which encodes a polypeptide having transketolase activity or transaldolase activity can also be used.

In the present invention, the transketolase activity is measured by a modification of a known method (Sugimoto and Shiio, Agric. Biol. Chem. 53: 2081-2087 (1989)). More specifically, at 33° C., an enzyme solution to be tested is added to a reaction mixture solution composed of 50 mM tris-HCl buffer (pH 7.5), 0.5 mM MgCl$_2$, 0.01 mM thiamine diphosphate, 1 mM NADH, 3 U glycerol 3-phosphate dehydrogenase, 10 U triosephosphate isomerase, 0.5 mM D-ribose-5-phosphate, and 0.5 mM D-xylulose-5-phosphate, to allow the reaction to start, and a decrease in the absorbance at 340 nm (absorption coefficient=12000/M·cm) is monitored with Beckman DU800 spectrophotometer, so that the enzyme activity is calculated from an initial reaction rate. Activity of causing 1 μmol of NADH to be consumed per one minute at 33° C. is assumed to be one unit of transketolase activity, and when such an activity is detected, it is determined that there is the transketolase activity.

Also, in the present invention, the enhancement of the transketolase activity of a transformant is confirmed when an increase in the value indicating the transketolase activity in a cell extract of the transformant is detected.

In the present invention, transaldolase activity is measured by a modification of a known method (Sprenger, G A. et al., J. Bacteriol. 177: 5930-5936 (1995)). More specifically, at 33° C., an enzyme solution to be tested is added to a reaction mixture solution composed of 100 mM triethanolamine-HCl buffer (pH 7.6), 10 mM EDTA, 2.5 mM fructose-6-phosphate, 0.5 mM erythrose-4-phosphate, 0.5 mM NADH, 0.5 U/ml glycerol 3-phosphate dehydrogenase, and 5 U/ml triosephosphate isomerase, to allow the reaction to start, and a decrease in the absorbance at 340 nm (absorption coefficient=12000/M·cm) is monitored with Beckman DU800 spectrophotometer, so that the enzyme activity is calculated from an initial reaction rate. Activity of causing 1 μmol of NADH to be consumed per one minute at 33° C. is assumed to be one unit of transaldolase activity, and when such an activity is detected, it is determined that there is the transketolase activity.

Also, in the present invention, the enhancement of the transaldolase activity of a transformant is confirmed when an increase in the value indicating the transaldolase activity in a cell extract of the transformant is detected.

Enhancement of Enzyme Activities of 3-dehydroquinate Synthase, 3-dehydroquinate Dehydratase, Shikimate Dehydrogenase, Shikimate Kinase, 5-enolpyruvylshikimate-3-phosphate (EPSP) Synthase, and Chorismate Synthase Further, in the transformant of the present invention, it is preferable that enzyme activities of one or more of enzymes on the shikimate pathway, after DAHP synthase, that is, 3-dehydroquinate synthase, 3-dehydroquinate dehydratase, shikimate dehydrogenase, shikimate kinase, 5-enolpyruvyl-shikimate-3-phosphate (EPSP) synthase, and chorismate synthase are enhanced, and still further, it is more preferable that enzyme activities of all of these are enhanced. Enhancement of enzyme activities of one or more of these promotes the metabolic conversion from DAHP to chorismate.

3-dehydroquinate synthase is an enzyme that catalyzes the conversion from DAHP to 3-dehydroquinic acid, 3-dehydroquinate dehydratase is an enzyme that catalyzes the conversion from 3-dehydroquinic acid to 3-dehydroshikimate, shikimate dehydrogenase is an enzyme that catalyzes the conversion from 3-dehydroshikimate to shikimate, shikimate kinase is an enzyme that catalyzes the conversion from shikimate to shikimate-3-phosphate, EPSP synthase is an enzyme that catalyzes the conversion from shikimate-3-phosphate to EPSP, and further, chorismate synthase is an enzyme that catalyzes the conversion from EPSP to chorismate.

3-dehydroquinate synthase, 3-dehydroquinate dehydratase, shikimate dehydrogenase, shikimate kinase, EPSP synthase, and chorismate synthase can be enhanced by introducing genes that encode these enzymes into a host microorganism, or by mutatate or base sequence substitution with respect to a regulatory sequence, a gene coding region, or both of each of the enzyme genes on a chromosome of a host microorganism. Among these, introducing an enzyme gene into a host microorganism so as to enhance activities of the enzyme that the gene encodes is convenient and efficient.

Though the origins of the genes to be introduced, encoding 3-dehydroquinate synthase, 3-dehydroquinate dehydratase, shikimate dehydrogenase, shikimate kinase, EPSP synthase, and chorismate synthase, are not limited particularly, genes of bacteria of the genus *Corynebacterium*, in particular, *Corynebacterium glutamicum*, are preferable in that they have good efficiency in the production of protocatechuic acid or a salt thereof.

As enzyme genes derived from *Corynebacterium glutamicum*, examples of the 3-dehydroquinate synthase gene include a DNA of SEQ ID NO: 153 (aroB), examples of the 3-dehydroquinate dehydratase gene include a DNA of SEQ ID NO: 5 (aroD), examples of the shikimate dehydrogenase gene include a DNA of SEQ ID NO: 6 (aroE), examples of the shikimate kinase gene include a DNA of SEQ ID NO: 154 (aroK), examples of the EPSP synthase gene include a DNA of SEQ ID NO: 155 (aroA), and examples of the chorismate synthase gene include a DNA of SEQ ID NO: 156 (aroC).

Further, in the present invention, a DNA which consists of a base sequence having 90% or more, preferably 95% or more, more preferably 98% or more of identity with any one of base sequences of SEQ ID NOs: 153, 5, 6, 154, 155, and 156, and encodes a polypeptide having 3-dehydroquinate synthase activity, 3-dehydroquinate dehydratase activity, shikimate dehydrogenase activity, shikimate kinase activity, EPSP synthase activity, or, chorismate synthase activity can be used as well.

Further, in the present invention, a DNA that hybridizes to a DNA which consists of a base sequence complementary to a base sequence of any one of SEQ ID NOs: 153, 5, 6, 154, 155, and 156 under stringent conditions, and encodes a polypeptide having 3-dehydroquinate synthase activity, 3-dehydroquinate dehydratase activity, shikimate dehydrogenase activity, shikimate kinase activity, EPSP synthase activity, or, chorismate synthase activity, can be used as well.

3-dehydroquinate synthase activity is measured according to a known method (Meudi, S. et al., Dehydroquinate synthase from *Escherichia coli*, and its substrate 3-deoxy-D-arabino-heptulosonic acid 7-phosphate. Methods. Enzymol. 142: 306-314 (1987)). More specifically, at 33° C., an enzyme solution to be tested is added to a reaction mixture solution composed of 50 mM potassium phosphate buffer (pH 7.0), 0.2 mM DAHP, 0.2 mM NAD$^+$, 1 mM Cobalt(II) chloride.6H$_2$O, and a crude enzyme solution of 3-dehydroquinate dehydratase, to allow the reaction to start. An increase in absorbance at 234 nm (absorption coefficient=12000/M·cm) in association with 3-dehydroshate generated by a coupling reaction of 3-dehydroquinate synthase activity and 3-dehydroquinate dehydratase activity is monitored with Beckman DU800 spectrophotometer, and the enzyme activity is calculated from the initial reaction rate. Activity of causing 1 μmol of 3-dehydroshikimate to be generated per one minute at 33° C. is assumed to be 1 unit of DHQ synthase activity, and when such an activity is detected, it is determined that there is the DHQ synthase activity.

Also, in the present invention, the enhancement of the 3-dehydroquinate synthase activity of a transformant is confirmed when an increase in the 3-dehydroquinate synthase activity in a cell extract of the transformant is detected.

3-dehydroquinate dehydratase activity is measured according to a known method (Chaudhuri, S. et al., 3-Dehydroquinate dehydratase from *Escherichia coli*. Methods. Enzymol. 142: 320-324 (1987)). More specifically, at 33° C., an enzyme solution to be tested is added to a reaction mixture solution composed of 50 mM potassium phosphate buffer (pH 7.0) and 0.5 mM 3-dehydroquinic acid, to allow the reaction to start. An increase in absorbance at 234 nm (absorption coefficient=12000/M·cm) in association with 3-dehydroshikate generated is monitored with Beckman DU800 spectrophotometer (manufactured by Beckman Coulter), and the enzyme activity is calculated from the initial reaction rate. Activity of causing 1 μmol of 3-dehydroshikate to be generated per one minute at 33° C. is assumed to be 1 unit of 3-dehydroquinate dehydratase activity, and when such an activity is detected, it is determined that there is the 3-dehydroquinate dehydratase activity.

Also, in the present invention, the enhancement of the 3-dehydroquinate dehydratase activity of a transformant is confirmed when an increase in the 3-dehydroquinate dehydratase activity in a cell extract of the transformant is detected.

The shikimate dehydrogenase activity is measured by a known method (Chaudhuri, S. et al., Shikimate dehydratase from *Escherichia coli*. Methods. Enzymol. 142: 315-320 (1987)). More specifically, at 33° C., an enzyme solution to be tested is added to a reaction mixture solution composed of 100 mM tris-HCl buffer (pH 7.5), 0.2 mM NADPH, and 0.5 mM 3-dehydroshikimate to allow the reaction to start, and a decrease in the absorbance at 340 nm in association with the consumption of NADPH (=6220/M·cm) is monitored with a Beckman DU800 spectrophotometer (manufactured by Beckman Coulter), so that the enzyme activity is calculated based on the initial reaction rate. Activity that causes 1 μmol of NADPH to be consumed per minute at 33° C. is assumed to be 1 unit of shikimate dehydrogenase activity. When such an activity is detected, it is determined that there is the shikimate dehydrogenase activity.

Also, in the present invention, the enhancement of the shikimate dehydrogenase activity of a transformant is confirmed when an increase in the shikimate dehydrogenase activity in a cell extract of the transformant is detected.

The shikimate kinase activity is measured by a known method (Cheng, W C. et al., Structures of *Helicobacter pylori* shikimate kinase reveal a selective inhibitor-induced-fit mechanism. PLos One. 7: e33481 (2012)). More specifically, at 33° C., an enzyme solution to be tested is added to a reaction mixture solution containing a 100 mM tris-HCl buffer (pH 7.5), 50 mM KCL, and 5 mM $MgCl_2$, 1.6 mM shikimate, 2.5 mM ATP, 1 mM phosphoenolpyruvate, 0.1 mM NADH, 2.5 U/ml pyruvate kinase, 2.7 U/ml lactate dehydrogenase to allow the reaction to start. The production of ADP by shikimate kinase activity is conjugated with reactions by pyruvate kinase and lactate dehydrogenase, and the decrease in the absorbance at 340 nm in association with the oxidation of NADH (=6220/M·cm), which occurs as a result, is monitored with a Beckman DU800 spectrophotometer (manufactured by Beckman Coulter). The enzyme activity is calculated based on the initial reaction rate. Activity of causing 1 μmol of NADH to be oxidized per minute at 33° C. is assumed to be 1 unit of shikimate kinase activity. When such an activity is detected, it is determined that there is the shikimate kinase activity.

Also, in the present invention, the enhancement of the shikimate kinase activity of a transformant is confirmed when an increase in the shikimate kinase activity in a cell extract of the transformant is detected.

The EPSP synthase activity is measured in the following manner. More specifically, at 33° C., an enzyme solution to be tested is added to a reaction mixture solution composed of 100 mM tris-HCl buffer (pH 7.5), 5 mM $MgCl_2$, 0.5 mM shikimate-3-phosphate, 0.5 mM phosphoenolpyruvate sodium to allow the reaction to start, and a decrease in the absorbance at 232 nm (absorption coefficient=2800/M·cm) in association with PEP is monitored with Beckman DU800 spectrophotometer (manufactured by Beckman Coulter), so that the enzyme activity is calculated from an initial reaction rate. Activity of causing 1 μmol of phosphoenolpyruvate to be consumed per one minute at 33° C. is assumed to be one unit of EPSP synthase activity, and when such an activity is detected, it is determined that there is the EPSP synthase activity.

Also, in the present invention, the enhancement of the EPSP synthase activity of a transformant is confirmed when an increase in the EPSP synthase activity in a cell extract of the transformant is detected.

The chorismate synthase activity is measured by a known method (Kitzing, K. et al., Spectroscopic and Kinetic Characterization of the Bifunctional Chorismate Synthase from *Neurospora crassa*. J. Biol. Chem. 276: 42658-42666 (2001)). More specifically, the measurement is performed as follows: at 37° C., an enzyme solution to be tested is added to a reaction mixture solution composed of 100 mM potassium phosphate buffer (pH 7.6), 4 mM $MgSO_4$, 10 mM glutamine, 30 mM sulfuric acid ammonium, 1 mM DTT, 0.01 mM FMN, 0.08 mM EPSP, and a crude enzyme solution of anthranilate synthase, so as to allow the reaction to start; fluorescence of 390 nm, which indicates the production of anthranilate acid, which is generated by a coupling reaction with anthranilate synthase, is monitored by F-2500 Fluorescence Spectrophotometer (manufactured by Hitachi, Ltd.), so that the enzyme activity is calculated from an initial reaction rate. The reduction of FMN is performed by adding 5 mM dithionite or 1 mM NADPH. Activity of causing 1 μmol of anthranilic acid to be generated per one minute at 37° C. is assumed to be one unit of chorismate synthase activity, and when such an enzyme activity is detected, it is determined that there is the chorismate synthase activity.

Also, in the present invention, the enhancement of the chorismate synthase activity of a transformant is confirmed when an increase in the chorismate synthase activity in a cell extract of the transformant is detected.

Elimination, Inhibition, and Reduction of Protocatechuic Acid-3,4-dioxygenase Activity Regarding the transformant of the present invention, its protocatechuic acid-3,4-dioxygenase activity preferably disappears, is inhibited, or decreases.

Protocatechuic acid-3,4-dioxygenase is an enzyme that catalyzes the conversion into β-carboxy-cis,cis-muconic acid caused by ring-opening of protocatechuic acid on the catabolic pathway of protocatechuic acid. The protocatechuic acid-3,4-dioxygenase activity can be eliminated, inhibited, or reduced by disruption, deletion, or mutation of a protocatechuic acid-3,4-dioxygenase gene on a chromosome.

Examples of the protocatechuic acid-3,4-dioxygenase gene of *Corynebacterium glutamicum* include pcaHG.

In the present invention, the elimination, inhibition, or reduction of protocatechuic acid-3,4-dioxygenase activity of a transformant is confirmed in the following manner: protocatechuic acid-3,4-dioxygenase activity in a cell extract of the transformant is measured, and when the enzyme activity is determined to have decreased or disappeared, the elimination, inhibition, or reduction of the enzyme activity is confirmed.

The protocatechuic acid-3,4-dioxygenase activity is measured in the following manner: at 33° C., an enzyme solution to be tested is added to a reaction mixture solution composed of 100 mM tris-HCl buffer (pH 7.5) and 1 mM protocatechuic acid to allow the reaction to start, and a decrease in the absorbance at 290 nm (absorption coefficient=2800/M·cm) in association with protocatechuic acid is monitored with a Beckman DU800 spectrophotometer (manufactured by Beckman Coulter), so that an enzyme activity is calculated from an initial reaction rate. Activity of causing 1 μmol of protocatechuic acid to disappear per minute at 33° C. is assumed to be 1 unit of protocatechuic acid-3,4-dioxygenase activity. When such an enzyme activity is detected, it is determined that there is the protocatechuic acid-3,4-dioxygenase activity.

Elimination, Inhibition, and Reduction of Intracellular Saccharide Uptake Via Phosphotransferase System (PTS)

The phosphoenolpyruvate: saccharide phosphotransferase system (PTS) is a saccharide transport mechanism present only in prokaryotes and involved in saccharide (e.g., glucose) uptake coupled to saccharide phosphorylation. In *Escherichia coli* and a coryneform bacterium, PTS plays a major role in intracellular saccharide uptake. PTS is composed of Enzyme I (PEP protein kinase) and HPr (histidine-phosphorylatable protein), which are common components, and of Enzyme II, which is a membrane protein involved in saccharide-specific transport. Using phosphoenolpyruvate (PEP) from the glycolytic system as a phosphate donor, PTS converts saccharides, through phosphorelay between these components, into their phosphorylated forms and transports them into cells. However, in association with the intracellular transport of glucose, PTS consumes PEP, which is one of the common precursors of aromatic compounds, as a phosphate-donating group for generating glucose-6-phosphate. PEP is a precursor compound that plays a key role in the production of aromatic compounds, and in order to mass-produce aromatic compounds including protocatechuic acid, it is important to suppress the consumption of PEP by a conflict metabolic pathway such as PTS, and to increase the availability of PEP to the aromatic compound production pathway. In the transformant of the present invention, it is preferable that the saccharide uptake via PTS is inactivated, and simultaneously, saccharide availability via a saccharide transport system (non-PTS saccharide transport system) that does not consume PEP in association with saccharide transport and that is different from PTS is provided.

The PTS-mediated intracellular saccharide uptake can be eliminated, inhibited, or reduced by disruption, deletion, or mutation of genes encoding PTS on the chromosome of a coryneform bacterium.

Examples of the gene that encodes PTS include ptsI encoding Enzyme I, ptsH encoding Hpr, and ptsG encoding Enzyme II. In order to inhibit PTS-dependent glucose transport, one or more of these genes may be disrupted, deleted, or mutated. It is preferred that the ptsH gene encoding the Hpr protein, which is a common component in PTS, is disrupted, deleted, or mutated.

Replacement of a gene on the chromosome with the corresponding gene having a disruption or deletion can be achieved by creating a gene with deletion mutation for not producing a normally functioning protein, and transforming a bacterium with a DNA which consists of the mutated gene for homologous recombination between the gene on the chromosome and the mutated gene. A protein encoded by a gene having a disruption or deletion, even when produced, has a conformation different from that of the wild type, and has no or reduced function. The gene deletion or gene disruption by way of gene substitution through the use of homologous recombination has already been established, and examples thereof include a method using a plasmid containing a temperature sensitive replication origin or a plasmid capable of conjugal transfer, and a method using a suicide vector not having a replication origin in a host (U.S. Pat. No. 6,303,383, JP-A-05(1993)-007491).

In the present invention, the elimination, inhibition, or reduction of the PTS-mediated saccharide transport activity of a coryneform bacterium transformant is confirmed based on the fact that the growth of the transformant using, as carbon source, the saccharide (glucose, sucrose, fructose, etc.) transported by PTS is eliminated, inhibited, or reduced and on the fact that introducing a normal pts gene restores the phenotype to normal.

Enhancement of Saccharide Uptake Activity Mediated by Non-PTS Saccharide Transport System In *Corynebacterium glutamicum*, there exists a non-PTS glucose transport system that is different from PTS and that does not consume PEP in association with the intracellular saccharide transport. A *Corynebacterium glutamicum* strain of which the pts gene is disrupted, and PTS-mediated saccharide uptake is thereby inhibited exhibits no or significantly reduced growth on glucose as a single carbon source, but higher expression of non-PTS glucose transporter and glucokinase in the strain restores the ability of the strain growing on glucose as a single carbon source. (Ikeda, M., et al., Identification and application of a different glucose uptake system that functions as an alternative to the phosphotransferase system in *Corynebacterium glutamicum*. Appl. Microbiol. Biotechnol. 90: 1443-1451, Lindner, S. N., et al., Phosphotransferase system-independent glucose utilization in *Corynebacterium glutamicum* by inositol permeases and glucokinases. Appl. Environ. Microbiol. 77: 3571-3581).

In the present invention, it is desirable that intracellular glucose uptake and bacterial growth on glucose as a carbon source are improved by the enhancement of the non-PTS glucose transporter activity and the glucokinase activity in a *Corynebacterium glutamicum* strain in which PTS-mediated saccharide transport is blocked. This is considered to make it possible to avoid the consumption of PEP in association with glucose transport, and to provide more PEP for the biosynthesis of aromatic compounds, such as shikimate.

The intracellular glucose uptake depending on non-PTS glucose transporter can be enhanced by introduction of a gene encoding a non-PTS glucose transporter, or mutatate into or base sequence substitution in (the control sequence or the gene coding region of) a chromosomal non-PTS glucose transporter gene of a coryneform bacterium, leading to increase in the expression amount of the gene or increase in the activity of the product of the gene.

Among these, enhancement of the glucose uptake activity by introduction of a non-PTS glucose transporter gene is convenient and efficient.

The origin of the non-PTS glucose transporter gene to be introduced is not particularly limited, but in terms of shikimate productivity, the genus *Corynebacterium*, in particular, *Corynebacterium glutamicum* is preferred.

The non-PTS glucose transporter may be of any type as long as it can function in a coryneform bacterium, and examples thereof include inositol transporters derived from *Corynebacterium glutamicum* (IoIT1, IoIT2), galactose permease derived from *Escherichia coli* (GalP), and glucose facilitator derived from *Zymomonas mobilis* (Glf). Particularly, for better efficiency in the production of shikimate, preferred is that the saccharide uptake activity mediated by an inositol transporter of *Corynebacterium glutamicum* is enhanced.

Examples of the inositol transporter gene derived from *Corynebacterium glutamicum* include the DNA which consists of the base sequence of SEQ ID NO: 157 (IoIT1).

Further, in the present invention, a DNA which consists of a base sequence having 90% or more, in particular 95% or more, in particular 98% or more of identity with the base sequence of SEQ ID NO: 157 and which encodes a polypeptide having inositol transporter activity can also be used.

Still further, in the present invention, a DNA that hybridizes to a DNA which consists of a base sequence complementary to a base sequence of SEQ ID NO: 159 under stringent conditions and which encodes a polypeptide having inositol transporter activity can also be used.

In the present invention, a protein encoded by a DNA is identified as a non-PTS glucose permease, based on the facts, as indicators, that a transformant produced by introducing the DNA into a host cell for expression of the DNA in the cell, the host cell having lost its PTS-dependent glucose transport ability as a result of ptsH gene disruption or the like and showing reduced growth using glucose as a carbon source, can grow on glucose as a carbon source in an enhanced manner or consumes glucose at a higher rate, as compared to the cell before the transformation, and that the effect is not affected by inhibition of PTS-dependent saccharide transport by, for example, disruption of a pts gene.

Also, in the present invention, the enhancement of the non-PTS glucose transporter activity of a transformant is confirmed by the fact, as an indicator, that the transformant that has lost the PTS-dependent saccharide transport can grow using glucose as a carbon source or consumes glucose at a higher rate, as compared to the transformant before the gene introduction.

Enhancement of Glucokinase Activity

In order for the glucose taken into cells by non-PTS glucose transporter to be metabolized in the central metabolic system, it needs to be converted to glucose-6-phosphate by glucokinase. Glucokinase is an enzyme that catalyzes the conversion from glucose to glucose-6-phosphate.

In the present invention, preferably, along with the enhancement of glucose transport depending on non-PTS glucose transporter, glucokinase activity is also enhanced. As a result, the present invention is characterized in that intracellular uptake of glucose and subsequent saccharide metabolism in the glycolytic system and in the pentose phosphate pathway are promoted.

The glucokinase activity can be enhanced by introduction of a glucokinase gene for enhancement of the expression thereof, or mutatate into or sequence substitution in (the control sequence or in the gene coding region of) a chromosomal glucokinase gene, leading to increase in the expression amount of the gene or increase in the activity of the product of the gene.

On the chromosome of *Corynebacterium glutamicum* R, there exist at least three kinds of glucokinase genes, namely cgR_2067 (glk1), cgR_2552 (glk2), and cgR_1739 (ppgK). Among these, cgR_2067 (glk1) and cgR_2552 (glk2) have high homology with a glucokinase which uses ATP as a good substrate, and cgR_1739 (ppgK) has high homology with a glucokinase which uses polyphosphate as a good substrate. In the present invention, preferred is that one or more kinds of these glucokinase genes are enhanced, and more preferred is that all of the three kinds are enhanced.

The enhancement of the glucokinase activity by introduction of the glucokinase gene is convenient and efficient.

The origin of the glucokinase gene to be introduced is not particularly limited, but in terms of shikimate productivity, the genus *Corynebacterium*, in particular, *Corynebacterium glutamicum* is preferred.

Examples of the glucokinase gene of *Corynebacterium glutamicum* include the DNAs that consist of base sequences of SEQ ID NOs: 158, 159, and 160, respectively (corresponding to glk1, glk2, or ppgK, respectively).

In the present invention, a DNA which consists of a base sequence having 90% or more, in particular 95% or more, in particular 98% or more of identity with the base sequence of SEQ ID NOs: 158, 159, or 160 and which encodes a polypeptide having glucokinase activity can also be used.

In the present invention, a DNA that hybridizes to a DNA which consists of a base sequence complementary to a base sequence of any one of SEQ ID NOs: 158, 159, or 160 under stringent conditions and which encodes a polypeptide having glucokinase activity can also be used.

In the present invention, to identify a protein encoded by a DNA as glucokinase, the protein encoded by the DNA is measured for glucokinase activity. For the measurement of glucokinase activity, an enzyme solution to be tested is added to a reaction mixture solution containing a 100 mM tris-HCl buffer (pH 7.5), 4 mM magnesium chloride, 1 mM ATP, 0.2 mM NADP$^+$, 20 mM glucose, and 1 U glucose-6-phosphate dehydrogenase at 33° C. to allow the reaction to start, and the absorbance at 340 nm showing the production of NADPH (=6220/M·cm) is monitored with a Beckman DU800 spectrophotometer (manufactured by Beckman Coulter). Activity of causing 1 μmol of NADPH to be produced per minute at 33° C. is assumed to be 1 unit of glucokinase activity.

Also, in the present invention, the enhancement of the glucokinase activity of a transformant is confirmed by measuring the glucokinase activity in a cell extract of the transformant.

Enhancement of Glyceraldehyde 3-phosphate Dehydrogenase (GAPDH) Activity

GAPDH is an enzyme that converts glyceraldehyde-3-phosphate into 1,3-bisphosphoglycerate.

In the transformant of the present invention, the GAPDH activity is preferably enhanced.

In the present invention, a coryneform bacterium transformant in which a pts gene was disrupted and the non-PTS glucose transporter-mediated saccharide uptake and the glucokinase activity were enhanced exhibited significant accumulation of dihydroxyacetone (DHA) and glycerol; DHA is a metabolite produced, during culture and reaction, by dephosphorization of dihydroxyacetone phosphate as a metabolic intermediate in the glycolytic system, and glycerol is generated by further metabolization of DHA. Also, in the transformant, the intracellular concentrations of glyceraldehyde-3-phosphate and other upstream metabolic intermediates in the glycolytic pathway were remarkably increased. These phenomena indicate that the reaction step catalyzed by GAPDH was the rate-limiting step of the saccharide metabolism in the glycolytic system in the transformant. The increased expression of GAPDH in the transformant promotes saccharide consumption, which leads to increased production of target products. The inventors of the present invention found these.

It is therefore desirable in the present invention that enhanced GAPDH activity in the transformant releases the rate limitation in the saccharide metabolism to promote saccharide consumption and to improve protocatechuic acid production ability.

The GAPDH activity can be enhanced by introduction of a GAPDH gene for enhancement of the expression thereof, or mutatate into or sequence substitution in (the control sequence or in the gene coding region of) a chromosomal GAPDH gene, leading to increase in the expression amount of the gene or increase in the activity of the product of the gene.

Among these, enhancement of the GAPDH activity by introduction of the GAPDH gene is convenient and efficient The origin of the GAPDH gene to be introduced is not particularly limited, but in terms of protocatechuic acid production ability, the GAPDH gene is preferably a gene of a bacterium of the genus Corynebacterium, in particular, a gene of Corynebacterium glutamicum.

Examples of the GAPDH gene of Corynebacterium glutamicum include the DNA which consists of a base sequence of SEQ ID NO: 161 (gapA).

In the present invention, a DNA which consists of a base sequence having 90% or more, in particular 95% or more, in particular 98% or more of identity with the base sequence of SEQ ID NO: 161 and which encodes a polypeptide having GAPDH activity can also be used.

Further, in the present invention, a DNA that hybridizes to a DNA which consists of a base sequence complementary to a base sequence of SEQ ID NO: 161 under stringent conditions and which encodes a polypeptide having GAPDH activity can also be used.

In the present invention, to identify a protein encoded by a DNA as GAPDH, the polypeptide encoded by the DNA is measured for GAPDH activity. For the measurement of the GAPDH activity, an enzyme solution to be tested is added to a reaction mixture solution containing a 25 mM phosphate buffer (pH 7.5), 25 mM triethanolamine (pH 7.5), 0.2 mM EDTA, 5 mM NAD$^+$, and 5 mM glyceraldehyde-3-phosphate at 33° C. to allow the reaction to start, and the absorbance at 340 nm showing the production of NADH (=6220/M·cm) is monitored with a Beckman DU800 spectrophotometer (manufactured by Beckman Coulter). Activity of causing 1 µmol of NADH to be generated per minute at 33° C. is assumed to be 1 unit of GAPDH activity.

Also, in the present invention, the enhancement of the GAPDH activity of a coryneform bacterium transformant is confirmed by measuring the GAPDH activity in a cell extract of the coryneform bacterium transformant.

Elimination, Inhibition, or Reduction of Dihydroxyacetone Phosphate (DHAP) Phosphatase Activity DHAP phosphatase is an enzyme that catalyzes the dephosphorization of DHAP, which converts DHAP to dihydroxyacetone (DHA).

In the transformant of the present invention, the DHAP phosphatase activity is preferably eliminated, inhibited, or reduced. As described above, a coryneform bacterium which depends for intracellular saccharide uptake on highly expressed non-PTS glucose transporter and glucokinase highly produces DHA as a by-product. Blocking the DHA pathway therefore makes it possible to supply more carbon for the production of aromatic compounds, such as protocatechuic acid.

Corynebacterium glutamicum has HAD (haloacid dehalogenase) super family phosphatase (HdpA) as an enzyme that catalyzes the dephosphorization of DHAP (Jojima, T. et. al., Identification of a HAD superfamily phosphatase, HdpA, involved in 1,3-dihydroxyacetone production during sugar catabolism in Corynebacterium glutamicum. FEBS. Lett. 586: 4228-4232 (2012)). The DHAP phosphatase activity of Corynebacterium glutamicum can be eliminated, inhibited, or reduced by disruption, deletion, or mutation of the DHAP phosphatase gene (hdpA) on the chromosome.

Further, in the present invention, the elimination, inhibition, or reduction of the DHAP phosphatase activity of a transformant is confirmed by measuring the DHAP phosphatase activity in a cell extract of the transformant. For the measurement of the DHAP phosphatase activity, an enzyme solution is added to a reaction mixture solution containing a 100 mM tris-malate buffer (pH 7.5), 5 mM magnesium sulfate, and 5 mM DHAP at 33° C. to allow the reaction to start, and inorganic phosphate ions released from DHAP were quantified by a known colorimetric method (Gawronski, J. D., et al., Microtiter assay for glutamine synthetase biosynthetic activity using inorganic phosphate detection. Anal. Biochem. 327: 114-118 (2004)). Anal. Biochem. 327: 114-118 (2004)). In a case where the quantitative value decreases or turns to zero, the dihydroxyacetone phosphate phosphatase activity is judged to have been eliminated, inhibited or reduced.

Construction of Vector for Transformant Construction

When gene introduction into a host microorganism is performed to enhance the activity of a protein or an enzyme encoded by the gene, the DNA that encodes the protein or the gene may be integrated into the chromosome of a host or be cloned into a suitable vector replicable in a host and then introduced into the host.

The plasmid vector may be any plasmid vector as long as it comprises a gene responsible for autonomously replicating function in a coryneform bacterium. Specific examples of the plasmid vector include pAM330 of Brevibacterium lactofermentum 2256 (JP-A-58-67699; Miwa, K. et al., Cryptic plasmids in glutamic acid-producing bacteria. Agric. Biol. Chem. 48: 2901-2903 (1984); and Yamaguchi, R. et al., Determination of the complete nucleotide sequence of the Brevibacterium lactofermentum plasmid pAM 330 and the analysis of its genetic information. Nucleic Acids Symp. Ser. 16: 265-267 (1985)), pHM1519 of Corynebacterium glutamicum ATCC3058 (Miwa, K. et al., Cryptic plasmids in glutamic acid-producing bacteria. Agric. Biol. Chem. 48:2901-2903 (1984)), pCRY30 of the same Corynebacterium glutamicum ATCC3058 (Kurusu, Y. et al., Identification of plasmid partition function in coryneform bacteria. Appl. Environ. Microbiol. 57: 759-764 (1991)), pCG4 of Corynebacterium glutamicum T250 (JP-A-57-183799; and Katsumata, R. et al., Protoplast transformation of glutamate-producing bacteria with plasmid DNA. J. Bacteriol., 159: 306-311 (1984)), pAG1, pAG3, pAG14, and pAG50 of the same Corynebacterium glutamicum T250 (JP-A-62-166890), pEKO, pEC5, and pEKEx1 of the same Corynebacterium glutamicum T250 (Eikmanns, B. J. et al., A family of Corynebacterium glutamicum/Escherichia coli shuttle vectors for cloning, controlled, gene expression, and promoter probing. Gene, 102: 93-98 (1991)), etc.

Examples of a preferred promoter include promoter PgapA as a promoter of the glyceraldehyde-3-phosphate dehydrogenase A gene (gapA), promoter Pmdh as a promoter of the malate dehydrogenase gene (mdh), and promoter PldhA as a promoter of lactate dehydrogenase A gene (ldhA), all of which are of Corynebacterium glutamicum R, and inter alia, PgapA is preferred.

Examples of a preferred terminator include terminator rrnB T1T2 of Escherichia coli rRNA operon, terminator trpA of Escherichia coli, and terminator trp of Brevibacterium lactofermentum, and inter alia, terminator rrnB T1T2 is preferred.

Transformation

As a method of transformation, any publicly known method can be used without limitation. Examples of such a known method include the calcium chloride/rubidium chloride method, the calcium phosphate method, DEAE-dextran transfection, and the electric pulse method. Inter alia, preferred for a coryneform bacterium is the electric pulse method, which can be performed by a known method (Kurusu, Y. et al., Electroporation-transformation system for Coryneform bacteria by auxotrophic complementation. Agric. Biol. Chem. 54: 443-447 (1990)).

The transformant is cultured using a culture medium usually used for culture of microorganisms. The culture medium may be a natural or synthetic medium containing a carbon source, a nitrogen source, inorganic salts, other nutritional substances, etc. Examples of the carbon source include saccharides and saccharide alcohols such as glucose, fructose, sucrose, mannose, maltose, mannitol, xylose, arabinose, galactose, starch, molasses, sorbitol and glycerol; organic acids such as acetic acid, citric acid, lactic acid, fumaric acid, maleic acid and gluconic acid; and alcohols such as ethanol and propanol. These carbon sources may be used alone or as a mixture of two or more thereof. The concentration of these carbon sources in the culture medium is usually about 0.1 to 10 w/v %.

Examples of the nitrogen source include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. These nitrogen sources may be used alone or as a mixture of two or more thereof. The concentration of these nitrogen sources in the culture medium varies depending on the kind of the nitrogen compound, but is usually about 0.1 to 10 w/v %.

Examples of the inorganic salts include potassium dihydrogen phosphate, dipotassium hydrogen phosphate, magnesium sulfate, sodium chloride, iron (II) nitrate, manganese sulfate, zinc sulfate, cobalt sulfate, and calcium carbonate. These inorganic salts may be used alone or as a mixture of two or more thereof. The concentration of the inorganic salts in the culture medium varies depending on the kind of the inorganic salts, but is usually about 0.01 to 1 w/v %.

Examples of the nutritional substances include meat extract, peptone, polypeptone, yeast extract, dry yeast, corn steep liquor, skim milk powder, defatted soybean hydrochloric acid hydrolysate, and extract from animals, plants or microorganisms, and degradation products thereof. The concentration thereof is usually about 0.1 to 10 w/v %. Further, vitamins may be added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Examples of the preferable microbial culture medium include A-medium [Inui, M. et al., Metabolic analysis of *Corynebacterium glutamicum* during lactate and succinate productions under oxygen deprivation conditions. J. Mol. Microbiol. Biotechnol. 7:182-196 (2004)], BT-medium [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)], etc.

The culture temperature may be about 15 to 45° C., and the culture period may be about 1 to 7 days.

(2) Method of Producing Protocatechuic Acid or a Salt Thereof

Protocatechuic acid or a salt thereof can be produced by a method that includes a step of culturing, or causing reaction of, the above-described transformant of the present invention in a reaction solution containing a saccharide, so as to cause the transformant to produce the protocatechuic acid or the salt thereof.

Glucose is preferred as the saccharide, but other saccharides that are metabolized into glucose can also be used, in addition to monosaccharides such as fructose, mannose, arabinose, xylose, and galactose. Such saccharides include oligosaccharides and polysaccharides that have a glucose unit. Examples of such saccharides include disaccharides, such as cellobiose, sucrose, lactose, maltose, trehalose, cellobiose, and xylobiose; polysaccharides, such as dextrin and soluble starch; etc.

Also, molasses, which contains these starting compounds, can also be used, for example. In addition, a saccharified solution which is obtainable by saccharifying, using a diastatic enzyme, non-edible agricultural waste including straw (rice straw, barley straw, wheat straw, rye straw, oat straw, etc.), bagasse, and corn stover; energy crops including switchgrass, napier grass, and *Miscanthus*; wood waste; waste paper; etc. and which contains two or more kinds of saccharides, including glucose, can also be used.

Growth of Microorganism

Before the culture in a medium containing a saccharide, that is, the reaction, the transformant is preferably cultured and grown under aerobic conditions at about 25 to 38° C. for about 12 to 48 hours.

Culture Medium

The culture medium used for aerobic culture of the transformant before the reaction may be a natural medium or a synthetic medium containing a carbon source, a nitrogen source, inorganic salts, other nutritional substances, etc.

Examples of the carbon source that can be used include saccharides (monosaccharides such as glucose, fructose, mannose, xylose, arabinose, and galactose; disaccharides such as sucrose, maltose, lactose, cellobiose, xylobiose, and trehalose; polysaccharides such as starch; and molasses); saccharide alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin.

Only one kind of these carbon sources or a mixture of two or more kinds may be used.

Examples of the nitrogen source that can be used Include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. Only one kind of these nitrogen sources or a mixture of two or more kinds may be used. The concentration of these nitrogen sources in the culture medium varies depending on the kind of the nitrogen compound, but is usually about 0.1 to 10 w/v %.

Examples of the inorganic salts include potassium dihydrogenphosphate, dipotassium hydrogenphosphate, magnesium sulfate, sodium chloride, iron (II) nitrate, manganese sulfate, zinc sulfate, cobalt sulfate, and calcium carbonate. Only one kind of these inorganic salts or a mixture of two or more kinds may be used. The concentration of the inorganic salts in the culture medium varies depending on the kind of the inorganic salts, but is usually about 0.01 to 1 w/v %.

Examples of the nutritional substances include meat extract, peptone, poly peptone, yeast extract, dry yeast, corn steep liquor, skim milk powder, defatted soybean hydrochloric acid hydrolysate, and extract from animals, plants or microorganisms, and degradation products thereof. The concentration of the nutritional substances in the culture medium varies depending on the kind of the nutritional substances, but is usually about 0.1 to 10 w/v %.

Further, vitamins maybe added as needed. Examples of the vitamins include biotin, thiamine (vitamin B1), pyridoxine (vitamin B6), pantothenic acid, inositol, nicotinic acid, etc.

The pH of the culture medium is preferably about 6 to 8.

Specific examples of the preferable culture medium for coryneform bacteria include A-medium [Inui, M. et al., Metabolic analysis of *Corynebacterium glutamicum* during lactate and succinate productions under oxygen deprivation conditions. J. Mol. Microbiol. Biotechnol. 7:182-196 (2004)], BT-medium [Omumasaba, C. A. et al., *Corynebacterium glutamicum* glyceraldehyde-3-phosphate dehydrogenase isoforms with opposite, ATP-dependent regulation. J. Mol. Microbiol. Biotechnol. 8:91-103 (2004)], etc. Such a culture medium can be used after prepared so as to contain a saccharide at a concentration in the above-mentioned range.

Culture Solution or Reaction Solution

The culture solution or reaction solution may be a natural or synthetic reaction solution containing a carbon source, a nitrogen source, inorganic salts, etc.

The carbon source used may be saccharide described above, or a molasses or a saccharified solution containing such compounds. As the carbon source, besides saccharides, saccharide alcohols such as mannitol, sorbitol, xylitol, and glycerol; organic acids such as acetic acid, citric acid, lactic acid, fumaric acid, maleic acid and gluconic acid; alcohols such as ethanol and propanol; and hydrocarbons such as normal paraffin can also be used.

Only one kind of these carbon sources or a mixture of two or more kinds may be used.

The concentration of saccharides as the starting compound in the reaction solution is preferably about 1 to 20 w/v %, more preferably about 2 to 10 w/v %, and still more preferably about 2 to 5 w/v %.

The total concentration of the carbon sources including saccharides as raw materials in the reaction solution may be usually about 2 to 5 w/v %.

Examples of the nitrogen source that can be used include inorganic or organic ammonium compounds, such as ammonium chloride, ammonium sulfate, ammonium nitrate, and ammonium acetate; urea; aqueous ammonia; sodium nitrate; and potassium nitrate. Nitrogen-containing organic compounds, such as corn steep liquor, meat extract, peptone, N—Z-amine, protein hydrolysate, amino acid, etc. may also be used. Only one kind of these nitrogen sources or a mixture of two or more kinds may be used. The concentration of these nitrogen sources in the reaction solution varies depending on the kind of the nitrogen compound, but is usually about 0.1 to 10 w/v %.

Examples of the inorganic salts include potassium dihydrogen phosphate, dipotassium hydrogenphosphate, magnesium sulfate, sodium chloride, iron (II) nitrate, manganese sulfate, zinc sulfate, cobalt sulfate, and calcium carbonate. Only one kind of these inorganic salts or a mixture of two or more finds may be used. The concentration of the inorganic salts in the reaction solution varies depending on the kind of the inorganic salts, but is usually about 0.01 to 1 w/v %.

Further, vitamins maybe added as needed. Examples of the vitamins include biotin, thiamine (vitamin B1), pyridoxine (vitamin B6), pantothenic acid, inositol, nicotinic acid, etc.

The pH of the reaction solution is preferably about 6 to 8.

Specific examples of the preferable reaction solution for coryneform bacteria include the above-mentioned BT-medium, etc. Such a culture medium can be used after prepared so as to contain a saccharide at a concentration in the above-mentioned range.

Culturing Conditions or Reaction Conditions

The reaction temperature or the reaction temperature, that is, the temperature for keeping the transformant alive during the reaction is preferably about 20 to 50° C., and more preferably about 25 to 47° C. When the temperature is in the above range, protocatechuic acid can be efficiently produced.

The culture period or the reaction period is preferably about 1 to 7 days, and more preferably about 1 to 3 days.

The culture may be a batch process, a fed-batch process, or a continuous process. Among them, a batch process is preferred.

The reaction may be performed under aerobic conditions or reducing conditions. The ability of the transformant itself of the present invention for producing protocatechuic acid or a salt thereof is higher under aerobic conditions. However, aerobic conditions favor the growth of the transformant and the starting compound is consumed for the growth. Accordingly, the efficiency in the production of protocatechuic acid or a salt thereof is lowered.

It is therefore preferred that the reaction is performed under conditions that are aerobic and under which the transformant does not grow. In the present invention, "does not grow" includes "substantially does not grow" and "hardly grows". For example, growth of the transformant can be avoided or inhibited by the use of a reaction solution in which one or more of compounds essential for the growth of the microorganism, for example, vitamins, such as biotin and thiamine, nitrogen sources, amino acids essential for the growth of an auxotrophic transformant, etc., is depleted or limited.

Under reducing conditions, coryneform bacteria substantially do not grow, and therefore, the starting compound is not consumed for the growth, which leads to a higher production efficiency for producing protocatechuic acid or a salt thereof.

The "reducing conditions" is defined based on the oxidation-reduction potential of the reaction solution. The oxidation-reduction potential of the reaction solution is preferably about −200 mV to −500 mV, and more preferably about −150 mV to −500 mV.

The reducing conditions of the reaction solution can be simply estimated using resazurin indicator (in reducing conditions, decolorization from blue to colorless is observed). However, for precise measurement, a redox-potential meter (for example, ORP Electrodes made by BROADLEY JAMES) is used.

As a method of preparing a culture solution or a reaction solution under reducing conditions, any publicly known method can be used without limitation. For example, as a liquid medium for preparation of the reaction solution, an aqueous solution for a reaction solution may be used instead of distilled water or the like. As reference for preparation of the aqueous solution for a reaction solution, for example, the method for preparing a culture medium for strictly anaerobic microorganisms, such as sulfate-reducing microorganisms (Pfennig, N. et al.: "The dissimilatory sulfate-reducing bacteria, in The Prokaryotes, A Handbook on Habitats, Isolation and Identification of Bacteria", Ed. by Starr, M. P. et al. Berlin, Springer Verlag, 926-940, 1981, and "Nogeikagaku Jikkensho" Ed. by Kyoto Daigaku Hogakubu Nogeikagaku Kyoshitsu, Vol. 3, Sangyo Tosho, 1990, Issue 26) may be used, and such a method provides an aqueous solution under desired reducing conditions.

Specifically, by treating distilled water or the like with heat or under reduced pressure for removal of dissolved gases, an aqueous solution for a reaction solution under reducing conditions can be obtained. In this case, for removal of dissolved gases, especially dissolved oxygen, distilled water or the like may be treated under reduced pressure of about 10 mmHg or less, preferably about 5 mmHg or less, more preferably about 3 mmHg or less, for about 1 to 60 minutes, preferably for about 5 to 40 minutes, whereby an aqueous solution for a reaction solution under reducing conditions can be obtained.

Alternatively, by adding a suitable reducing agent (for example, thioglycolic acid, ascorbic acid, cysteine hydrochloride, mercaptoacetic acid, thiol acetic acid, glutathione, sodium sulfide, etc.), an aqueous solution for a reaction solution under reducing conditions can be prepared.

These methods may be suitably combined to prepare an effective aqueous solution for a reaction solution under reducing conditions.

In the case of a reaction under reducing conditions, it is preferred to maintain the reducing conditions of the reaction solution during the reaction. For maintenance of reducing conditions, it is desirable that oxygen from the outside of the reaction system is prevented to the utmost extent from entering the system. Specific examples of the method employed for this purpose include a method comprising encapsulating the reaction system with inert gas, such as nitrogen gas, carbon dioxide gas, etc. In some cases, for allowing the metabolic functions in the cells of the aerobic bacterium of the present invention to work effectively during the reaction, addition of a solution of various nutrients or a reagent solution for adjusting and maintaining the pH of the reaction system may be needed, and in such a case, for more effective prevention of oxygen incorporation, it is effective to remove oxygen in the solutions to be added, in advance.

Through the culture performed in the above manner, protocatechuic acid or a salt of the same is produced in the culture solution or the reaction solution.

Examples of the salt of protocatechuic acid, which varies depending on the components of the culture medium or the reaction solution, include alkali metal salts (sodium salt, potassium salt, etc.), and alkali earth metal salts (magnesium salt, calcium salt, etc.).

EXAMPLE

Example 1

Construction of PCA Producing Strain
(1) Preparation of Chromosomal DNA

To obtain PCA-production-related enzyme genes, chromosomal DNAs were prepared from the following strains.

Bacteria of *Corynebacterium glutamicum* strain R (FERM P-18976), *Escherichia coli* (*Escherichia coli* K-12 MG1655), *Providencia rustigianii* (*Providencia rustigianii* JCM 3953), *Corynebacterium casei* (*Corynebacterium casei* JCM 12072), *Corynebacterium efficiens* (*Corynebacterium efficiens* NBRC 100395), *Pantoea ananatis* (*Pantoea ananatis* LMG 20103), *Gluconobacter oxydans* (*Gluconobacter oxydans* ATCC 621H), *Pseudomonas putida* (*Pseudomonas putida* NBRC 14164), *Rhodopseudomonas palustris* (*Rhodopseudomonas palustris* ATCC BAA-98), *Acinetobacter baylyi* (*Acinetobacter baylyi* ATCC33305), *Alteromonas macleodii* (*Alteromonas macleodii* NBRC 102226), *Marinobacter hydrocarbonoclasticus* (*Marinobacter hydrocarbonoclasticus* JCM 20777), *Methylobacterium extorquens* (*Methylobacterium extorquens* JCM 2802), *Neurospora crassa* (*Neurospora crassa* ATCC 36373), *Aspergillus niger* (*Aspergillus niger* JCM 22282), *Mycobacterium smegmatis* (*Mycobacterium smegmatis* ATCC 700084), *Corynebacterium halotolerans* (*Corynebacterium halotolerans* JCM 12676), *Rhodococcus opacus* (*Rhodococcus opacus* ATCC 51881), *Aspergillus oryzae* (*Aspergillus oryzae* JCM 13832), and *Bacillus thuringiensis* (*Bacillus thuringiensis* NBRC 3951) were cultured according to information obtained from organizations from which the strains are available, and chromosomal DNAs were prepared by using DNA genome extraction kit (trade name: "GenomicPrep Cells and Tissue DNA Isolation Kit", manufactured by Amersham plc).

(2) Construction of Plasmid for Expression of PCA-Production-Related Gene

Primer sequences used for isolating target enzyme genes are shown in Table 1. In PCR, Veriti Thermal Cycler (manufactured by Applied Biosystems Inc.) was used, and PrimeSTAR HS DNA Polymerase (manufactured by Takara Bio Inc.) was used as a reaction reagent.

DNA fragments obtained were introduced into cloning vectors containing PgapA promoter ((pCRB207 [Hasegawa S et al., Improvement of the redox balance increases L-valine production by *Corynebacterium glutamicum* under oxygen deprivation conditions. Appl Environ Microbiol. 78(3): 865-875 (2012)], pCRB209 [WO2012/033112], pCRB210 [WO2012/033112]).

TABLE 1

Primers for isolation of PCA-production-related genes, and amplified gene sequences

| Gene source | Enzyme gene | Forward | Reverse | Amplification gene base sequence (gene encode regoin) |
|---|---|---|---|---|
| *Corynebacterium glutamicum* | tkt, tal | SEQ ID NO. 10 | SEQ ID NO. 11 | SEQ ID NO. 1 |
| *Escherichia coli* | aroG | SEQ ID NO. 12 | SEQ ID NO. 13 | SEQ ID NO. 162 |
| *Escherichia coli* | aroG (S180F) | SEQ ID NO. 14 | SEQ ID NO. 15 | SEQ ID NO. 2 |
| *Corynebacterium glutamicum* | aroC, aroK aroB | SEQ ID NO. 16 | SEQ ID NO. 17 | SEQ ID NO. 3 |
| *Corynebacterium glutamicum* | aroA | SEQ ID NO. 18 | SEQ ID NO. 19 | SEQ ID NO. 4 |
| *Corynebacterium glutamicum* | aroD | SEQ ID NO. 20 | SEQ ID NO. 21 | SEQ ID NO. 5 |
| *Corynebacterium glutamicum* | aroE | SEQ ID NO. 22 | SEQ ID NO. 23 | SEQ ID NO. 6 |

TABLE 1-continued

Primers for isolation of PCA-production-related genes, and amplified gene sequences

| Gene source | Enzyme gene | Forward | Reverse | Amplification gene base sequence (gene encode regoin) |
|---|---|---|---|---|
| Corynebacterium glutamicum | qsuB | SEQ ID NO. 24 | SEQ ID NO. 25 | SEQ ID NO. 7 |
| Corynebacterium glutamicum | pobA | SEQ ID NO. 26 | SEQ ID NO. 27 | SEQ ID NO. 8 |
| Providencia rustigianii | ubiC | SEQ ID NO. 28 | SEQ ID NO. 29 | SEQ ID NO. 9 |
| Corynebacterium casei | qsuB | SEQ ID NO. 94 | SEQ ID NO. 95 | SEQ ID NO. 134 |
| Corynebacterium efficiens | qsuB | SEQ ID NO. 96 | SEQ ID NO. 97 | SEQ ID NO. 135 |
| Pantoea ananatis | vllY | SEQ ID NO. 98 | SEQ ID NO. 99 | SEQ ID NO. 136 |
| Gluconobacter oxydans | asbF | SEQ ID NO. 100 | SEQ ID NO. 101 | SEQ ID NO. 137 |
| Pseudomonas putida | quiC | SEQ ID NO. 102 | SEQ ID NO. 103 | SEQ ID NO. 138 |
| Rhodopseudomonas palustris | asbF | SEQ ID NO. 104 | SEQ ID NO. 105 | SEQ ID NO. 139 |
| Acinetobacter baylyi | quiC | SEQ ID NO. 106 | SEQ ID NO. 107 | SEQ ID NO. 140 |
| Alteromonas macleodii | asbF | SEQ ID NO. 108 | SEQ ID NO. 109 | SEQ ID NO. 141 |
| Marinobacter hydrocarbonoclasticus | asbF | SEQ ID NO. 110 | SEQ ID NO. 111 | SEQ ID NO. 142 |
| Methylobacterium extorquens | asbF | SEQ ID NO. 112 | SEQ ID NO. 113 | SEQ ID NO. 143 |
| Neurospora crassa | qsuB | SEQ ID NO. 114 | SEQ ID NO. 115 | SEQ ID NO. 144 |
| Aspergillus niger | qutC | SEQ ID NO. 116 | SEQ ID NO. 117 | SEQ ID NO. 145 |
| Mycobacterium smegmatis | asbF | SEQ ID NO. 118 | SEQ ID NO. 119 | SEQ ID NO. 146 |
| Corynebacterium halotolerans | qsuB | SEQ ID NO. 120 | SEQ ID NO. 121 | SEQ ID NO. 147 |
| Rhodococcus opacus | qsuB | SEQ ID NO. 122 | SEQ ID NO. 123 | SEQ ID NO. 148 |
| Aspergillus oryzae | qutC | SEQ ID NO. 124 | SEQ ID NO. 125 | SEQ ID NO. 149 |
| Bacillus thuringiensis | asbF | SEQ ID NO. 126 | SEQ ID NO. 127 | SEQ ID NO. 150 |

The names of the cloning vectors introduced and the plasmids obtained are shown in Table 2. Since tkt and tal (tkt-tal gene; SEQ ID NO: 1), as well as aroC, aroK, and aroB (aroCKB, SEQ ID NO: 3), were arranged continuously in the same orientation on the chromosome, they were cloned altogether.

TABLE 2

Plasimids for PCA-production-related gene expression

| Gene source | Enzyme gene | Transfer vector | Plasmid |
|---|---|---|---|
| Corynebacterium glutamicum | tkt, tal | pCRB209 | PGppp25 |
| Escherichia coli | aroG | pCRB210 | pSKM1 |
| Escherichia coli | aroG (S180F) | pCRB210 | pCRB237 |
| Corynebacterium glutamicum | aroC, aroK, aroB | pCRB209 | pCRB270 |
| Corynebacterium glutamicum | aroA | pCRB207 | pCRB271 |
| Corynebacterium glutamicum | aroD | pCRB209 | pCRB272 |
| Corynebacterium glutamicum | aroE | pCRB209 | pCRB273 |
| Corynebacterium glutamicum | qsuB | pCRB209 | R493/Lgap10 |
| Corynebacterium glutamicum | pobA | pCRB209 | Pphe314 |
| Providencia rustigianii | ubiC | pCRB209 | Pphe292 |
| Corynebacterium casei | qsuB | pCRB210 | Padi31 |
| Corynebacterium efficiens | qsuB | pCRB209 | Padi25 |
| Pantoea ananatis | vllY | pCRB209 | Padi26 |
| Gluconobacter oxydans | asbF | pCRB209 | Padi28 |
| Pseudomonas putida | quiC | pCRB209 | Padi29 |
| Rhodopseudomonas palustris | asbF | pCRB209 | Padi30 |
| Acinetobacter baylyi | quiC | pCRB209 | PGadi1 |
| Alteromonas macleodii | asbF | pCRB209 | Padi43 |
| Marinobacter hydrocarbonoclasticus | asbF | pCRB209 | Padi42 |
| Methylobacterium extorquens | asbF | pCRB209 | Padi37 |
| Neurospora crassa | qsuB | pCRB209 | Padi39 |

TABLE 2-continued

Plasimids for PCA-production-related gene expression

| Gene source | Enzyme gene | Transfer vector | Plasmid |
|---|---|---|---|
| Aspergillus niger | qutC | pCRB209 | Padi41 |
| Mycobacterium smegmatis | asbF | pCRB209 | Padi36 |
| Corynebacterium halotolerans | qsuB | pCRB209 | Padi35 |
| Rhodococcus opacus | qsuB | pCRB209 | Padi44 |
| Aspergillus oryzae | qutC | pCRB209 | Padi40 |
| Bacillus thuringiensis | asbF | pCRB207 | Padi34 |

(3) Construction of Plasmids for Chromosomal Integration of the PCA-Production-Related Genes A DNA region necessary for markerless introduction of a PCA-production-related gene into chromosome of Corynebacterium glutamicum strain R was determined based on a sequence that was reported not to be essential for the growth of Corynebacterium glutamicum strain R [Appl. Environ. Microbiol. 71:3369-3372 (2005)] (SSI region). This DNA region was amplified by the PCR method. The DNA fragment thus obtained was introduced into the markerless gene transfer plasmid pCRA725 [J. Mol. Microbiol. Biotechnol. 8:243-254 (2004), (JP-A-2006-124440)]. To pCRB260, pCRB263, pCRB266, pCRB267, pCRB274, and pCRB279, a restriction enzyme site (unique site) for incorporating a gene in the SSI region was introduced by the inverse PCR method. The primer sequences used for isolation of the SSI regions and Inverse PCR and chromosome transfer vectors obtained are shown in Table 3.

TABLE 3

Sequences of primers used for isolating SSI regions, and obtained vectors for chromosomal integration

| vectors for chromosomal integration | SSI region | Forward | Reverse |
|---|---|---|---|
| pCRB274 | SSI 1-3 | SEQ ID NO. 30 | SEQ ID NO. 31 |
|  |  | SEQ ID NO. 32* | SEQ ID NO. 33* |
| pCRB260 | SSI 2-3 | SEQ ID NO. 34 | SEQ ID NO. 35 |
|  |  | SEQ ID NO. 36* | SEQ ID NO. 37* |
| pCRB261 | SSI 2-4 | SEQ ID NO. 38 | SEQ ID NO. 39 |
| pCRB262 | SSI 3-3 | SEQ ID NO. 40 | SEQ ID NO. 41 |
| pCRB275 | SSI 4-3 | SEQ ID NO. 42 | SEQ ID NO. 43 |
| pCRB263 | SSI 4-7 | SEQ ID NO. 44 | SEQ ID NO. 45 |
|  |  | SEQ ID NO. 46* | SEQ ID NO. 47* |
| pCRB276 | SSI 5-1 | SEQ ID NO. 48 | SEQ ID NO. 49 |
| pCRB277 | SSI 6-1 | SEQ ID NO. 50 | SEQ ID NO. 51 |
| pCRB266 | SSI 8 | SEQ ID NO. 52 | SEQ ID NO. 53 |
|  |  | SEQ ID NO. 54* | SEQ ID NO. 55* |
| pCRB278 | SSI 8-1 | SEQ ID NO. 56 | SEQ ID NO. 57 |
| pCRB279 | SSI 8-7 | SEQ ID NO. 58 | SEQ ID NO. 59 |
|  |  | SEQ ID NO. 60* | SEQ ID NO. 61* |
| pCRB267 | SSI 9-4 | SEQ ID NO. 62 | SEQ ID NO. 63 |
|  |  | SEQ ID NO. 64* | SEQ ID NO. 65* |
| pCRB280 | SSI 9-5 | SEQ ID NO. 66 | SEQ ID NO. 67 |
| pCRB281 | SSI 9-6 | SEQ ID NO. 68 | SEQ ID NO. 69 |
| pCRB269 | SSI 10-3 | SEQ ID NO. 70 | SEQ ID NO. 71 |
| pCRB282 | SSI 10-6 | SEQ ID NO. 72 | SEQ ID NO. 73 |

*Primer used in Inverse PCR

PgapA promoter fusion enzyme gene fragments were obtained from the PCA-production-related gene expression plasmids constructed as shown in Table 2, and were introduced into the chromosome transfer plasmids described above. Obtained PCA-production-related gene chromosome transfer plasmids are shown in Table 4.

TABLE 4

Plasmids for introduction of the PCA-production-related gene into chromosome

| Gene source | Gene | SSI region | Chromosome transfer plasmid |
|---|---|---|---|
| Corynebacterium glutamicum | tkt, tal | SSI 9-5 | pCRB283 |
| Escherichia coli | aroG (S180F) | SSI 1-3 | pCRB284 |
| Escherichia coli | aroG (S180F) | SSI 2-3 | pCRB285 |
| Corynebacterium glutamicum | aroC, aroK, aroB | SSI 8-7 | pCRB286 |
| Corynebacterium glutamicum | aroC, aroK, aroB | SSI 9-4 | pCRB287 |
| Corynebacterium glutamicum | aroC, aroK, aroB | SSI 10-6 | pCRB288 |
| Corynebacterium glutamicum | aroA | SSI 4-7 | pCRB289 |
| Corynebacterium glutamicum | aroA | SSI 8-1 | pCRB290 |
| Corynebacterium glutamicum | aroD | SSI 4-3 | pCRB291 |
| Corynebacterium glutamicum | aroD | SSI 10-3 | pCRB292 |
| Corynebacterium glutamicum | aroE | SSI 2-4 | pCRB293 |
| Corynebacterium glutamicum | aroE | SSI 9-6 | pCRB294 |
| Corynebacterium glutamicum | qsuB | SSI 5-1 | pCRB295 |
| Corynebacterium glutamicum | pobA | SSI 3-3 | pCRB296 |
| Corynebacterium glutamicum | pobA | SSI 6-1 | pCRB297 |
| Providencia rustigianii | ubiC | SSI 8 | pCRB298 |
| Corynebacterium halotolerans | qsuB | SSI 5-1 | pCRG6 |
| Aspergillus oryzae | qutC | SSI 5-1 | pCRG7 |

(4) Construction of Plasmids for Disruption of Chromosomal Gene of Corynebacterium glutamicum Strain R A DNA region necessary for markerless disruption of a chromosomal gene of Corynebacterium glutamicum strain R was amplified by the PCR method. Each PCR fragment is linkable in overlap regions. The DNA fragment obtained was introduced into a markerless gene disruption plasmid pCRA725 [J. Mol. Microbiol. Biotechnol. 8:243-254(2004), (JP-A-2006-124440)]. Obtained plasmids for chromosomal gene disruption are shown in Table 5.

TABLE 5

Plasmids for disruption of chromosomal genes of Corynebacterium glutamicum strain R

| Plasmid for chromosome disruption | Disrupted gene | Forward | Reverse |
|---|---|---|---|
| pCRB229 | qsuB | SEQ ID NO. 74 | SEQ ID NO. 75* |
|  |  | SEQ ID NO. 76* | SEQ ID NO. 77 |
| pCRB299 | qsuD | SEQ ID NO. 78 | SEQ ID NO. 79* |
|  |  | SEQ ID NO. 80* | SEQ ID NO. 81 |
| pCRG1 | pobA | SEQ ID NO. 82 | SEQ ID NO. 83* |
|  |  | SEQ ID NO. 84* | SEQ ID NO. 85 |
| pCRG2 | poxF | SEQ ID NO. 86 | SEQ ID NO. 87* |
|  |  | SEQ ID NO. 88* | SEQ ID NO. 89 |
| pCRG3 | pcaHG | SEQ ID NO. 90 | SEQ ID NO. 91* |
|  |  | SEQ ID NO. 92* | SEQ ID NO. 93 |
| pCRG4 | aroE | SEQ ID NO. 130 | SEQ ID NO. 131* |
|  |  | SEQ ID NO. 132* | SEQ ID NO. 133 |

*Primer including overlap region (5) Construction of PCA Producing Strains by Chromosomal Gene Recombination The markerless chromosomal gene transfer vector pCRA725 is a plasmid that cannot be replicated in Corynebacterium glutamicum R. In a case of a single crossover strain that has a crossover with the homologous region on the chromosome introduced into the plasmid pCRA725, the strain exhibits the kanamycin resistance due to the expression of the kanamycin-resistant gene on pCRA725, and the lethality in a sucrose-containing medium due to the expression of the sacR-sacB gene of the Bacillus subtilis. In contrast, in a case of a double crossover strain, the strain exhibits the kanamycin sensitivity due to the loss of the kanamycin-resistant gene on pCRA725, and the viability in a sucrose-containing medium due to the loss of the sacR-sacB gene. A markerless chromosomal gene introduced strain, therefore, exhibits the kanamycin sensitivity and the viability in the sucrose-containing medium.

By the above-described methods, PCA-production-related gene chromosome introduced strains were constructed by using the above-described PCA-production-related gene chromosome transfer plasmids and the chromosomal genes disruption plasmids. Corynebacterium glutamicum strain X5C1 [Appl Microbiol Biotechnol. 81(4):691-699 (2008)], which is a coryneform bacterium that is rendered to utilize xylose and cellobiose, was used as a host strain. Further, a plasmid pCRA728 for disruption of gene IdhA [J Mol Microbiol Biotechnol. 8(4):243-254 (2004)], an arabinose-utilizing gene chromosome transfer plasmid pCRD109 [Appl Microbiol Biotechnol. 85(1):105-115 (2009)], and an arabinose-transporter gene chromosome transfer plasmid pCRD108 [Appl Microbiol Biotechnol. 85(1):105-115 (2009)], were used as well. This chromosomal gene recombination is outlined in Table 6.

TABLE 6

Construction of PCA-production-related gene-introduced strains by chromosomal gene recombination

| Constructed strain | Chromosome introduced gene | Disrupted chromosomal gene |
|---|---|---|
| PCA1 | xylABx4, bgIF(V317A)A, araBAD, araE, tkt-tal, aroG(S180F)x2, aroCKBx3, aroAx2, aroDx2, qsuB, pobAx2, ubiC | aroE, qsuD, poxF, pcaHG, IdhA |
| PCA2 | xylABx4, bgIF(V317A)A, araBAD, araE, tkt-tal, aroG(S180F)x2, aroCKBx3, aroAx2, aroDx2, aroEx2, pobAx2, ubiC | qsuB, qsuD, poxF, pcaHG, IdhA |
| PCA3 | xylABx4, bgIF(V317A)A, araBAD, araE, tkt-tal, aroG(S180F)x2, aroCKBx3, aroAx2, aroDx2, aroEx2, qsuB, pobAx2, ubiC | qsuD, poxF, pcaHG, IdhA |
| PCA4 | xylABx4, bgIF(V317A)A, araBAD, araE, tkt-tal, aroG(S180F)x2, aroCKBx3, aroAx2, aroDx2, aroEx2, qsuB (from *Corynebacterium* halotolerans), pobAx2, ubiC | qsuD, poxF, pcaHG, IdhA |
| PCA5 | xylABx4, bgIF(V317A)A, araBAD, araE, tkt-tal, aroG(S180F)x2, aroCKBx3, aroAx2, aroDx2, aroEx2, qsuB (from *Aspergillus oryzae*), pobAx2, ubiC | qsuD, poxF, pcaHG, IdhA |
| DHS1 | xylABx4, bgIF(V317A)A, araBAD, araE, tkt-tal, aroG(S180F)x2, aroCKBx3, aroAx2, aroDx2, pobAx2 | qsuB, qsuD, poxF, pcaHG, aroE, IdhA |
| CRZ22 | xylABx5, bgIF(V317A)A, araBAD, araE | IdhA | x2, x3, x4: indicating the number of genes introduced into chromosome (6) Construction of Strains Harboring Plasmids for Expression of PCA-Production-Related Genes

*Corynebacterium glutamicum* transformants, into which the above-described various types of 3-dehydroshikimate dehydratase gene expression plasmids derived from microorganisms were introduced, were constructed. The plasmid-introduced strains are outlined in Table 7.

TABLE 7

Strains harboring plasmids for the expression of the 3-dehydroshikimate dehydratase gene

| Constructed strain | Host strain | Introduced plasmid | 3-dehydroshikimate dehydratase gene source |
|---|---|---|---|
| DHS1/pCRB209 | DHS1 | pCRB209 | |
| PR017 | DHS1 | R493/Lgap10 | *Corynebacterium glutamicum* |
| PR018 | DHS1 | Padi31 | *Corynebacterium casei* |
| PR019 | DHS1 | Padi25 | *Corynebacterium efficiens* |
| PR020 | DHS1 | Padi26 | *Pantoea ananatis* |
| PR021 | DHS1 | Padi28 | *Gluconobacter oxydans* |
| PR022 | DHS1 | Padi29 | *Pseudomonas putida* |
| PR023 | DHS1 | Padi30 | *Rhodopseudomonas palustris* |
| PR024 | DHS1 | PGadi1 | *Acinetobacter baylyi* |
| PR028 | DHS1 | Padi43 | *Alteromonas macleodii* |
| PR029 | DHS1 | Padi42 | *Marinobacter hydrocarbonoclasticus* |
| PR030 | DHS1 | Padi37 | *Methylobacterium extorquens* |
| PR031 | DHS1 | Padi39 | *Neurospora crassa* |
| PR032 | DHS1 | Padi41 | *Aspergillus niger* |
| PR033 | DHS1 | Padi36 | *Mycobacterium smegmatis* |
| PR034 | DHS1 | Padi35 | *Corynebacterium halotolerans* |
| PR037 | DHS1 | Padi44 | *Rhodococcus opacus* |
| PR038 | DHS1 | Padi40 | *Aspergillus oryzae* |
| PR039 | DHS1 | Padi34 | *Bacillus thuringiensis* |

*Corynebacterium glutamicum* PCA4 was deposited in Incorporated Administrative Agency National institute of Technology and Evaluation, NITE Patent Microorganisms Depositary (2-5-8 Kazusakamatari, Kisarazu-shi, Chiba 292-0818 Japan) as an international depositary authority (International deposit date: Mar. 9, 2016, Accession Number: NITE BP-02217 under the Budapest Treaty). The strain is therefore available to the public.

Reference Example 1

Verification that Coryneform Bacterium Exhibits High Resistance Against Protocatechuic Acid, as Compared with Other Microorganisms In a case where a product that has cytotoxicity, such as protocatechuic acid, is produced by the fermentation process using microorganisms, it is important that a host microorganism has resistance against the product, that is, hardly suffers from growth inhibition by the product. Then, for studying the degree of resistance against protocatechuic acid of *Corynebacterium glutamicum*, which is preferable as a host microorganism in the present invention, in comparison with other microorganisms, studies were made on the inhibition by protocatechuic acid of the growth of *Corynebacterium glutamicum*, *Escherichia coli*, *Bacillus subtilis*, *Pseudomonas putida*, *Rhodococcus erythropolis*, and *Saccharomyces cerevisiae* in aerobic culture.

*Corynebacterium glutamicum* strain R was applied to an A-agar plate [obtained by dissolving the following in distilled water 1 L: $(NH_2)_2CO$ 2 g, $(NH_4)_2SO_4$ 7 g, $KH_2PO_4$ 0.5 g, $K_2HPO_4$ 0.5 g, $MgSO_4 \cdot 7H_2O$ 0.5 g, 0.06% (w/v) $Fe_2SO_4 \cdot 7H_2O$+0.042% (w/v) $MnSO_4 \cdot 2H_2O$ 1 ml, 0.02% (w/v) biotin solution 1 ml, 0.01% (w/v) thiamine solution 2 ml, yeast extract 2 g, vitamin assay casamino acid 7 g, agar 20 g] containing glucose at 4%, and was cultured at 33° C. for 16 hours. One platinum loop of *Corynebacterium glutamicum* grown on the plate described above was inoculated in a test tube having therein 10 ml of an A-liquid medium [obtained by dissolving the following in distilled water 1 L: $(NH_2)_2CO$ 2 g, $(NH_4)_2SO_4$ 7 g, $KH_2PO_4$ 0.5 g, $K_2HPO_4$ 0.5 g, $MgSO_4 \cdot 7H_2O$ 0.5 g, 0.06% (w/v) $Fe_2SO_4 \cdot 7H_2O$+0.042% (w/v) $MnSO_4 \cdot 2H_2O$ 1 ml, 0.02% (w/v) biotin solution 1 ml, 0.01% (w/v) thiamine solution 2 ml, yeast extract 2 g, vitamin assay casamino acid 7 g] containing of glucose at 4%, and was subjected to aerobic shaking culture at 33° C. for 16 hours. *Corynebacterium glutamicum* strain R grown under the above-described conditions was inoculated in 10 ml of the above-described A-liquid medium containing glucose at 4% so that the initial bacterial cell concentration $OD_{610}$=0.1. Simultaneously, protocatechuic acid was added so that the final concentrations thereof became 0, 25, 50, 100, 250, 500 mM, and aerobic shaking culture was carried out at 33° C. The growth of bacterial cells was determined by measuring $OD_{610}$.

Further, *Escherichia coli* strain K12, *Bacillus subtilis* strain NBRC14144, *Pseudomonas putida* strain ATCC700801, and *Rhodococcus erythropolis* strain ATCC27854 were applied to LB-agar plate [containing 1% polypeptone, 0.5% yeast extract, 0.5% sodium chloride, and 1.5% agar]. *Escherichia coli* strain K12 and *Bacillus subtilis* strain NBRC14144 were cultured at 37° C. for 16 hours, while *Pseudomonas putida* strain ATCC700801 and *Rhodococcus erythropolis* strain ATCC27854 were cultured at 30° C. for 16 hours. Each strain grown on the plate described above was inoculated in 10 ml of LB-liquid medium [1% polypeptone, 0.5% yeast extract, and 0.5% sodium chloride]. *Escherichia coli* strain K12 and *Bacillus subtilis* strain NBRC14144 were subjected to aerobic shaking culture at 37° C. for 16 hours, while *Pseudomonas putida* strain ATCC700801 and *Rhodococcus erythropolis* strain ATCC27854 were subjected to aerobic shaking culture at 30° C. for 16 hours. Each strain grown under the above-described conditions was inoculated in 10 ml of the LB-liquid medium so that the initial bacterial cell concentration $OD_{610}$=0.1, and simultaneously protocatechuic acid was added so that the final concentrations were 0, 25, 50, 100, 250, 500 mM. *Escherichia coli* strain K12 and *Bacillus subtilis* strain NBRC14144 were subjected to aerobic shaking culture at 37° C., while *Pseudomonas putida* strain ATCC700801 and *Rhodococcus erythropolis* strain ATCC27854 was subjected to aerobic shaking culture at 30° C. The growth of bacterial cells was determined by measuring $OD_{610}$.

Further, *Saccharomyces cerevisiae* strain NBRC2376 was applied to YPD agar plate [2% polypeptone, 1% yeast extract, 2% glucose, and 1.5% agar], and was cultured at 30° C. for 16 hours. *Saccharomyces cerevisiae* strain NBRC2376 on the plate described above was inoculated in YPD liquid medium [2% polypeptone, 1% yeast extract, and 2% glucose], and was subjected to aerobic shaking culture at 30° C. for 16 hours. *Saccharomyces cerevisiae* strain NBRC2376 grown under the above-described conditions was inoculated in 10 ml of the YPD liquid medium so that the initial bacterial cell concentration $OD_{610}$=0.1, and simultaneously protocatechuic acid was added so that the final concentrations were 0, 25, 50, 100, 250, 500 mM. Aerobic shaking culture was performed at 30° C. The growth of bacterial cells was determined by measuring $OD_{610}$.

How the addition of protocatechuic acid to medium influenced aerobic growth of each strain was analyzed, and the results are shown in FIG. 2.

The growth of *Escherichia coli* strain K12 was significantly inhibited under the presence of 100 mM protocatechuic acid, and the growth thereof was substantially completely inhibited under the presence of 250 mM protocatechuic acid.

The growth of *Bacillus subtilis* strain NBRC14144 was significantly inhibited under the presence of 250 mM protocatechuic acid, and the growth thereof was substantially completely inhibited under the presence of 500 mM protocatechuic acid.

The growth of *Pseudomonas putida* strain ATCC700801 was strongly inhibited under the presence of 100 mM protocatechuic acid, and the growth thereof was substantially completely inhibited under the presence of 250 mM protocatechuic acid.

The growth of *Rhodococcus erythropolis* strain ATCC27854 was strongly inhibited under the presence of 250 mM protocatechuic acid, and the growth thereof was substantially completely inhibited under the presence of 500 mM protocatechuic acid.

The growth of *Saccharomyces cerevisiae* strain NBRC2376 was inhibited under the presence of 250 mM protocatechuic acid, and the growth thereof was significantly inhibited under the presence of 500 mM protocatechuic acid.

In contrast, *Corynebacterium glutamicum* strain R was able to exhibit robust growth under the presence of 250 to 500 mM of protocatechuic acid, under which the growth of the other strains was significantly inhibited, or substantially completely inhibited.

In this way, it was indicated that *Corynebacterium glutamicum* has high resistance against protocatechuic acid as compared with other microorganisms that are reported to be protocatechuic acid producing hosts and typical solvent-resistant bacteria, and therefore, *Corynebacterium glutamicum* is highly suitable as a protocatechuic acid producing host.

Reference Example 2

Verification that Coryneform Bacterium has High Saccharide Consumption Ability Under Presence of High Concentration of Protocatechuic Acid As indicated in Reference Example 1, *Corynebacterium glutamicum* was able to grow even under the presence of a high concentration of protocatechuic acid. Then, a glucose consumption ability of *Corynebacterium glutamicum* under the presence of a high concentration of protocatechuic acid was further studied in the following manner.

*Corynebacterium glutamicum* strain R was applied to the above-described A-agar plate containing glucose 4%, and was cultured at 33° C. for 16 hours. One platinum loop of *Corynebacterium glutamicum* strain R grown on the above-described plate was inoculated in a test tube having therein 10 ml of the above-described A-liquid medium containing glucose 4%, and was subjected to aerobic shaking culture at 33° C. for 16 hours. *Corynebacterium glutamicum* strain R grown under the above-described conditions was inoculated in 10 ml of the above-described A-liquid medium containing glucose 4% so that the initial bacterial cell concentration $OD_{610}$=0.2. Simultaneously, protocatechuic acid was added so that the final concentrations thereof became 0, 50, 250, 500 mM, and aerobic shaking culture was carried out at 33° C. After 24-hour culture, culture solutions were collected, and centrifuged (4° C., 15,000×g, 5 minutes). Concentrations of glucose in the supernatants obtained were measured by a glucose sensor in the same manner as Example 2 to be described below. The amounts of glucose consumed by *Corynebacterium glutamicum* strain R under the presence of protocatechuic acid of respective concentrations after culture of 24 hours are shown in FIG. 3.

As shown in FIG. 3, the decrease in the saccharide consumption by *Corynebacterium glutamicum* was small even under the presence of a high concentration of protocatechuic acid.

The results of Reference Examples 1 and 2 prove that *Corynebacterium glutamicum* is extremely excellent as a protocatechuic acid producing host.

Example 2

Test of Protocatechuic Acid Production by Aerobic Reaction of Non-Growing (Resting) Bacterial Cells of *Corynebacterium glutamicum* Transformant Under Control of Jar Fermenter Regarding protocatechuic acid producing strains constructed on the basis of strains utilizing mixed saccharides, derived from *Corynebacterium glutamicum* strain R, which are PCA1, PCA2, PCA3, PCA4, PCA5 (Example 1 (Table 6)), their protocatechuic acid producing abilities in the aerobic reaction of non-growing (resting) bacterial cells under the control of a jar fermenter (manufactured by Able Corp., Type: BMJ1L) were confirmed in the following manner.

Strain PCA1 was inoculated in 10 ml of the above-described A-liquid medium (in a test tube) to which phenylalanine, tyrosine, and tryptophan, 20 μg/ml each, p-amino benzoate 10 μg/ml, shikimate 3.2 mM, and glucose 4% (in the final concentrations) were added, and further, strains PCA2, PCA3, PCA4, and PCA5 were inoculated in 10 ml of the above-described A-liquid medium (in a test tube) to which glucose 4% was added, and thereafter, were subjected to aerobic shaking culture at 33° C. for 12 to 16 hours.

*Corynebacterium glutamicum* strain PCA1 grown under the above-described conditions was inoculated, so that initial OD=0.05, in 100 ml of the above-described A-liquid medium (in 500 ml flask) to which phenylalanine, tyrosine, and tryptophan, each 20 μg/ml, p-amino benzoate 10 μg/ml, shikimate 3.2 mM, and glucose 4% (in the final concentrations) were added. *Corynebacterium glutamicum* strains PCA2, PCA3, PCA4, and PCA5 grown under the above-described conditions was inoculated, so that initial OD=0.05, in 100 ml of the above-described A-liquid medium (in 500 ml flask) containing glucose 4%. These were subjected to aerobic shaking culture at 33° C. for 16 hours.

*Corynebacterium glutamicum* strain PCA1 grown under the above-described conditions was inoculated, so that $OD_{610}$=0.3, in 600 ml of the above-described A-(-UB) liquid medium to which glucose 80 g/l, phenylalanine, tyrosine, and tryptophan, 100 μg/ml each, p-amino benzoate 50 μg/ml, shikimate 16 mM, and an antifoam agent (DISFOAM CB-442) 3 g/l (in the final concentrations) were added. *Corynebacterium glutamicum* strains PCA2, PCA3, PCA4, and PCA5 grown under the above-described conditions were inoculated, so that $OD_{610}$=0.3, in 600 ml of the above-described A-(-UB) liquid medium to which glucose 100 g/l and an antifoam agent (DISFOAM CB-442) 3 g/l (in the final concentrations) were added. Each of these was subjected to aerated agitated culture in a 1000-ml jar fermenter (manufactured by Able Corp., Type: BMJ1L) under the conditions of 33° C., pH 7.0 (controlled to be constant by addition of 5 N aqueous ammonia), aeration amount 0.6 L/min (air, 1 vvm), and dissolved oxygen concentration (DO) 10% (assuming that the saturated dissolved oxygen concentration under the atmospheric pressure at 33° C. is 100%), for 19 to 20 hours.

The strains of *Corynebacterium glutamicum* grown under the above-described conditions were collected by centrifugation (4° C., 5000×g, 10 minutes), and bacterial cells thereof thus obtained were washed once with BT(-UB)-liquid medium [obtained by dissolving $(NH_4)_2SO_4$ 7 g, $KH_2PO_4$ 0.5 g, $K_2HPO_4$ 0.5 g, $MgSO_4.7H_2O$ 0.5 g, 0.06% (w/v) $(Fe_2SO_4.7H_2O+0.042\%$ (w/v) $MnSO_4.2H_2O)$ 1 ml, and 100 μg/ml thiamine solution 2 ml in 1 L of distilled water], and were suspended in the foregoing BT(-UB)-liquid medium containing 10% of glucose so that 25 g wet bacterial cells per 250 ml (10% bacterial cells as a wet bacterial cell weight in medium). Then, by using the 1000-ml jar fermenter, a protocatechuic acid production reaction was caused to occur under the conditions of 33° C., pH 7.0 (controlled to be constant by addition of 5 N aqueous ammonia), aeration amount 0.25 L/min (air, 1 vvm), and dissolved oxygen concentration (DO) 5% (assuming that the saturated dissolved oxygen concentration under the atmospheric pressure at 33° C. is 100%). The glucose concentration in the reaction solution was measured chronologically by using a glucose sensor (Oji-keisoku.co.jp, BF-5i), and glucose was additionally added as required. The concentration of aromatic metabolite in the supernatant of bacterial reaction was analyzed by using a high-performance liquid chromatography system (Prominence HPLC (manufactured by Shimadzu Corporation), COSMOSIL Packed column 5C18-AR-II, separation using 20% methanol and 0.07% perchloric acid for the mobile phase).

Results of the experiments of protocatechuic acid production by aerobic reaction of non-growing (resting) bacterial cells using the respective strains are shown in Table 8.

TABLE 8

Experiments of protocatechuic acid production by aerobic reaction of non-growing (resting) bacterial cells under control of jar fermenter (reaction time: 24 hours)

| Strain | Product concentration (mM)[*1] | | | | | | Glucose consumption (mM) | Saccharide-based yield (%, mol/(mol glucose)) | |
|---|---|---|---|---|---|---|---|---|---|
| | PCA | SA | DHS | Cho | 4HBA | Phe | | PCA | total[*2] |
| PCA1 | 273 | 0.41 | 6.07 | ND | ND | ND | 806 | 33.8 | 34.6 |
| PCA2 | 153 | 13.2 | 0.27 | 12.4 | 3.4 | 13.1 | 1538 | 10.0 | 12.7 |
| PCA3 | 515 | 0.9 | 0.54 | 6.6 | 0.28 | ND | 1488 | 34.6 | 35.2 |
| PCA4 | 536 | 2.1 | 0.67 | 10.9 | 0.82 | ND | 1364 | 39.3 | 40.3 |
| PCA5 | 408 | 2.8 | 0.82 | 11.5 | 0.78 | ND | 1350 | 30.2 | 31.4 |

[*1]PCA: protocatechuic acid, SA: shikimate, DHS: 3-dehydroshikimate, Cho: chorismate,
4HBA: 4-4-hydroxybenzoate, Phe: phenylalanine, ND: not detected
[*2]Molar yields of total production amount of PCA, SA, DHS, Cho, 4HBA, and Phe with respect to glucose consumption Amounts of PCA produced after 24-hour reaction of respective strains were as follows: strain PCA1, 273 mM (42.1 g/l); strain PCA2, 153 mM (23.6 g/l); strain PCA3, 515 mM (79.4 g/l); strain PCA4, 536 mM (82.5 g/l); and strain PCA5, 408 mM (62.8 WI). Further, respective molar yields to saccharides of the PCA production were as follows: strain PCA1, 33.8%; strain PCA2, 10.0%; strain PCA3, 34.6%; strain PCA4, 39.3%; and strain PCA5, 30.2%.

The above-described results indicate that: strains PCA3, PCA4, and PCA5, in which both of (a) the production of protocatechuic acid by the conversion of 3-dehydroshikimate into protocatechuic acid catalyzed by 3-dehydroshikimate dehydratase, and (b) the production of protocatechuic acid by the conversion of chorismate (metabolic end product of the shikimate pathway) into protocatechuic acid catalyzed by chorismate pyruvate lyase and 4-hydroxybenzoate hydroxylase, were enhanced, had a high protocatechuic acid producing ability in the process of reaction of non-growing (resting) bacterial cells in which an inorganic salt minimal medium was used. Among these, strain PCA3 into which a 3-dehydroshikimate dehydratase gene of *Corynebacterium glutamicum* was introduced, and strain PCA4 into which a 3-dehydroshikimate dehydratase gene of *Corynebacterium halotolerans* was introduced exhibited particularly high PCA productivities. Further, it was indicated that these strains PCA3, PCA4, and PCA5 exhibited robust growth even without addition of auxiliary nutrient sources including aromatic amino acid, during microbial cell culture in a nutrient medium as well.

Though strain PCA1, which generates protocatechuic acid depending only on (a) the production of protocatechuic acid by the conversion of 3-dehydroshikimate into protocatechuic acid catalyzed by 3-dehydroshikimate dehydratase, also exhibited a relatively high protocatechuic acid producing ability, the productivity was inferior to strains PCA3, PCA4, or PCA5, which generated PCA through both of the pathways of (a) and (b). Further, since strain PCA1 has the aromatic amino acid biosynthetic pathway blocked by the disruption of the shikimate dehydrogenase gene (aroE), the strain exhibited auxotrophy for aromatic amino acids and 4-aminobenzoates, and in a case where this strain is grown in a nutrient medium, it was necessary to add such nutrient sources to the medium.

On the other hand, it was indicated that the PCA production ability of strain PCA2, which generates protocatechuic acid depending only on (b) the production of protocatechuic acid by the conversion of chorismate into protocatechuic acid catalyzed by chorismate pyruvate lyase and 4-hydroxybenzoate hydroxylase, was significantly inferior to the other strains described above.

The above-described results indicate that when both of (a) the production of protocatechuic acid by the conversion of 3-dehydroshikimate into protocatechuic acid catalyzed by 3-dehydroshikimate dehydratase and (b) the production of protocatechuic acid by the conversion of chorismate into protocatechuic acid catalyzed by chorismate pyruvate lyase and 4-hydroxybenzoate hydroxylase were enhanced, the protocatechuic acid producing ability was synergistically increased, as compared with a case where only either one of the two was enhanced.

Example 3

Measurement of Enzyme Activities of 3-Dehydroshikimate Dehydratase, Chorismate Pyruvate Lyase, and 4-Hydroxybenzoate Hydroxylase in Protocatechuic Acid Producing Strain Regarding strains PCA1, PCA2, and PCA3, and strain CRZ22 (Table 6) as a parent strain of strains PCA1, PCA2, and PCA3, respective enzyme activities of 3-dehydroshikimate dehydratase, chorismate pyruvate lyase, and 4-hydroxybenzoate hydroxylase were measured in the following manner.

Aerobic reactions of non-growing (resting) bacterial cells were caused to occur through the same procedure as that in Example 1, using jar fermenters of strains CRZ22, PCA1, PCA2, and PCA3, and strain culture solutions after 6-hour reactions were collected. Bacterial cells were collected by centrifugation. After the bacterial cells were washed once with 20 mM Tris-HCl (pH7.5), the cells were suspended in 1-ml bacterial cell disruption buffer (100 mM Tris-HCl (pH7.5), 20 mM KCl, 20 mM $MgCl_2$, 0.1 mM EDTA, and 2 mM DTT)), and were disrupted with a Multi-beads shocker (Yasui Kikai) and glass beads. The bacterial cell disruption liquid was centrifuged under the conditions of 15000 rpm, 10 min, 4° C., and the supernatant was obtained as crude enzyme extraction liquid. The protein concentration in each crude enzyme extraction was quantified by using Protein assay kit (Bio-Rad, USA), with reference to BSA (Bovine serum albumin) as a standard. Each enzyme activity in the crude enzyme extraction of each strain was measured by the activity measuring method described above.

The results are shown in Table 9.

TABLE 9

Enzyme activities in cell extracts of strains during protocatechuic acid production reaction

| Strain | Enzyme activity (mU/mg protein)*[1] | | |
|---|---|---|---|
| | QsuB | UbiC | PobA |
| CRZ22 | ND | ND | — |
| PCA1 | 75.3 ± 3.7 | — | — |
| PCA2 | ND | 26.2 ± 4.1 | 86.9 ± 11.5 |
| PCA3 | 87.3 ± 10.3 | 56.4 ± 2.1 | 123.6 ± 13.5 |

*[1]QsuB; 3-dehydroshikimate dehydratase, UbiC: chorismate pyruvate lyase, PobA: 4-hydroxybenzoate hydroxylase, ND; not detected, —: not determined From strain CRZ22 as the parent strain, no significant activity was detected regarding the three enzyme activities tested. This suggests that these enzymes exhibited weak expression or substantially no expression on the strain.

On the other hand, from strain PCA1, 3-dehydroshikimate dehydratase (QsuB) activity was detected in association with the introduction of the 3-dehydroshikimate dehydratase gene (qsuB). Since the gene aroE encoding shikimate dehydrogenase was disrupted in strain PCA1, the shikimate pathway was blocked on the stage of the enzyme reaction. This supports that the PCA production in strain PCA1 occurred depending only on (a) 3-dehydroshikimate dehydratase.

From strain PCA2, in correspondence to the introduction of genes of chorismate pyruvate lyase (UbiC) and 4-hydroxybenzoate hydroxylase (PobA), activities of these enzymes were detected, whereas no activity of 3-dehydroshikimate dehydratase (QsuB) was detected. This supports that in strain PCA2, the protocatechuic acid production depending on (a) 3-dehydroshikimate dehydratase did not occur, and protocatechuic acid was generated through a pathway via (b) chorismate pyruvate lyase (UbiC), and 4-hydroxybenzoate hydroxylase (PobA).

Further, all of the three enzyme activities described above were detected in strain PCA3, which supports that the production of PCA occurred through both of the pathways of (a) and (b) in this strain.

The above-described results indicate that, in each of PCA producing strains thus constructed, the introduced enzyme genes were functionally expressed. In addition to these results, the results of Example 2 (Table 8) also suggest that specific PCA producing pathways functioned in the strains, respectively. More specifically, chorismate or 4-HBA was not detected at all in the supernatant of reaction of strain PCA1 in which a shikimate dehydrogenase (aroE) gene was disrupted, and this suggests that in this strain, the PCA producing pathway of (b) (the pathway of production of protocatechuic acid from chorismate, which was catalyzed by chorismate pyruvate lyase (UbiC) activity and 4-hydroxybenzoate hydroxylase (PobA)) does not function. On the other hand, accumulation of chorismate and 4-HBA was detected in the supernatants of reaction of strains PCA2 and PCA3, in which all of the enzyme genes on the shikimate pathway leading to the chorismate production were introduced, and this suggests that the pathway (b) of the production of PCA from chorismate functioned in these PCA producing strains.

Example 4

Search for Heterologous Genes that Encodes Competent Shikimate Dehydratase

The results of Examples 2 and 3 indicate that the ability of coryneform bacterium transformants of producing protocatechuic acid was noticeably increased by the enhancement of the enzyme activity caused by the introduction of 3-dehydroshikimate dehydratase gene. On the other hand, regarding the coryneform bacterium transformants PCA1 and PCA3, a 3-dehydroshikimate dehydratase gene derived from *Corynebacterium glutamicum* was introduced, but there seemed to be a possibility that a more competent 3-dehydroshikimate dehydratase existed in other microorganisms. Then, the search of a competent heterologous 3-dehydroshikimate dehydratase gene was performed.

As a host for the search of a 3-dehydroshikimate dehydratase gene, strain DHS1 (Table 6) was used, which is a 3-dehydroshikimate producing strain in which a 3-dehydroshikimate dehydratase gene (qsuB) and shikimate dehydrogenase gene (aroE) on a chromosome were disrupted and to which shikimate pathway genes aroG$^{S180F}$, aroB, and aroD were introduced. Transformed strains obtained by introducing, into this strain, 3-dehydroshikimate dehydratase genes derived from various types of microorganisms by using multicopy expression vectors (pCRB209, pCRB207, alternatively pCRB210) were constructed (Table 7). These transformed strains were cultured in test tubes, and protocatechuic acid producing abilities thereof were examined.

The protocatechuic acid producing ability of each transformant was measured in the following manner. First, each transformant was inoculated in 10 ml of the above-described A-liquid medium (in a test tube) containing glucose 4%, phenylalanine, tyrosine, and tryptophan, 20 μg/ml each, p-amino benzoate 10 μg/ml, shikimate 3.2 mM, and kanamycin 50 μg/ml (in the final concentrations), and thereafter, aerobic shaking culture was performed at 33° C. for 16 to 18 hours.

The bacterial cells grown under the above-described conditions were inoculated in 10 ml of the above-described A-liquid medium (in a test tube) containing glucose 4%, phenylalanine, tyrosine, and tryptophan, 20 μg/ml each, p-amino benzoate 10 μg/ml, shikimate 3.2 mM, and kanamycin 50 μg/ml (in the final concentrations) so that $OD_{610}$ was 0.2, and aerobic shaking culture was performed at 33° C. for 24 hours. After the 24-hour culture, each culture solution was centrifuged (4° C., 15,000×g, 5 minutes), the supernatant obtained was subjected to HPLC analysis, and aromatic-related compounds were subjected to quantitative analysis. The results are shown in Table 10. Consequently, strain PRO34 into which a 3-dehydroshikimate dehydratase gene derived from *Corynebacterium halotolerans* was introduced was found to produce higher concentration of protocatechuic acid, as compared with strain PRO17 into which the same gene of *Corynebacterium glutamicum* was introduced.

TABLE 10

Amounts of produced protocatechuic acid in 24-hour tube culture by *Corynebacterium glutamicum* transformants into which 3-dehydroshikimate dehydrogenase genes derived from various microorganisms were introduced

| Constructed strain | 3-dehydroshikimate dehydratase gene source | Gene | Amount of produced protocatechuic acid (mM) | Amount of produced DHS*[1] (mM) |
|---|---|---|---|---|
| DHS1/pCRB209 | — | — | 0.1 | 29.3 |
| PRO17 | *Corynebacterium glutamicum* | qsuB | 26.4 | ND |
| PRO18 | *Corynebacterium casei* | qsuB | 25.4 | ND |
| PRO19 | *Corynebacterium efficience* | qsuB | 23.9 | ND |
| PRO20 | *Pantoea ananatis* | vllY | 23.7 | ND |
| PRO21 | *Gluconobacter oxydans* | asbF | 1.3 | 19.5 |
| PRO22 | *Pseudomonas putida* | quiC | 9.2 | 13.5 |
| PRO23 | *Rhodopseudomonas palustris* | asbF | 22.9 | 2.1 |
| PRO24 | *Acinetobacter baylyi* | quiC | 2.9 | 18.2 |
| PRO28 | *Alteromonas macleodii* | asbF | 21.3 | 5.5 |
| PRO29 | *Marinobacter hydrocarbonoclasticus* | asbF | 22.0 | 6.9 |
| PRO30 | *Methylobacterium extorquens* | asbF | 20.5 | 0.5 |
| PRO31 | *Neurospora crassa* | qutC | 24.2 | 0.8 |
| PRO32 | *Aspergillus niger* | qutC | 24.8 | ND |
| PRO33 | *Mycobacterium smegmatis* | asbF | 3.0 | 24.6 |
| PRO34 | *Corynebacterium halotolerans* | qsuB | 29.4 | ND |
| PRO37 | *Rhodococcus opacus* | qsuB | 23.1 | 0.1 |
| PRO38 | *Aspergillus oryzae* | qutC | 25.8 | ND |
| PRO39 | *Bacillus thuringiensis* | asbF | 17.3 | 7.4 |

*[1]DHS: 3-dehydroshikimate,
*[2]ND: not detected

Industrial Applicability

With the method of the present invention, protocatechuic acid or a salt thereof can be manufactured from glucose or the like by using microorganisms at practical efficiency.

The invention claimed is:

1. A transformant,
wherein a host of the transformant is a coryneform bacterium,
wherein production of chorismate is not inhibited,
wherein protocatechuic acid-3,4-dioxygenase activity is eliminated, inhibited or reduced,
wherein the transformant has protocatechuic acid producing ability,
and wherein the transformant is subjected to modifications (A), (B), and (C) below:
(A) introducing into the host a gene (a) consisting of a nucleotide sequence of SEQ ID NO: 7, 134, 135, 145, 147, or 149; or (b) consisting of a nucleotide sequence having at least 90% sequence identity to SEQ ID NO: 7, 134, 135, 145, 147, or 149, and encoding a polypeptide having 3-dehydroshikimate dehydratase activity thereby enhancing 3-dehydroshikimate dehydratase activity;

(B) introducing into the host a gene (c) consisting of a nucleotide sequence of SEQ ID NO: 9, 128, or 129; or (d) consisting of a nucleotide sequence having at least 90% sequence identity to SEQ ID NO: 9, 128, or 129, and encoding a polypeptide having chorismate pyruvate lyase activity thereby enhancing chorismate pyruvate lyase activity; and (C) introducing into the host a gene (e) consisting of a nucleotide sequence of SEQ ID NO: 8; or (f) consisting of a nucleotide sequence having at least 90% sequence identity to SEQ ID NO: 8, and encoding a polypeptide having 4-hydroxybenzoate hydroxylase activity thereby enhancing 4-hydroxybenzoate hydroxylase activity.

2. The transformant of claim 1, wherein the gene introduced into the host in modification (A) encodes an enzyme having 3-dehydroshikimate dehydratase activity, and wherein the gene is from a microorganism belonging to the genus *Corynebacterium, Rhodococcus, Bacillus, Rhodopseudomonas, Alteromonas, Marinobacter, Methylobacterium, Pantoea, Neurospora*, or *Aspergillus*.

3. The transformant of claim 2, wherein the gene that encodes the enzyme having 3-dehydroshikimate dehydratase activity is a gene of *Corynebacterium glutamicum, Corynebacterium halotolerans, Corynebacterium casei, Corynebacterium efficiens, Aspergillus niger*, or *Aspergillus oryzae*.

4. The transformant of claim 1, wherein the gene introduced into the host in modification (B) encodes an enzyme having chorismate pyruvate lyase activity, and wherein the gene is from the genus *Providencia* or *Cronobacter*.

5. The transformant of claim 4, wherein the gene that encodes an enzyme having chorismate pyruvate lyase activity is selected from the group consisting of *Providencia rustigianii, Providencia stuartii*, and *Cronobacter sakazakii*.

6. The transformant of claim 1, wherein the gene introduced into the host of modification (C) is *Corynebacterium glutamicum* that encodes an enzyme having 4-hydroxybenzoate hydroxylase activity.

7. The transformant of claim 1, further comprising enhancement of activity of at least one enzyme selected from the group consisting of 3-deoxy-D-arabino-heptulosonate-7-phosphate (DAHP) synthase, 3-dehydroquinate synthase, 3-dehydroquinate dehydratase, shikimate dehydrogenase, shikimate kinase, 5-enolpyruvylshikimate-3-phosphate (EPSP) synthase, and chorismate synthase is enhanced.

8. The transformant of claim 7, wherein the enhancement of DAHP synthase activity is achieved by introducing into a host a DNA of (g) a DNA which consists of a nucleotide sequence of SEQ ID NO: 2; or (h) a DNA which consists of a nucleotide sequence having at least 90% sequence identity with SEQ ID NO: 2, and wherein the DNA encodes a polypeptide having DAHP synthase activity, the enhancement of 3-dehydroquinate synthase activity is achieved by introducing into a host a DNA of (i) a DNA which consists of a nucleotide sequence of SEQ ID NO: 153; or (j) a DNA which consists of a nucleotide sequence having at least 90% sequence identity with SEQ ID NO: 153, and wherein the DNA encodes a polypeptide having 3-dehydroquinate synthase activity, the enhancement of 3-dehydroquinate dehydratase activity is achieved by introducing into a host a DNA of (k) a DNA which consists of a nucleotide sequence of SEQ ID NO: 5; or (l) a DNA which consists of a nucleotide sequence having at least 90% sequence identity with SEQ ID NO: 5, and wherein the DNA encodes a polypeptide having 3-dehydroquinate dehydratase activity, the enhancement of shikimate dehydrogenase activity is achieved by introducing into a host a DNA of (m) a DNA which consists of a nucleotide sequence of SEQ ID NO: 6; or (n) a DNA which consists of a nucleotide sequence having at least 90% sequence identity with SEQ ID NO: 6, and wherein the DNA encodes a polypeptide having shikimate dehydrogenase activity, the enhancement of shikimate kinase activity is achieved by introducing into a host a DNA of (o) a DNA which consists of a nucleotide sequence of SEQ ID NO: 154; or (p) a DNA which consists of a nucleotide sequence having at least 90% sequence identity with SEQ ID NO: 154, and wherein the DNA encodes a polypeptide having shikimate kinase activity, the enhancement of EPSP synthase activity is achieved by introducing into a host a DNA of (q) a DNA which consists of a nucleotide sequence of SEQ ID NO: 155; or (r) a DNA which consists of a nucleotide sequence having at least 90% sequence identity with SEQ ID NO: 155, and wherein the DNA encodes a polypeptide having EPSP synthase activity, and the enhancement of chorismate synthase activity is achieved by introducing into a host a DNA of (s) a DNA which consists of a nucleotide sequence of SEQ ID NO: 156; or (t) a DNA which consists of a nucleotide sequence having at least 90% sequence identity with SEQ ID NO: 156, and wherein the DNA encodes a polypeptide having chorismate synthase activity.

9. The transformant of claim 1, further comprising enhancement of at least one activity selected from the group consisting of transketolase activity and transaldolase activity.

10. The transformant of claim 9, wherein the enhancement of transketolase activity is achieved by introducing a DNA of (u) a DNA which consists of a nucleotide sequence of SEQ ID NO: 151; or (v) a DNA which consists of a nucleotide sequence having at least 90% sequence identity with SEQ ID NO: 151, and wherein the DNA encodes a transketolase, and the enhancement of transaldolase activity is achieved by introducing a DNA of (w) a DNA which consists of a nucleotide sequence of SEQ ID NO: 152; or (x) a DNA which consists of a base sequence having at least 90% sequence identity with SEQ ID NO: 152, and wherein the DNA encodes a transaldolase.

11. The transformant of claim 1, wherein the transformant has simultaneous utilization ability of at least one saccharide selected from the group consisting of glucose, xylose, arabinose, and cellobiose.

12. The transformant of claim 1, wherein the coryneform bacterium as a host is a bacterium of the genus *Corynebacterium*.

13. The transformant of claim 12, wherein the bacterium of the genus *Corynebacterium* as a host is *Corynebacterium glutamicum*.

14. The transformant of claim 13, wherein *Corynebacterium glutamicum* as a host is *Corynebacterium glutamicum* R (FERM BP-18976), ATCC13032, or, ATCC13869.

15. *Corynebacterium glutamicum* PCA4 deposited under Accession Number: NITE BP-02217 for production of protocatechuic acid.

16. A method of producing protocatechuic acid or a salt thereof, wherein the method comprises the step of culturing the host of the transformant of claim 1 in a reaction solution containing a saccharide so as to cause the transformant to produce protocatechuic acid or a salt thereof.

17. The method of claim 16, comprising culturing the host of the transformant under conditions that are aerobic to inhibit growth of the transformant.

\* \* \* \* \*

```
                        SEQUENCE LISTING

<160> NUMBER OF SEQ ID NOS: 162

<210> SEQ ID NO 1
<211> LENGTH: 3341
<212> TYPE: DNA
<213> ORGANISM: Corynebacterium glutamicum

<400> SEQUENCE: 1
atgacgctgt cacctgaact tcaggcgctc actgtacgca attacccctc tgattggtcc      60
gatgtggaca ccaaggctgt agacactgtt cgtgtcctcg ctgcagacgc tgtagaaaac     120
tgtggctccg gccacccagg caccgcaatg agcctggctc cccttgcata caccttgtac     180
cagcgggtta tgaacgtaga tccacaggac accaactggg caggccgtga ccgcttcgtt     240
ctttcttgtg gccactcctc tttgacccag tacatccagc tttacttggg tggattcggc     300
cttgagatgg atgacctgaa ggctctgcgc acctgggatt ccttgacccc aggacaccct     360
gagtaccgcc acaccaaggg cgttgagatc accactggcc ctcttggcca gggtcttgca     420
tctgcagttg gtatggccat ggctgctcgt cgtgagcgtg gcctattcga cccaaccgct     480
gctgagggcg aatccccatt cgaccaccac atctacgtca ttgcttctga tggtgacctg     540
caggaaggtg tcacctctga ggcatcctcc atcgctggca cccagcagct gggcaacatc     600
atcgtgttct gggatgacaa ccgcatctcc atcgaagaca acactgagat cgctttcaac     660
gaggacgttg ttgctcgtta caaggcttac ggctggcaga ccattgaggt tgaggctggc     720
gaggacgttg cagcaatcga agctgcagtg gctgaggcta agaaggacac caagcgacct     780
```

```
accttcatcc gcgttcgcac catcatcggc ttcccagctc caaccatgat gaacaccggt    840
gctgtgcacg gtgctgctct tggcgcagct gaggttgcag caaccaagac tgagcttgga    900
ttcgatcctg aggctcactt cgcgatcgac gacgaggtca tcgctcacac ccgctccctc    960
gcagagcgcg ctgcagagaa gaaggctgca tggcaggtca agttcgatga gtgggcagct   1020
gccaaccctg agaacaaggc tctgttcgat cgcctgaact cccgtgagct tccagcgggc   1080
tacgctgacg agctcccaac atgggatgca gatgagaagg cgtcgcaac  tcgtaaggcg   1140 tccgaggctg cacttcaggc actgggcaag acccttcctg agctgtgggg cggttccgct   1200
gacctcgcag gttccaacaa caccgtgatc aagggctccc cttccttcgg ccctgagtcc   1260
atctccaccg agacctggtc tgctgagcct tacggccgta acctgcactt cggtatccgt   1320
gagcacgcta tgggatccat cctcaacggc atttccctcc acggtggcac ccgcccatac   1380
ggcggaacct tcctcatctt ctccgactac atgcgtcctg cagttcgtct tgcagctctc   1440
atggagaccg acgcttacta cgtctggacc cacgactcca tcggtctggg cgaagatggc   1500
ccaacccacc agcctgttga aaccttggct gcactgcgcg ccatcccagg tctgtccgtc   1560
ctgcgtcctg cagatgcgaa tgagaccgcc caggcttggg ctgcagcact tgagtacaat   1620
gaaggcccta agggtcttgc actgacccgc cagaacgttc ctgttctgga aggcaccaag   1680
gagaaggctg ctgaaggcgt tcgccgcggt ggctacgtcc tggttgaggg ttccaaggaa   1740 acccagatg  tgatcctcat ggctccggc  tccgaggttc agcttgcagt taacgctgcg   1800
aaggctctgg aagctgaggg cgttgcagct cgcgttgttt ccgttccttg catggattgg   1860
ttccaggagc aggacgcaga gtacatcgag tccgttctgc ctgcagctgt gaccgctcgt   1920
gtgtctgttg aagctggcat cgcaatgcct tggtaccgct tcttgggcac ccagggccgt   1980
gctgtctccc ttgagcactt cggtgcttct gcggattacc agaccctgtt tgagaagttc   2040
ggcatcacca ccgatgcagt cgtggcagcg gccaaggact ccattaacgg ttaattgccc   2100
tgctgttttt agcttcaacc cggggcaata tgatcctccg gaattttatt gccccgggtt   2160
gttgttaatc ggtataaagg gtcttaagca catcccttac ttgcctgctc tccttgagcg   2220
cagttcaaga acaattcttt taaggaaaat ttagtttcat gtctcacatt gatgatctgg   2280
cacagctcgg cacttccact tggctcgacg acctctcccg cgagcgcatt acttccggca   2340
atctcagcca ggttattgag gaaaagtctg tagtcggtgt caccaccaac ccagctattt   2400
tcgcagcagc aatgtccaag ggcgattcct acgacgctca gatcgcagag ctcaaggccg   2460
ctggcgcatc tgttgaccag gctgtttacg ccatgagcat cgacgacgtt cgcaatgctt   2520
gtgatctgtt taccggcatc ttcgagtcct ccaacggcta cgacggccgc gtgtccatcg   2580
aggttgaccc acgtatctct gcggaccgcg acgcaaccct ggctcaggcc aaggagctgt   2640
gggcaaaggt tgatcgtcca aacgtcatga tcaagatccc tgctaccca  ggttctttgc   2700 cagcaatcac cgacgctttg gctgagggca tcagtgttaa cgtcaccttg atcttctccg   2760
ttgctcgcta ccgcgaagtc atcgctgcgt tcatcgaggg catcaagcag gcagctgcaa   2820
acggccacga cgtatccaag atccactctg tggcttcctt cttcgtctcc cgcgtcgacg   2880
ttgagatcga caagcgcctc gaggcaatcg gatccgatga ggctttggct ctgcgtggca   2940
aggcaggcgt tgccaacgct cagcgcgctt acgctgtgta caaggagctt ttcgacgccg   3000
ccgagctgcc tgaaggcgcc aacactcagc gcccactgtg ggcatccacc ggcgtgaaga   3060
accctgcgta cgctgcaact ctttacgttt ccgagctggc tggtccaaac accgtcaaca   3120
ccatgccaga aggcaccatc gacgctgttc tggaactggg caacctgcac ggtgacaccc   3180
```

-continued

| | |
|---|---|
| tgtccaactc cgcggcagaa gctgacgctg tgttctccca gcttgaggct ctgggcgttg | 3240 |
| acttggcaga tgtcttccag gtcctggaga ccgagggcgt ggacaagttc gttgcttctt | 3300 |
| ggagcgaact gcttgagtcc atggaagctc gcctgaagta g | 3341 |

<210> SEQ ID NO 2
<211> LENGTH: 1053
<212> TYPE: DNA
<213> ORGANISM: Escherichia coli

<400> SEQUENCE: 2

| | |
|---|---|
| atgaattatc agaacgacga tttacgcatc aaagaaatca agagttact tcctcctgtc | 60 |
| gcattgctgg aaaaattccc cgctactgaa aatgccgcga atacggttgc ccatgcccga | 120 |
| aaagcgatcc ataagatcct gaaaggtaat gatgatcgcc tgttggttgt gattggccca | 180 |
| tgctcaattc atgatcctgt cgcggcaaaa gagtatgcca ctcgcttgct ggcgctgcgt | 240 |
| gaagagctga agatgagct ggaaatcgta atgcgcgtct attttgaaaa gccgcgtacc | 300 |
| acggtgggct ggaaagggct gattaacgat ccgcatatgg ataatagctt ccagatcaac | 360 |
| gacggtctgc gtatagcccg taaattgctg cttgatatta cgacagcgg tctgccagcg | 420 |
| gcaggtgagt ttctcgatat gatcaccca caatatctcg ctgacctgat gagctggggc | 480 |
| gcaattggcg cacgtaccac cgaatcgcag gtgcaccgcg aactggcatc agggctttt | 540 |
| tgtccggtcg gcttcaaaaa tggcaccgac ggtacgatta agtggctat cgatgccatt | 600 |
| aatgccgccg gtgcgccgca ctgcttcctg tccgtaacga aatgggggca ttcggcgatt | 660 |
| gtgaatacca gcggtaacgg cgattgccat atcattctgc gcggcggtaa agagcctaac | 720 |
| tacagcgcga agcacgttgc tgaagtgaaa gaagggctga caaagcagg cctgccagca | 780 |
| caggtgatga tcgatttcag ccatgctaac tcgtccaaac aattcaaaaa gcagatggat | 840 |
| gtttgtgctg acgtttgcca gcagattgcc ggtggcgaaa aggccattat ggcgtgatg | 900 |
| gtggaaagcc atctggtgga aggcaatcag agcctcgaga gcggggagcc gctggcctac | 960 |
| ggtaagagca tcaccgatgc ctgcatcggc tgggaagata ccgatgctct gttacgtcaa | 1020 |
| ctggcgaatg cagtaaaagc gcgtcgcggg taa | 1053 |

<210> SEQ ID NO 3
<211> LENGTH: 2964
<212> TYPE: DNA
<213> ORGANISM: Corynebacterium glutamicum

<400> SEQUENCE: 3

| | |
|---|---|
| atgctaggca tgcttcgatg gactacagca ggtgaatccc acggccaggc gcttatcgcc | 60 |
| acggttgaac acatgccagc aggcgtgccc gtgactaaag atgaggtctc gtatcaattg | 120 |
| gcgcgccgac gccttggata tggtcgcggc gctcgcatga gtttgagca agacgcgttg | 180 |
| accttcctga ccggcatccg ccacggcctc actttgggta gccccatctc aatcatgatc | 240 |
| ggcaacactg agtgggataa gtggaccacc atcatgtcct ctgacgcttt ggacatggaa | 300 |
| gacccagaca cgttgcggc gatgtcttcg ggtcgcggtg caaaactgac tcgtccgcgt | 360 |
| ccaggccacg cagattacgc aggcatgctc aagtacggat cgatgatgc ccgcaacgtg | 420 |
| ctggagcgtt cttcagcccg tgagacggca gctcgcgtgg cagcagcaac cgttgcgcgt | 480 |
| tccttcctcc gtgaaacctt gggcgtggag gtgctctctc acgtaatttc cattggtgcg | 540 |
| tccgagcctt acgtcggcgc ggagccaacc tttgcagata ttcaagcaat cgatgattcc | 600 |

```
ccagttcgtg cattcggtaa agacgctgaa aaatccatga tcgcggaaat cgaggccgca      660
aagaaagccg gcgataccct cggtggcatc gtggaagtga ttgttgaagg cctacccatc      720
ggtttgggct cacacatttc tggcgaagat cgcctcgatg cgcagatcgc agctgcactc      780
atgggcattc aggccatcaa gggcgtggaa atcggtgacg gtttcgaaga agctcgtcga      840
cgtggctccg aagcccacga tgaagtgttc ctggatgaca acggcgtata ccgcaacacc      900
aaccgtgcag gtggcctcga aggcggcatg accaacggtg aaaccctgcg cgttcgtgct      960
ggcatgaagc caatttctac tgtgcctcgc gccctgaaaa ccattgatat ggaaaacggc     1020
aaggcagcaa ccggaatcca ccagcgttcc gacgtgtgcg ctgttccagc cgccggtgtc     1080
gttgcagaag caatggtcac cctggttctc gcccgcgcag tcctgcagaa attcggcggt     1140
gactccctga gtgaaaccaa gagcaacatt gacacctacc tcaaaaacat tgaggaacga     1200
atgaaattcg aaggtttaga ggatggagcg taatgaagtg aatgatcaaa ttcacttaga     1260
tcatcaatca gatgacacct ctgaatgctc ctgcccgatc gtggttcttg tgggtttgcc     1320
aggagctgga aaatccacca ttggacgtcg attagcgcgc gccttaaaca ctgaactcgt     1380
cgactccgac gaactcattg agcgcgccac cggaaaagcc tgcggcgccg tgttcagcga     1440
gctcggcgag ccagccttcc gcgagctcga ggccatccac gtggccgaag cactgaaatc     1500
ctccggagtg gtgagcttgg gaggcggatc tgtgctgaca gaatccaccc gtgaactgct     1560
caaaggccac gacgtggtct ggatcgacgt gccagtagaa aaggcatca ggcgcaccgc       1620
aaacgagcgt tcccgccccg tgctgcaagc cgccgacccc gccgagcact accgcaacct     1680
ggtgaaagtg cgcaccccgt tgtacgaaga ggtggcaacc taccgacttc gcaccaacaa     1740
ccgcagcccc cagcaagtgg tggcagcagt gttgcatcat ctagaaatcg attaattaaa     1800
ccgggcacct gattaacatt gggctgcccg gtttcttcct attacaagcg aaaggcaacg     1860
tgccccatga gcgcagcgca gattttcaac accgtccacg tcaatggatc ttcccccctat    1920
gatgtccaca ttggttccgg cctcaacgag ctcattgttc agcgcgcagc ggaatcaggc     1980
gcggagcagg tagcgatttt gcaccagccc agcatggatg acattgcatc cgagttggat     2040
gcagcactag tcgctgctgg tttgaaggtc ctgcaccta atgttcccga tgcggaaaac      2100
ggcaagtcct tggaagtagc ggggcagtgc tgggatgaat tgggtggcgc agcattcggc     2160
cgccgcgata tcgtcatcgg acttggtggc ggtgctgcca cagatctcgc gggattcgtc     2220
gctgctgcgt ggatgcgtgg cgtgcgcgtc attcaggttc caaccacctt gttggccatg     2280
gtggacgctg cggtgggcgg caagactggc atcaataccg ccgcaggcaa gaaccttgtg     2340
ggcgcgttcc acgagcctga cgcagtattc attgacaccg aacgcctagc caccctgcct     2400
gacgcggaaa tcatcgcggg atccgccgaa atcatcaaaa ctggtttcat cgccgaccca     2460
gaaatcctgc gcctttacga aactgatccc gcagcctgcc tgaagaaaga agtcgaaggc     2520
tcccacctac ctgaactgat ttggcgctcc gtcaccgtca agggctccgt ggtcggccaa     2580
gacctcaaag aatctagcct gcgcgaaatc ctcaactacg acacaccttt gcccacgcc      2640
gtcgaactcc gcgaaaactt ccgctggcgc cacggcaatg ccgttgcagt gggcatgatg     2700
ttcatcgcta acctctccca aagctcgggc cttatcgacg cgccctcct cgagcgccac      2760
cgctcaatcc tggcggccat cggtctgccc acttcctacg aaggcggagc cttcgacgag     2820
ctttacgacg gcatgacccg cgacaagaaa aaccgcgacg gcaacatccg cttcgtcgca     2880
ctgaccgccg tgggcgaggt tacccgcatt gaggggccct caaaacaaga tttacagagt     2940
gcttatgagg caatcagcca ctaa                                            2964
```

<210> SEQ ID NO 4
<211> LENGTH: 1293
<212> TYPE: DNA
<213> ORGANISM: Corynebacterium glutamicum

<400> SEQUENCE: 4

| | | |
|---|---|---|
| atggtctttg tgtctgattc gtctatctct ttgcccattt gggatgctcc gcgcgctcgc | 60 |
| ggccccatag tctcggacct ggctatccct ggttccaagt cgatcaccaa ccgcgccctc | 120 |
| atcttggctg cgctcgcatc aactccatcc accatcattg atgtccttcg tagtcgtgat | 180 |
| accgatctca tgactgatgg tctacgcagc ctcggaatca ccattactga agaggcagtc | 240 |
| gatcgctacc gcgttgagcc cggacagttg tctgctggct ccgttgagtg tggtcttgct | 300 |
| ggtacggtca tgcgcttttt gcctcctgtt gctgctttcg ctgatggtcc tgttcatttt | 360 |
| gatggcgatc ctcaagctcg tgttcgtccg atgaccagca ttttggatgc gctgcgttcg | 420 |
| cttggtgtgg aggtggacaa caacaatctg cctttcactg ttaatgctgg tgaggtccct | 480 |
| gagggtggcg tggttgagat tgatgcttcc ggctcatctc agtttgtttc tggtcttttg | 540 |
| cttcagcgc ctcgttttaa aaatggcgtc accgttaagc acgtcggtgg tcgtctgccg | 600 |
| agcatgccgc atattgagat gaccgtcgat atgcttcgtt ccgcaggcat tgagatcgaa | 660 |
| gagtcagaaa tcagtgggt tgttcatcct ggtgagatct gggtcggac ctggcgcatt | 720 |
| gagccggatc tttctaatgc gactccgttc ctagctgccg ctgcggtcac tggtggaacc | 780 |
| atcaagatta tcactggcc aatcaaaact actcagcctg gcgatgctat tcgttcgatt | 840 |
| cttgagcgca tgggctgcga agttgagctg gttgctcagg gtgaaggtta cgatctgtcg | 900 |
| gtgactggtc cggttgctct caagggcatt gagatcgata tgtccgatat cggtgagttg | 960 |
| accctaccg tggcggcgtt ggctgcgttg gcgtcgacag agtctcgttt gaccggtatt | 1020 |
| gctcatcttc gtggccatga gacggatcgt ttggctgcgt tgactgcgga gatcaacaaa | 1080 |
| cttggtggaa agtgcactga gcttaaggat ggtctgttga ttgagcctgc gtcgctgcac | 1140 |
| ggtggtgtgt ggcattcata tgctgatcat cgtatggcta ctgctggtgc gatcattggc | 1200 |
| ctcgcggttg atgacgttca ggttgaagac attaagacca cttccaagac tttccctggt | 1260 |
| tttgaaaatg tttgggagga gatggttggc tag | 1293 |

<210> SEQ ID NO 5
<211> LENGTH: 438
<212> TYPE: DNA
<213> ORGANISM: Corynebacterium glutamicum

<400> SEQUENCE: 5

| | | |
|---|---|---|
| atgcttggaa aaattctcct cctcaacggc ccaaacctga acatgctggg caaacgcgag | 60 |
| cctgacattt acggacacga caccttggaa gacgtcgtcg cgctggcaac cgctgaggct | 120 |
| gcgaagcacg gccttgaggt tgaggcgctc cagagcaatc acgaaggtga gctaatcgat | 180 |
| gcgctgcaca acgctcgcgg cacccacatc ggttgcgtga ttaaccccgg cggcctgact | 240 |
| cacacttcgg tggcgctttt ggatgcggtg aaggcgtctg agcttcctac cgttgaggtg | 300 |
| cacatttcca atccgcatgc ccgtgaagag ttccgccacc attcttacat ttccctcgcc | 360 |
| gcggtctccg ttatcgctgg cgctggcatc cagggttacc gtttcgcggt cgatatcctg | 420 |
| gcaaatctca aaaagtag | 438 |

<210> SEQ ID NO 6

```
<211> LENGTH: 831
<212> TYPE: DNA
<213> ORGANISM: Corynebacterium glutamicum

<400> SEQUENCE: 6
atgggttctc acatcactca ccgggcggcc gtactcggct cacccatcga gcattccaaa      60
tccccagtcc tccacaacac cggctataaa gccctcggac tggaccaatg ggaatacgac     120
cgctttgagt gcaccggcga catgctcccc ggaatcgtct ccggcgctga tgaaacctac     180
cgcggattct ccgtcactat gccgtccaaa ttcgcagccc tcgaattcgc cgacgaagta     240
accgaacgcg cccgcgccat cggctccgca aacacacttc tgcgcaccga accggatgg      300 cgcgcagaca caccgacgt cgacggcatc aggggagccc tcggtgaact cctcggcagc     360
gcatcactgg ccgcaaaca cgccatcgtc atcggctccg gcggcaccgc acgcccgcc      420 atctgggcac tcatcgaagc cggggtcgcg cggatcacgg tgctcaaccg ctccgatcga     480
accgccgaac tgcaaacgct tttcgacgaa accccacca ccttggccta cgccccgctc     540
gaacatctcg acatcgaagc cgacgtcgta gtctctacag tgccctccgc agcaatcgca     600
ggcctcgaag acacactcgc aatcgcccca gtcctcgacg tcatctacga tccttggcca     660
acaccactcg tagaagtcgc acgagccaaa ggtctcaaag ctgtcggagg ccacgtcatg     720
ctggcacacc agtcctacgg acagtttgaa caattcaccg gaatggatgc accccgcgat     780
gctatgcgtg aggctttgga agaatcccta ggcatctcgg aagaacacta g             831

<210> SEQ ID NO 7
<211> LENGTH: 1857
<212> TYPE: DNA
<213> ORGANISM: Corynebacterium glutamicum

<400> SEQUENCE: 7
atgcgtacat ccattgccac tgtttgtttg tccggaactc ttgctgaaaa gctgcgcgca      60
gctgcagatg ctggatttga tggtgtggaa atcttcgagc aggacttggt ggtttccccg     120
cattcggcag agcagattcg tcagcgggct caggatttgg gattaaccct ggatctgttc     180
cagccgtttc gagatttcga aggtgtgaa gaagagcagt ttctgaagaa tctgcaccgc     240
ttggaagaga agttcaagct gatgaacagg cttggcattg agatgatctt gttgtgttcc     300
aatgtgggca ccgcgaccat caatgatgat gaccttttcg tggagcagtt gcatcgtgca     360
gcagatttgg ctgagaagta caacgtcaag attgcttatg aagcgttggc gtggggcaag     420
tttgtcaatg attttgagca tcgcatgca cttgtggaga aggtgaatca aaggcgctg      480 ggaacctgct tggatacgtt ccatattctt tcccgtggtt gggaaaccga cgaggtggaa     540
aacatcccgg cggagaagat cttctttgtt cagttggcgg atgcaccgaa gctgagcatg     600
gacattttgt cctggtcgcg tcaccaccgt gttttccctg gtgaaggcga tttcgatctg     660
gtgaaattca tggttcatct ggccaagacg ggttatgatg cccgatttc tttggagatc     720 ttcaacgatt ccttccgcaa ggccgaggtt ggtcgcaccg cgattgatgg gttgcgttct     780
ttgcgttggt tggaagatca gacctggcat gcgctaaatg ctgaggatcg tccaagcgca     840
ctagagctgc gtgcacttcc tgaggtcgcg gaacctgaag cgttgattt cattgagatc     900 gccactggac gtttgggtga gaccattcgg gttcttcatc aattgggttt ccgcttgggt     960
ggtcatcact gcagtaagca ggattaccag gtatggaccc agggcgatgt gcgcattgtg    1020
gtgtgtgatc gtggggccac cggggctcca accacgatct ctgcgatggg cttttgacacc   1080 cctgatccag aagccgcgca tgcccgtgcg gaattgctgc gggctcagac aattgatcgt    1140
```

-continued

```
ccccacatcg agggtgaagt tgaccttaaa ggtgtgtacg cgccggatgg ggtggagctg    1200 ttttttcgcgg ggccgagccc cgatggaatg cccgagtggc tgccggaatt cggcgtcgaa    1260
aagcaagaag ctggtctcat tgaagccatc gaccacgtca atttcgccca gccatggcaa    1320
cattttgatg aggcagtgct gttttacacc gcgctgatgg cgttagagac tgtgcgtgag    1380
gatgagttcc cgagcccaat tggtttggtg cgcaatcagg tgatgcgttc gccgaatgat    1440
gcggtgcggt tgctgctcag cgtggcgccg aggacggtg agcagggaga tttcctcaac    1500
gcggcctacc cggagcacat tgcgttggcc acggcggaca tcgtggcggt ggctgaacgt    1560
gcgcgcaaac gaggcctgga tttcttgccc gtcccagaga attactacga cgatgtgcag    1620
gcgcgttttg atttgccgca ggaattcttg gacacactca aggaaaacca cctgctttac    1680
gactgcgacg agaacggcga attcctccac ttttacaccc gcacgttggg cacgctgttc    1740
ttcgaagtgg tggaacgccg cggcggtttt gcaggttggg gcgaaacaaa cgctccggtg    1800
cggttagcgg cgcagtatcg tgaggtgcgg gacctcgagc ggggaatccc caactag     1857

<210> SEQ ID NO 8
<211> LENGTH: 1188
<212> TYPE: DNA
<213> ORGANISM: Corynebacterium glutamicum

<400> SEQUENCE: 8
atgaaccacg taccagtggc aattattggc gcaggaccag caggactgac cctcgcccac      60
ctcctccacc ttcaaggtgt ggaatcaatc gtctttgaat cccgcacccg caaggacgtc     120
gaagaaaccg tccgagcagg cattctggaa caaggcaccc tgaatctgat gcgcgaaacc     180
ggagtcggcg cacgcatgga agcagaagcc gatcacgatg aagcaatcga catctccatc     240
aacaatgagc gcacccgcat tccgctgacc gaactcaccg gccacaaggt tgcgatctac     300
ccgcagcacg aatacctcaa agatttcatt gccaagcgca tcgaagacgg cggcgaactc     360
cttttcacca ccactgttga ttccgtagag aactacgaag gcgacctcgc caaggtgacc     420
tacaccgaag ccgatggttc ctccaccacc atcaccgccg actacgtcat cgcagctgac     480
ggctccaact cccccttaccg caagttgatc accgaagacg gcggcgtgcg cgcccgccat     540
gaatacccct tacgcatggt tcggcatttttg gtcgaagcac caaaaaccca aaaggaactc     600
atctacgcaa cccaccctga gggctttgcg ctgatctcca cccgcaccga tgaaatccag     660
cgctactacc tgcagtgcaa cccagacgac accccagaca tgtggtccga tgaccgcatt     720
tgggaacagc tgcatctgcg tgcggactcc cctggcatca ccgtgtctga agggcgcatc     780
tttgacaagg ccgtgctgcg tttccgctcc gcggtcaccg aaccaatgca aaagggacgc     840
ctcttccttg ctggcgatgc tgcacacacc gtgccgccaa ccggagctaa gggcctcaac     900
ttggctgttg ccgatgtcgc agtactcgcg ccagcactgg ttcgtgccct gaagaagaag     960
gacaccggct tgctcgatag ctacacctcc ctggcagtcc ccgcatctg gaaagcacag    1020 cacttctcct actggatgag ctccatgctc cacgcagtac ccggcgaaga tcactttgcc    1080
acccagcgcc gattcgctga attgcgctcc gtcctagaat cccaatccgg ccaacgctac    1140
ctcgcagagc agtacgttgg gcgcgaccta ccacgcttcg aggtataa                1188

<210> SEQ ID NO 9
<211> LENGTH: 504
<212> TYPE: DNA
<213> ORGANISM: Providencia rustigianii
```

<400> SEQUENCE: 9

```
atgcatgaaa caatttttac ccatcatccc attgattggc taaacgagga tgatgagtca      60
gttcctaaca gtgtactaga ttggctgcaa gagcgtggtt caatgactaa acggttcgag     120
cagcattgcc aaaaagtcac ggtaattccc tatttagagc gctatatcac tccagagatg     180
ctgagcgctg atgaagccga gcgtttaccc gaaagtcaac gttactggtt gcgagaagtc     240
attatgtatg gggataatat tccgtggttg ataggcagaa cattgatccc tgaagagacc     300
ctcaccaacg atgataaaaa gctggtggac attggtcgtg tgccattagg gcgttacctt     360
tttagtcatg atagtcttac ccagagattat attgatattg caccagtgc ggatcgttgg     420
gtgcgacgtt ctctgctgag attatctcaa aagcccttat tattaactga aatattttta     480
cctgaatcac ctgcatatag ataa                                            504
```

<210> SEQ ID NO 10
<211> LENGTH: 26
<212> TYPE: DNA
<213> ORGANISM: Artificial sequence
<220> FEATURE:
<223> OTHER INFORMATION: PCR primer

<400> SEQUENCE: 10

```
ctctcatatg acgctgtcac ctgaac                                           26
```

<210> SEQ ID NO 11
<211> LENGTH: 28
<212> TYPE: DNA
<213> ORGANISM: Artificial sequence
<220> FEATURE:
<223> OTHER INFORMATION: PCR primer

<400> SEQUENCE: 11

```
ctctcatatg ctacttcagg cgagcttc                                         28
```

<210> SEQ ID NO 12
<211> LENGTH: 37
<212> TYPE: DNA
<213> ORGANISM: Artificial sequence
<220> FEATURE:
<223> OTHER INFORMATION: PCR primer

<400> SEQUENCE: 12

```
ctctgatatc atgaattatc agaacgacga tttacgc                               37
```

<210> SEQ ID NO 13
<211> LENGTH: 30
<212> TYPE: DNA
<213> ORGANISM: Artificial sequence
<220> FEATURE:
<223> OTHER INFORMATION: PCR primer

<400> SEQUENCE: 13

```
ctctgatatc gacttatcag gcctgtggtg                                       30
```

<210> SEQ ID NO 14
<211> LENGTH: 24
<212> TYPE: DNA
<213> ORGANISM: Artificial sequence
<220> FEATURE:
<223> OTHER INFORMATION: PCR primer

<400> SEQUENCE: 14

```
tttgtccggt cggcttcaaa aatg                                             24
```

<210> SEQ ID NO 15
<211> LENGTH: 19
<212> TYPE: DNA
<213> ORGANISM: Artificial sequence
<220> FEATURE:
<223> OTHER INFORMATION: PCR primer

<400> SEQUENCE: 15
aaagccctga tgccagttc                                                19

<210> SEQ ID NO 16
<211> LENGTH: 31
<212> TYPE: DNA
<213> ORGANISM: Artificial sequence
<220> FEATURE:
<223> OTHER INFORMATION: PCR primer

<400> SEQUENCE: 16
ctctcatatg ttacgctcca tcctctaaac c                                  31

<210> SEQ ID NO 17
<211> LENGTH: 33
<212> TYPE: DNA
<213> ORGANISM: Artificial sequence
<220> FEATURE:
<223> OTHER INFORMATION: PCR primer

<400> SEQUENCE: 17
ctctcatatg ttagtggctg attgcctcat aag                                33

<210> SEQ ID NO 18
<211> LENGTH: 29
<212> TYPE: DNA
<213> ORGANISM: Artificial sequence
<220> FEATURE:
<223> OTHER INFORMATION: PCR primer

<400> SEQUENCE: 18
ctctccatgg tctttgtgtc tgattcgtc                                     29

<210> SEQ ID NO 19
<211> LENGTH: 28
<212> TYPE: DNA
<213> ORGANISM: Artificial sequence
<220> FEATURE:
<223> OTHER INFORMATION: PCR primer

<400> SEQUENCE: 19
ctctccatgg ctagccaacc atctcctc                                      28

<210> SEQ ID NO 20
<211> LENGTH: 31
<212> TYPE: DNA
<213> ORGANISM: Artificial sequence
<220> FEATURE:
<223> OTHER INFORMATION: PCR primer

<400> SEQUENCE: 20
ctctcatatg cttggaaaaa ttctcctcct c                                  31

<210> SEQ ID NO 21
<211> LENGTH: 37
<212> TYPE: DNA
<213> ORGANISM: Artificial sequence
<220> FEATURE:

-continued

<223> OTHER INFORMATION: PCR primer

<400> SEQUENCE: 21
ctctcatatg ctactttttg agatttgcca ggatatc                              37

<210> SEQ ID NO 22
<211> LENGTH: 28
<212> TYPE: DNA
<213> ORGANISM: Artificial sequence
<220> FEATURE:
<223> OTHER INFORMATION: PCR primer

<400> SEQUENCE: 22
ctctcatatg ggttctcaca tcactcac                                        28

<210> SEQ ID NO 23
<211> LENGTH: 30
<212> TYPE: DNA
<213> ORGANISM: Artificial sequence
<220> FEATURE:
<223> OTHER INFORMATION: PCR primer

<400> SEQUENCE: 23
ctctcatatg ctagtgttct tccgagatgc                                      30

<210> SEQ ID NO 24
<211> LENGTH: 30
<212> TYPE: DNA
<213> ORGANISM: Artificial sequence
<220> FEATURE:
<223> OTHER INFORMATION: PCR primer

<400> SEQUENCE: 24
ctttgaccat atgcgtacat ccattgccac                                      30

<210> SEQ ID NO 25
<211> LENGTH: 34
<212> TYPE: DNA
<213> ORGANISM: Artificial sequence
<220> FEATURE:
<223> OTHER INFORMATION: PCR primer

<400> SEQUENCE: 25
ctagttccat atgctagttg gggattcccc gctc                                 34

<210> SEQ ID NO 26
<211> LENGTH: 26
<212> TYPE: DNA
<213> ORGANISM: Artificial sequence
<220> FEATURE:
<223> OTHER INFORMATION: PCR primer

<400> SEQUENCE: 26
ctctcatatg aaccacgtac cagtgg                                          26

<210> SEQ ID NO 27
<211> LENGTH: 31
<212> TYPE: DNA
<213> ORGANISM: Artificial sequence
<220> FEATURE:
<223> OTHER INFORMATION: PCR primer

<400> SEQUENCE: 27
ctctcatatg ttatacctcg aagcgtggta g                                    31

<210> SEQ ID NO 28
<211> LENGTH: 36
<212> TYPE: DNA
<213> ORGANISM: Artificial sequence
<220> FEATURE:
<223> OTHER INFORMATION: PCR primer

<400> SEQUENCE: 28
ctctcatatg catgaaacaa tttttaccca tcatcc                              36

<210> SEQ ID NO 29
<211> LENGTH: 42
<212> TYPE: DNA
<213> ORGANISM: Artificial sequence
<220> FEATURE:
<223> OTHER INFORMATION: PCR primer

<400> SEQUENCE: 29
ctctcatatg gattatgtta gatagttatc tatatgcagg tg                       42

<210> SEQ ID NO 30
<211> LENGTH: 30
<212> TYPE: DNA
<213> ORGANISM: Artificial sequence
<220> FEATURE:
<223> OTHER INFORMATION: PCR primer

<400> SEQUENCE: 30
ctctgtcgac cttattcgtc gtagtgccag                                     30

<210> SEQ ID NO 31
<211> LENGTH: 30
<212> TYPE: DNA
<213> ORGANISM: Artificial sequence
<220> FEATURE:
<223> OTHER INFORMATION: PCR primer

<400> SEQUENCE: 31
ctctgtcgac atcatcgcgg tgtcacagtt                                     30

<210> SEQ ID NO 32
<211> LENGTH: 26
<212> TYPE: DNA
<213> ORGANISM: Artificial sequence
<220> FEATURE:
<223> OTHER INFORMATION: PCR primer

<400> SEQUENCE: 32
ctctagatct catgggcaac tcctcg                                         26

<210> SEQ ID NO 33
<211> LENGTH: 29
<212> TYPE: DNA
<213> ORGANISM: Artificial sequence
<220> FEATURE:
<223> OTHER INFORMATION: PCR primer

<400> SEQUENCE: 33
ctctagatct atgcttgtca catgaggcg                                      29

<210> SEQ ID NO 34
<211> LENGTH: 33
<212> TYPE: DNA
<213> ORGANISM: Artificial sequence
<220> FEATURE:
<223> OTHER INFORMATION: PCR primer

<400> SEQUENCE: 34
ctctcctgca ggctgaccag gatttatctg tcc         33

<210> SEQ ID NO 35
<211> LENGTH: 31
<212> TYPE: DNA
<213> ORGANISM: Artificial sequence
<220> FEATURE:
<223> OTHER INFORMATION: PCR primer

<400> SEQUENCE: 35
ctctcctgca gggatcgtca ccttccaaac c           31

<210> SEQ ID NO 36
<211> LENGTH: 29
<212> TYPE: DNA
<213> ORGANISM: Artificial sequence
<220> FEATURE:
<223> OTHER INFORMATION: PCR primer

<400> SEQUENCE: 36
ctctagatct tctaggccag gaactaacg              29

<210> SEQ ID NO 37
<211> LENGTH: 27
<212> TYPE: DNA
<213> ORGANISM: Artificial sequence
<220> FEATURE:
<223> OTHER INFORMATION: PCR primer

<400> SEQUENCE: 37
ctctagatct gaagggtgct tcgcttc                27

<210> SEQ ID NO 38
<211> LENGTH: 34
<212> TYPE: DNA
<213> ORGANISM: Artificial sequence
<220> FEATURE:
<223> OTHER INFORMATION: PCR primer

<400> SEQUENCE: 38
ctctcctgca gggtggatac aaatgggatg tctg        34

<210> SEQ ID NO 39
<211> LENGTH: 32
<212> TYPE: DNA
<213> ORGANISM: Artificial sequence
<220> FEATURE:
<223> OTHER INFORMATION: PCR primer

<400> SEQUENCE: 39
ctctcctgca gggatgaagt tgctgaagca gg          32

<210> SEQ ID NO 40
<211> LENGTH: 28
<212> TYPE: DNA
<213> ORGANISM: Artificial sequence
<220> FEATURE:
<223> OTHER INFORMATION: PCR primer

<400> SEQUENCE: 40
ctctgtcgac cagatggcag ttgaggtg               28

<210> SEQ ID NO 41
<211> LENGTH: 30

```
<212> TYPE: DNA
<213> ORGANISM: Artificial sequence
<220> FEATURE:
<223> OTHER INFORMATION: PCR primer

<400> SEQUENCE: 41
ctctgtcgac cgatcagtgg agatcaacac                                    30

<210> SEQ ID NO 42
<211> LENGTH: 30
<212> TYPE: DNA
<213> ORGANISM: Artificial sequence
<220> FEATURE:
<223> OTHER INFORMATION: PCR primer

<400> SEQUENCE: 42
ctctgtcgac attcctgcgt ctggtggtct                                    30

<210> SEQ ID NO 43
<211> LENGTH: 30
<212> TYPE: DNA
<213> ORGANISM: Artificial sequence
<220> FEATURE:
<223> OTHER INFORMATION: PCR primer

<400> SEQUENCE: 43
ctctgtcgac ccgaccaatg atgtaactgc                                    30

<210> SEQ ID NO 44
<211> LENGTH: 33
<212> TYPE: DNA
<213> ORGANISM: Artificial sequence
<220> FEATURE:
<223> OTHER INFORMATION: PCR primer

<400> SEQUENCE: 44
ctctgtcgac ctgtggtgac tttattgtct agg                                33

<210> SEQ ID NO 45
<211> LENGTH: 31
<212> TYPE: DNA
<213> ORGANISM: Artificial sequence
<220> FEATURE:
<223> OTHER INFORMATION: PCR primer

<400> SEQUENCE: 45
ctctgtcgac gccagcttct gtaagtaact c                                  31

<210> SEQ ID NO 46
<211> LENGTH: 41
<212> TYPE: DNA
<213> ORGANISM: Artificial sequence
<220> FEATURE:
<223> OTHER INFORMATION: PCR primer

<400> SEQUENCE: 46
ctctagatct gtgctgatct taatattgaa tcgttttatt c                       41

<210> SEQ ID NO 47
<211> LENGTH: 30
<212> TYPE: DNA
<213> ORGANISM: Artificial sequence
<220> FEATURE:
<223> OTHER INFORMATION: PCR primer

<400> SEQUENCE: 47
```

-continued ctctagatct gactactgtg agtggcttga                30

<210> SEQ ID NO 48
<211> LENGTH: 30
<212> TYPE: DNA
<213> ORGANISM: Artificial sequence
<220> FEATURE:
<223> OTHER INFORMATION: PCR primer

<400> SEQUENCE: 48
ctctgcatgc tcaacgagct gatggagctt                30

<210> SEQ ID NO 49
<211> LENGTH: 30
<212> TYPE: DNA
<213> ORGANISM: Artificial sequence
<220> FEATURE:
<223> OTHER INFORMATION: PCR primer

<400> SEQUENCE: 49
ctctgcatgc cgtggtgtat ctgtaactgc                30

<210> SEQ ID NO 50
<211> LENGTH: 30
<212> TYPE: DNA
<213> ORGANISM: Artificial sequence
<220> FEATURE:
<223> OTHER INFORMATION: PCR primer

<400> SEQUENCE: 50
ctcttctaga agacatcgga gcaatcggct                30

<210> SEQ ID NO 51
<211> LENGTH: 30
<212> TYPE: DNA
<213> ORGANISM: Artificial sequence
<220> FEATURE:
<223> OTHER INFORMATION: PCR primer

<400> SEQUENCE: 51
ctcttctaga gtccgcagag gaaccattca                30

<210> SEQ ID NO 52
<211> LENGTH: 30
<212> TYPE: DNA
<213> ORGANISM: Artificial sequence
<220> FEATURE:
<223> OTHER INFORMATION: PCR primer

<400> SEQUENCE: 52
ctctgagctc gtgaacatat cggcatcgag                30

<210> SEQ ID NO 53
<211> LENGTH: 30
<212> TYPE: DNA
<213> ORGANISM: Artificial sequence
<220> FEATURE:
<223> OTHER INFORMATION: PCR primer

<400> SEQUENCE: 53
ctctgtcgac ctatggcgtt ctatactgcg                30

<210> SEQ ID NO 54
<211> LENGTH: 30
<212> TYPE: DNA
<213> ORGANISM: Artificial sequence

```
<220> FEATURE:
<223> OTHER INFORMATION: PCR primer

<400> SEQUENCE: 54
ctcttctaga tatgcaagaa gcaagcaagt                                30

<210> SEQ ID NO 55
<211> LENGTH: 30
<212> TYPE: DNA
<213> ORGANISM: Artificial sequence
<220> FEATURE:
<223> OTHER INFORMATION: PCR primer

<400> SEQUENCE: 55
ctctctcgag tctcataaaa gttctccgat                                30

<210> SEQ ID NO 56
<211> LENGTH: 28
<212> TYPE: DNA
<213> ORGANISM: Artificial sequence
<220> FEATURE:
<223> OTHER INFORMATION: PCR primer

<400> SEQUENCE: 56
atgcatgcac gtactccgaa gatgtatg                                  28

<210> SEQ ID NO 57
<211> LENGTH: 28
<212> TYPE: DNA
<213> ORGANISM: Artificial sequence
<220> FEATURE:
<223> OTHER INFORMATION: PCR primer

<400> SEQUENCE: 57
atgcatgctt acatgcctat gcattcgg                                  28

<210> SEQ ID NO 58
<211> LENGTH: 30
<212> TYPE: DNA
<213> ORGANISM: Artificial sequence
<220> FEATURE:
<223> OTHER INFORMATION: PCR primer

<400> SEQUENCE: 58
ctcttctaga gatcggtaga acagcgtaac                                30

<210> SEQ ID NO 59
<211> LENGTH: 30
<212> TYPE: DNA
<213> ORGANISM: Artificial sequence
<220> FEATURE:
<223> OTHER INFORMATION: PCR primer

<400> SEQUENCE: 59
ctctgagctc gccaagtcat gaaggttgtc                                30

<210> SEQ ID NO 60
<211> LENGTH: 30
<212> TYPE: DNA
<213> ORGANISM: Artificial sequence
<220> FEATURE:
<223> OTHER INFORMATION: PCR primer

<400> SEQUENCE: 60
ctctagtact caacaggagt tggagatgtc                                30
```

<210> SEQ ID NO 61
<211> LENGTH: 31
<212> TYPE: DNA
<213> ORGANISM: Artificial sequence
<220> FEATURE:
<223> OTHER INFORMATION: PCR primer

<400> SEQUENCE: 61
ctctagtact gatgatcctg atgccactat c                                    31

<210> SEQ ID NO 62
<211> LENGTH: 30
<212> TYPE: DNA
<213> ORGANISM: Artificial sequence
<220> FEATURE:
<223> OTHER INFORMATION: PCR primer

<400> SEQUENCE: 62
ctctcctgca ggtccagtgt ggatcgcaac                                      30

<210> SEQ ID NO 63
<211> LENGTH: 33
<212> TYPE: DNA
<213> ORGANISM: Artificial sequence
<220> FEATURE:
<223> OTHER INFORMATION: PCR primer

<400> SEQUENCE: 63
ctctcctgca gggaggatat ggtgactagc ttg                                  33

<210> SEQ ID NO 64
<211> LENGTH: 30
<212> TYPE: DNA
<213> ORGANISM: Artificial sequence
<220> FEATURE:
<223> OTHER INFORMATION: PCR primer

<400> SEQUENCE: 64
ctctgatatc cttcctaaac gatgagcgag                                      30

<210> SEQ ID NO 65
<211> LENGTH: 30
<212> TYPE: DNA
<213> ORGANISM: Artificial sequence
<220> FEATURE:
<223> OTHER INFORMATION: PCR primer

<400> SEQUENCE: 65
ctctgatatc ttggtcagtt cagtctggag                                      30

<210> SEQ ID NO 66
<211> LENGTH: 32
<212> TYPE: DNA
<213> ORGANISM: Artificial sequence
<220> FEATURE:
<223> OTHER INFORMATION: PCR primer

<400> SEQUENCE: 66
ctctcctgca ggtaatggtg tcgaccgaca tc                                   32

<210> SEQ ID NO 67
<211> LENGTH: 32
<212> TYPE: DNA
<213> ORGANISM: Artificial sequence
<220> FEATURE:
<223> OTHER INFORMATION: PCR primer

```
<400> SEQUENCE: 67
ctctcctgca ggaagttaga tgtgctccg ac                                    32

<210> SEQ ID NO 68
<211> LENGTH: 32
<212> TYPE: DNA
<213> ORGANISM: Artificial sequence
<220> FEATURE:
<223> OTHER INFORMATION: PCR primer

<400> SEQUENCE: 68
ctctcctgca ggaattcgca ggatccaagc tc                                   32

<210> SEQ ID NO 69
<211> LENGTH: 32
<212> TYPE: DNA
<213> ORGANISM: Artificial sequence
<220> FEATURE:
<223> OTHER INFORMATION: PCR primer

<400> SEQUENCE: 69
ctctcctgca gggaagcagg ttcttagcga tg                                   32

<210> SEQ ID NO 70
<211> LENGTH: 31
<212> TYPE: DNA
<213> ORGANISM: Artificial sequence
<220> FEATURE:
<223> OTHER INFORMATION: PCR primer

<400> SEQUENCE: 70
ctctgtcgac gatagaagaa gtaggcacct c                                    31

<210> SEQ ID NO 71
<211> LENGTH: 30
<212> TYPE: DNA
<213> ORGANISM: Artificial sequence
<220> FEATURE:
<223> OTHER INFORMATION: PCR primer

<400> SEQUENCE: 71
ctctgtcgac caatctgtat ggttgcctcg                                      30

<210> SEQ ID NO 72
<211> LENGTH: 32
<212> TYPE: DNA
<213> ORGANISM: Artificial sequence
<220> FEATURE:
<223> OTHER INFORMATION: PCR primer

<400> SEQUENCE: 72
ctctcctgca ggctcgaatg tttacctgcc tg                                   32

<210> SEQ ID NO 73
<211> LENGTH: 32
<212> TYPE: DNA
<213> ORGANISM: Artificial sequence
<220> FEATURE:
<223> OTHER INFORMATION: PCR primer

<400> SEQUENCE: 73
ctctcctgca gggatgtat tcgatctggg ac                                    32

<210> SEQ ID NO 74
```

```
<211> LENGTH: 30
<212> TYPE: DNA
<213> ORGANISM: Artificial sequence
<220> FEATURE:
<223> OTHER INFORMATION: PCR primer

<400> SEQUENCE: 74
ctctgtcgac ctcagattgg tttcgcagtc                                        30

<210> SEQ ID NO 75
<211> LENGTH: 40
<212> TYPE: DNA
<213> ORGANISM: Artificial sequence
<220> FEATURE:
<223> OTHER INFORMATION: PCR primer

<400> SEQUENCE: 75
ctgattgcgc accaaaccaa gaacgtatcc aagcaggttc                             40

<210> SEQ ID NO 76
<211> LENGTH: 20
<212> TYPE: DNA
<213> ORGANISM: Artificial sequence
<220> FEATURE:
<223> OTHER INFORMATION: PCR primer

<400> SEQUENCE: 76
ttggtttggt gcgcaatcag                                                   20

<210> SEQ ID NO 77
<211> LENGTH: 29
<212> TYPE: DNA
<213> ORGANISM: Artificial sequence
<220> FEATURE:
<223> OTHER INFORMATION: PCR primer

<400> SEQUENCE: 77
ctctgtcgac tcaacggtag gaagctcag                                         29

<210> SEQ ID NO 78
<211> LENGTH: 30
<212> TYPE: DNA
<213> ORGANISM: Artificial sequence
<220> FEATURE:
<223> OTHER INFORMATION: PCR primer

<400> SEQUENCE: 78
ctctgtcgac gttcttcgaa gtggtggaac                                        30

<210> SEQ ID NO 79
<211> LENGTH: 39
<212> TYPE: DNA
<213> ORGANISM: Artificial sequence
<220> FEATURE:
<223> OTHER INFORMATION: PCR primer

<400> SEQUENCE: 79
gtgaggcagc tgacatcaaa cgttgaagcc aaggtagag                              39

<210> SEQ ID NO 80
<211> LENGTH: 20
<212> TYPE: DNA
<213> ORGANISM: Artificial sequence
<220> FEATURE:
<223> OTHER INFORMATION: PCR primer

<400> SEQUENCE: 80
```

```
tttgatgtca gctgcctcac                                              20

<210> SEQ ID NO 81
<211> LENGTH: 30
<212> TYPE: DNA
<213> ORGANISM: Artificial sequence
<220> FEATURE:
<223> OTHER INFORMATION: PCR primer

<400> SEQUENCE: 81
ctctgtcgac tgatcacctt aaagggcgac                                   30

<210> SEQ ID NO 82
<211> LENGTH: 30
<212> TYPE: DNA
<213> ORGANISM: Artificial sequence
<220> FEATURE:
<223> OTHER INFORMATION: PCR primer

<400> SEQUENCE: 82
ctcttctaga gaaacgatca agtgcaccag                                   30

<210> SEQ ID NO 83
<211> LENGTH: 40
<212> TYPE: DNA
<213> ORGANISM: Artificial sequence
<220> FEATURE:
<223> OTHER INFORMATION: PCR primer

<400> SEQUENCE: 83
gacacgagcg tttatacctc taattgccac tggtacgtgg                        40

<210> SEQ ID NO 84
<211> LENGTH: 20
<212> TYPE: DNA
<213> ORGANISM: Artificial sequence
<220> FEATURE:
<223> OTHER INFORMATION: PCR primer

<400> SEQUENCE: 84
gaggtataaa cgctcgtgtc                                              20

<210> SEQ ID NO 85
<211> LENGTH: 30
<212> TYPE: DNA
<213> ORGANISM: Artificial sequence
<220> FEATURE:
<223> OTHER INFORMATION: PCR primer

<400> SEQUENCE: 85
ctctgagctc gagaacacga accatacgag                                   30

<210> SEQ ID NO 86
<211> LENGTH: 29
<212> TYPE: DNA
<213> ORGANISM: Artificial sequence
<220> FEATURE:
<223> OTHER INFORMATION: PCR primer

<400> SEQUENCE: 86
ctcttctaga tacgtcctaa acacccgac                                    29

<210> SEQ ID NO 87
<211> LENGTH: 40
<212> TYPE: DNA
```

<213> ORGANISM: Artificial sequence
<220> FEATURE:
<223> OTHER INFORMATION: PCR primer

<400> SEQUENCE: 87
gaccaaccat tgctgacttg cgtatccata gtcaggcttc    40

<210> SEQ ID NO 88
<211> LENGTH: 20
<212> TYPE: DNA
<213> ORGANISM: Artificial sequence
<220> FEATURE:
<223> OTHER INFORMATION: PCR primer

<400> SEQUENCE: 88
caagtcagca atggttggtc    20

<210> SEQ ID NO 89
<211> LENGTH: 30
<212> TYPE: DNA
<213> ORGANISM: Artificial sequence
<220> FEATURE:
<223> OTHER INFORMATION: PCR primer

<400> SEQUENCE: 89
ctcttctaga tgatcagtac caagggtgag    30

<210> SEQ ID NO 90
<211> LENGTH: 33
<212> TYPE: DNA
<213> ORGANISM: Artificial sequence
<220> FEATURE:
<223> OTHER INFORMATION: PCR primer

<400> SEQUENCE: 90
ctctcctgca gggtcattga cctggatacg atc    33

<210> SEQ ID NO 91
<211> LENGTH: 41
<212> TYPE: DNA
<213> ORGANISM: Artificial sequence
<220> FEATURE:
<223> OTHER INFORMATION: PCR primer

<400> SEQUENCE: 91
gaacacacca accttgaagt gcatgtcgtt gtcgatgtct c    41

<210> SEQ ID NO 92
<211> LENGTH: 21
<212> TYPE: DNA
<213> ORGANISM: Artificial sequence
<220> FEATURE:
<223> OTHER INFORMATION: PCR primer

<400> SEQUENCE: 92
cacttcaagg ttggtgtgtt c    21

<210> SEQ ID NO 93
<211> LENGTH: 31
<212> TYPE: DNA
<213> ORGANISM: Artificial sequence
<220> FEATURE:
<223> OTHER INFORMATION: PCR primer

<400> SEQUENCE: 93
ctctcctgca gggtcatatt tccgctggca c    31

<210> SEQ ID NO 94
<211> LENGTH: 32
<212> TYPE: DNA
<213> ORGANISM: Artificial sequence
<220> FEATURE:
<223> OTHER INFORMATION: PCR primer

<400> SEQUENCE: 94
ctctagtact atgcgttctt caattgcgac tg                                32

<210> SEQ ID NO 95
<211> LENGTH: 30
<212> TYPE: DNA
<213> ORGANISM: Artificial sequence
<220> FEATURE:
<223> OTHER INFORMATION: PCR primer

<400> SEQUENCE: 95
ctctagtact tgaccaatga gaccaagcag                                   30

<210> SEQ ID NO 96
<211> LENGTH: 29
<212> TYPE: DNA
<213> ORGANISM: Artificial sequence
<220> FEATURE:
<223> OTHER INFORMATION: PCR primer

<400> SEQUENCE: 96
ctctctcata tgcgcacgtc gatcgccac                                    29

<210> SEQ ID NO 97
<211> LENGTH: 32
<212> TYPE: DNA
<213> ORGANISM: Artificial sequence
<220> FEATURE:
<223> OTHER INFORMATION: PCR primer

<400> SEQUENCE: 97
ctctctcata tgcgttgagc agcagaatcc tg                                32

<210> SEQ ID NO 98
<211> LENGTH: 32
<212> TYPE: DNA
<213> ORGANISM: Artificial sequence
<220> FEATURE:
<223> OTHER INFORMATION: PCR primer

<400> SEQUENCE: 98
ctctctcata tgaccgctta tcaggaggca ac                                32

<210> SEQ ID NO 99
<211> LENGTH: 32
<212> TYPE: DNA
<213> ORGANISM: Artificial sequence
<220> FEATURE:
<223> OTHER INFORMATION: PCR primer

<400> SEQUENCE: 99
ctctctcata tgatcaacgt cttaccgcat gg                                32

<210> SEQ ID NO 100
<211> LENGTH: 28
<212> TYPE: DNA
<213> ORGANISM: Artificial sequence
<220> FEATURE:

<223> OTHER INFORMATION: PCR primer

<400> SEQUENCE: 100
ctctctcata tgacgaaact ccccttcc                                      28

<210> SEQ ID NO 101
<211> LENGTH: 31
<212> TYPE: DNA
<213> ORGANISM: Artificial sequence
<220> FEATURE:
<223> OTHER INFORMATION: PCR primer

<400> SEQUENCE: 101
ctctctcata tgcttcgtca tcacgcagga c                                  31

<210> SEQ ID NO 102
<211> LENGTH: 30
<212> TYPE: DNA
<213> ORGANISM: Artificial sequence
<220> FEATURE:
<223> OTHER INFORMATION: PCR primer

<400> SEQUENCE: 102
ctctctcata tgcgtctgat gcctgcgctg                                    30

<210> SEQ ID NO 103
<211> LENGTH: 32
<212> TYPE: DNA
<213> ORGANISM: Artificial sequence
<220> FEATURE:
<223> OTHER INFORMATION: PCR primer

<400> SEQUENCE: 103
ctctctcata tgggaagcct taccgccgaa cc                                 32

<210> SEQ ID NO 104
<211> LENGTH: 29
<212> TYPE: DNA
<213> ORGANISM: Artificial sequence
<220> FEATURE:
<223> OTHER INFORMATION: PCR primer

<400> SEQUENCE: 104
ctctctcata tgaaactctc ggtctgcac                                     29

<210> SEQ ID NO 105
<211> LENGTH: 33
<212> TYPE: DNA
<213> ORGANISM: Artificial sequence
<220> FEATURE:
<223> OTHER INFORMATION: PCR primer

<400> SEQUENCE: 105
ctctctcata tgggatcaaa tacatgaggg tcc                                33

<210> SEQ ID NO 106
<211> LENGTH: 40
<212> TYPE: DNA
<213> ORGANISM: Artificial sequence
<220> FEATURE:
<223> OTHER INFORMATION: PCR primer

<400> SEQUENCE: 106
ctctcatatg aaattaactt ctttacgcgt atctttattg                         40

```
<210> SEQ ID NO 107
<211> LENGTH: 38
<212> TYPE: DNA
<213> ORGANISM: Artificial sequence
<220> FEATURE:
<223> OTHER INFORMATION: PCR primer

<400> SEQUENCE: 107
ctctcatatg ttatctcatt ttcactgcag aacttaac                               38

<210> SEQ ID NO 108
<211> LENGTH: 42
<212> TYPE: DNA
<213> ORGANISM: Artificial sequence
<220> FEATURE:
<223> OTHER INFORMATION: PCR primer

<400> SEQUENCE: 108
ggaattccat atgaatcttt cagtatgcac tatcactttt ag                          42

<210> SEQ ID NO 109
<211> LENGTH: 35
<212> TYPE: DNA
<213> ORGANISM: Artificial sequence
<220> FEATURE:
<223> OTHER INFORMATION: PCR primer

<400> SEQUENCE: 109
ggaattccat atgttaaatg gcttgagcgg tagtc                                  35

<210> SEQ ID NO 110
<211> LENGTH: 30
<212> TYPE: DNA
<213> ORGANISM: Artificial sequence
<220> FEATURE:
<223> OTHER INFORMATION: PCR primer

<400> SEQUENCE: 110
ggaattccat atgattcgct tccacctgtg                                        30

<210> SEQ ID NO 111
<211> LENGTH: 33
<212> TYPE: DNA
<213> ORGANISM: Artificial sequence
<220> FEATURE:
<223> OTHER INFORMATION: PCR primer

<400> SEQUENCE: 111
ggaattccat atggatgagg ttcactggca gac                                    33

<210> SEQ ID NO 112
<211> LENGTH: 30
<212> TYPE: DNA
<213> ORGANISM: Artificial sequence
<220> FEATURE:
<223> OTHER INFORMATION: PCR primer

<400> SEQUENCE: 112
ggaattccat atgagaatcg cgctctgcac                                        30

<210> SEQ ID NO 113
<211> LENGTH: 33
<212> TYPE: DNA
<213> ORGANISM: Artificial sequence
<220> FEATURE:
<223> OTHER INFORMATION: PCR primer
```

<400> SEQUENCE: 113
ggaattccat atggtcatgt cggtctcctg aag          33

<210> SEQ ID NO 114
<211> LENGTH: 33
<212> TYPE: DNA
<213> ORGANISM: Artificial sequence
<220> FEATURE:
<223> OTHER INFORMATION: PCR primer

<400> SEQUENCE: 114
ggaattccat atgccgtcaa agctagccat tag          33

<210> SEQ ID NO 115
<211> LENGTH: 35
<212> TYPE: DNA
<213> ORGANISM: Artificial sequence
<220> FEATURE:
<223> OTHER INFORMATION: PCR primer

<400> SEQUENCE: 115
ggaattccat atgttacaat gaagcagaga ctcgg        35

<210> SEQ ID NO 116
<211> LENGTH: 31
<212> TYPE: DNA
<213> ORGANISM: Artificial sequence
<220> FEATURE:
<223> OTHER INFORMATION: PCR primer

<400> SEQUENCE: 116
ggaattccat atgcccaacc gtctcggcat c            31

<210> SEQ ID NO 117
<211> LENGTH: 34
<212> TYPE: DNA
<213> ORGANISM: Artificial sequence
<220> FEATURE:
<223> OTHER INFORMATION: PCR primer

<400> SEQUENCE: 117
ggaattccat atgctacaac cgatgctgca caac         34

<210> SEQ ID NO 118
<211> LENGTH: 31
<212> TYPE: DNA
<213> ORGANISM: Artificial sequence
<220> FEATURE:
<223> OTHER INFORMATION: PCR primer

<400> SEQUENCE: 118
ggaattccat atgagtgccg agaggcgact g            31

<210> SEQ ID NO 119
<211> LENGTH: 32
<212> TYPE: DNA
<213> ORGANISM: Artificial sequence
<220> FEATURE:
<223> OTHER INFORMATION: PCR primer

<400> SEQUENCE: 119
ggaattccat atggtgctgc tgatcagcct gc           32

<210> SEQ ID NO 120
<211> LENGTH: 30

<212> TYPE: DNA
<213> ORGANISM: Artificial sequence
<220> FEATURE:
<223> OTHER INFORMATION: PCR primer

<400> SEQUENCE: 120
ggaattccat atgcgtacct cgatcgccac                                      30

<210> SEQ ID NO 121
<211> LENGTH: 33
<212> TYPE: DNA
<213> ORGANISM: Artificial sequence
<220> FEATURE:
<223> OTHER INFORMATION: PCR primer

<400> SEQUENCE: 121
ggaattccat atgcagaatc cgttctgcca tgg                                  33

<210> SEQ ID NO 122
<211> LENGTH: 30
<212> TYPE: DNA
<213> ORGANISM: Artificial sequence
<220> FEATURE:
<223> OTHER INFORMATION: PCR primer

<400> SEQUENCE: 122
ggaattccat atgggacgac aggttcgtac                                      30

<210> SEQ ID NO 123
<211> LENGTH: 32
<212> TYPE: DNA
<213> ORGANISM: Artificial sequence
<220> FEATURE:
<223> OTHER INFORMATION: PCR primer

<400> SEQUENCE: 123
ggaattccat atgcttcgaa tcgaccgctc ag                                   32

<210> SEQ ID NO 124
<211> LENGTH: 32
<212> TYPE: DNA
<213> ORGANISM: Artificial sequence
<220> FEATURE:
<223> OTHER INFORMATION: PCR primer

<400> SEQUENCE: 124
ggaattccat atgcctaacc gtctcggaat tg                                   32

<210> SEQ ID NO 125
<211> LENGTH: 33
<212> TYPE: DNA
<213> ORGANISM: Artificial sequence
<220> FEATURE:
<223> OTHER INFORMATION: PCR primer

<400> SEQUENCE: 125
ggaattccat atgctaaagg cgatgctgca cag                                  33

<210> SEQ ID NO 126
<211> LENGTH: 43
<212> TYPE: DNA
<213> ORGANISM: Artificial sequence
<220> FEATURE:
<223> OTHER INFORMATION: PCR primer

<400> SEQUENCE: 126

```
ctcttcatga aatattcgct atgtaccatt tcatttcgtc atc          43
```

<210> SEQ ID NO 127
<211> LENGTH: 39
<212> TYPE: DNA
<213> ORGANISM: Artificial sequence
<220> FEATURE:
<223> OTHER INFORMATION: PCR primer

<400> SEQUENCE: 127

```
ctcttcatga ctctaaacga gactctcaca tcatttcac              39
```

<210> SEQ ID NO 128
<211> LENGTH: 507
<212> TYPE: DNA
<213> ORGANISM: Providencia stuartii

<400> SEQUENCE: 128

```
atggatgaaa cgctttttat ctctcacccg ataacatggc tatcagaaga tgatgacctt    60
gttcctgaaa atgttttaga ttggctacat gaactagggt cgatgacaaa acgcttagag   120
cagcattgcc aacgtgtcac ggttgttcct tatacgcaac gttatgtgac tcaagaggca   180
ttgagcgaag aagaagcggc gtgtttacct gtcagtgaat attattggtt acgtgaagtc   240
attatgtatg gtgataatat tccatggtta cttggacgaa cgttaattcc acaggagaca   300
ttgactggtg aagaccggaa acttattgat atcggtgctg taccgttagg cgttatctc    360
tttagccatg ataatctttc ccgtgattat attcatatag ggcagcaaaa tttgcgatgg   420
atccgccgct ctctattaag attatctgaa aaacctttat tattaaccga actgttttta   480
cctgaatcac ctgcatataa aagataa                                        507
```

<210> SEQ ID NO 129
<211> LENGTH: 510
<212> TYPE: DNA
<213> ORGANISM: Cronobacter sakazakii

<400> SEQUENCE: 129

```
atgtcccatc ccgcgctgag acaactgcgc gcgttgtcct ttttgacga tatcagcacg    60
cttgatagtt cgctgctcga ctggctgatg ctggaagatt ccatgacccg ccgtttcgaa   120
ggcttttgcg agcgcgtgac ggtcgacatg ctgtttgagg gctttgtcgg ccccgaggcg   180
ctggaggaag agggcgagtt tttgcctgat gagccgcgct actggctgcg cgaaatcctg   240
ctgtgcggcg acggcgtgcc gtggctggtt gggcgcacgc tggtgccgga gtctacactt   300
tgtgggccgg agctggcgtt gcagcagctc ggtaccacgc cgctgggccg ttatctgttt   360
acctcatcca ccctcacgcg tgattttatc cagcccgggcc gcagcgacga actctgggga   420
cgccgctctc tgctgaggct ttccggcaaa ccgctgctgc tgactgaact gttttttacct   480
gcatcaccct tgtacggaga ggaaaaataa                                     510
```

<210> SEQ ID NO 130
<211> LENGTH: 30
<212> TYPE: DNA
<213> ORGANISM: Artificial sequence
<220> FEATURE:
<223> OTHER INFORMATION: PCR primer

<400> SEQUENCE: 130

```
ctctgtcgac cagacaacca ggttgatctc                        30
```

```
<210> SEQ ID NO 131
<211> LENGTH: 40
<212> TYPE: DNA
<213> ORGANISM: Artificial sequence
<220> FEATURE:
<223> OTHER INFORMATION: PCR primer

<400> SEQUENCE: 131
gatgcctagg gattcttcca tttggaatgc tcgatgggtg                  40

<210> SEQ ID NO 132
<211> LENGTH: 20
<212> TYPE: DNA
<213> ORGANISM: Artificial sequence
<220> FEATURE:
<223> OTHER INFORMATION: PCR primer

<400> SEQUENCE: 132
tggaagaatc cctaggcatc                                        20

<210> SEQ ID NO 133
<211> LENGTH: 32
<212> TYPE: DNA
<213> ORGANISM: Artificial sequence
<220> FEATURE:
<223> OTHER INFORMATION: PCR primer

<400> SEQUENCE: 133
ctctgagctc gttactcgtt aaggaagcac tc                          32

<210> SEQ ID NO 134
<211> LENGTH: 1863
<212> TYPE: DNA
<213> ORGANISM: Corynebacterium casei

<400> SEQUENCE: 134
atgcgttctt caattgcgac tgtttgtcta tcgggcactc tcgcggaaaa gctgcgggct    60
gctgccgatg ccggctttga cggagtagaa atctttgaac aagacttgat tgtctcgccg   120
cattcaccag aacaaattcg tgaacgtgct gcggaattgg gtctcacact ggacttgttc   180
cagccgttcc gtgacttgct gagcgtggaa gaagatatct ccgggataaa tctgcgccgt   240
ctggaatcca agttccagct catgcagcgt cttggcatgg accagatttt ggtgtgctct   300
aacgtggcta ctgccactgt ggatgatgat gaagtccgcg tggatcagct cgccgcgcc    360 ggtgagttgg ctgcacgcta tggctgcttc atctcttatg aggcattggc ttggggcaag   420
tatgttaata cttatcagca tgcttatgac cttgtggtta aggctgatca tccgaatgtg   480
ggcacgtgtt tggattcttt ccatattctt tcccgcggtg atgatccatc ggggattgcg   540
gatatggatc cggataaaat tttcttcttg cagctcgcgg acgctccgac tatggagatg   600
ggaatcttac cgtggtcacg ccaccaccgc gtattccgg gcgagggtga tttcgacctg   660
aagaacttca tggagcaggt agccaaatca ggttataacg tccagtgtc gttggagatt   720 ttcaatgatg aattccgcga ggctgaggtc ggccggaccg cgatcgatgg tctacgctcg   780
ctgatttggt tggcggacaa aactgcaaca cgggtgccgg actcaccgtt ggaattaccg   840
aagctggcta tgctcagtc accacggggc tttgactttg tggaactacg cacggggcgc   900
ctgggcgaag tcaccaaggc actgcaccaa ctgggattcc gtttgggtgg ctaccaccag   960
tccaaaccag actttcaagc gtgggtgcag gggatgttc gcatcatcgt ggaggatgaa  1020
ggttccaccg gtgcgcaac ggagctgaca ggcttgggtg tcatcgtgga tgatgccact  1080
```

| | |
|---|---|
| gctgcggcag agcgtgccac cgcgttgaaa gcaacaccag ttccacgcat gaccggggaa | 1140 |
| gatgaagaag acctacatcc agtctttacc ccagatggat ctgaactgta cttttgtgga | 1200 |
| ccaggacaaa ctggccgggg aagcacatgg ataccggagt tcggttttga acccgatgaa | 1260 |
| accagtagct cggagacttc tgacgtattg attaattctg ttcaccacat tgctttggcg | 1320 |
| cagccacggc atatggctgc ggaaacccgt ttatttact cttcggttct gggattggaa | 1380 |
| ccagctgtgc cggagttcat tccgtcgcca gcaggtctgg tgcacaagca ggcgattgaa | 1440 |
| ggcgagaatg tttgcatcac agtgtcggcc gctccggaag gctctgaaca gggtggtttc | 1500 |
| tttgctgagc actacccgga acacatcgct tttggcagtg atgacgtctt tgcagttgca | 1560 |
| caacgcgcgg tgaggcgtgg attgaagatg ttgcccattc cagagaatta ctatgatgac | 1620 |
| ctggcagcac gcttcggact ggaaccggga ttcatcacga agattaaagc actcaatatt | 1680 |
| tgctatgacc gcagcagcaa tggcgaatat ctgcactttt acaccgcgcc tttgggcaat | 1740 |
| accttctttg aggtagctga ggttcgaggg gactaccgcg gtttcggctg ggcagatgaa | 1800 |
| ccgattcgct tggccgcgca ataccgcgcg ctgcgcgatg atgtccgcgg aatcccgcgc | 1860 |
| taa | 1863 |

<210> SEQ ID NO 135
<211> LENGTH: 1869
<212> TYPE: DNA
<213> ORGANISM: Corynebacterium efficiens

<400> SEQUENCE: 135

| | |
|---|---|
| atgcgcacgt cgatcgccac cgtctgttta tcaggaaccc tcgccgagaa actccgcgcc | 60 |
| gccgccgacg ccggctttga cggcgtggaa atcttcgaac aggacctcac cgtctccccc | 120 |
| cactccccgg agcagatccg gcagcgggcc gccgacctgg ggctgaccct ggatctcttc | 180 |
| cagcccttcc gggatttcga gggggtggag gaggaacagt tcgtgaagaa tctccgccgc | 240 |
| atggaggcga agttcgcact gatgaaccgg ttggggatcg acaccatcct gctgtgctcc | 300 |
| aatgtcgcca ccgcgaccat caacgatgat gaactcttcg ccagccagct gcgccgcgcc | 360 |
| ggggacctgg cacagcgcta ccaggtccgc atcgcttatg aggcgctggc gtgggggcgg | 420 |
| tcgtcaacg atttcgagca tgcccagcgc atcgtcgaca tggccgacca cccccaggtg | 480 |
| ggcacctgcc tggataccct tccacatcctc tcccgcgggt ggtccaccga cgcggtggag | 540 |
| cagatccccg gcgagaagat cttcttcgtc cagcttgccg atgcccccaa gctcagcatg | 600 |
| gacatcctgt cctggtcccg ccaccaccgg gtcttcccg gggagggcga tttcgacctg | 660 |
| gtgaaattca tgacccacct cgcccgcacc ggatacgacg acccatctc cctggagatc | 720 |
| ttcaatgatt ccttccgcaa ggccgatgtg cccgcacgg ccgtcgatgg tctgcggtcc | 780 |
| ctgcgctggt tggaggacca gacgtggcac gccctggccg aggacgaacg cgatgtgacc | 840 |
| ctgcagctgt ccccgctgcc ggaggtcgca gaacccgccg gtgtggattt cctcgagatc | 900 |
| tccaccggac ggctggggga gaccatccgg gtgctccacc agctgggttt ccagctcggt | 960 |
| ggccaccacc gcagcaaatc cgacttccag gtctggaccc aggggccggt ccgcatcgtc | 1020 |
| atcggtgacc gcgggcccac cggcgccgcc accaccatca ccgggctcgg tttcgccacc | 1080 |
| ccggatccgg cctccgcgca gcagcgcgcc catctcctcc aggcgggcac catcgcccgg | 1140 |
| acccgcgagg acgatgaggc agatctgcgg ggcgcctacg ccccgacgg caccgaggtg | 1200 |
| ttcttcggtg aggtcagccc ggacggattc cccacctggc tcgatgagtt cggtgtggag | 1260 |
| aagaccgacc aggtgtccga cagcctcatc accgggatcg accacatcaa cctcgctcag | 1320 |

```
ccctggcagc acttcgacga gtccatcctc ttctacacct ccctcatggc gctggaggcc      1380
cgcgaccgcg atgagttccc cagccccatc ggtctgatca gcaaccaggt gatgagctca      1440
cccaatgacg ccgtgcgtct gctgctcagc atcgccccgg aggacgggga acagggtgat      1500
ttcctggacg ccgcctaccc cgagcacatc gcgctcacca ccaccgatat cgtcgcggtg      1560
gcccgccgtg cacgcaagcg tggcctggcg ttcctccccg tcccggagaa ctacttcgag      1620
gacctgcagg cacgtttcga tctcgacccg gagttcctgg atctgctacg cgagaacaac      1680
ctgctctatg accgtgatga ccacggtggg gaattcctcc acttctacac ccgcaccctg      1740
ggcaccatgt tcatcgaggt cgtggaacgc cgcggtggtt tcaccggctg ggtgagacc      1800 aacgcaccgg ttcggctcgc cgcccagtac cgcacgatcc gcgacgccga gcgcggggtc      1860
ccgcgctaa                                                              1869

<210> SEQ ID NO 136
<211> LENGTH: 1917
<212> TYPE: DNA
<213> ORGANISM: Pantoea ananatis

<400> SEQUENCE: 136
atgaccgctt atcaggaggc aacaatgaaa cgttctgtcg ctacggtctc ggtatcgggc       60
acgctgccgg aaaaactgcg agcaattgcc gccgcaggct tcgatggcgt tgaaattttc      120
gataacgatc tggtctatta tcccggctca cccgtggaaa tccgccagct gtgtgaagcc      180
ctcgggctgg aaatcttgct gtttcaacct tttcgcgact tcgaaggcgg tccccgtgac      240
aggctggcgc aaaacctggc gcgcgcggcg cgcaagtttg aggtcatgca acagctgggc      300
tgtcagcgga tgctggtctg cagcaatgtc tcacccgact gcagtgacga cttcgccaca      360
caggtcagcg atctcaccgc tctggcagag ctggcggctg agcacggtat tactctcggt      420
tatgaggcgc tggcctgggg acgacacgtc agcctgtggc gcgacgcctg ggcccgcgtc      480
aaggccgtca accatcccgc gctggggatc gtgctcgaca gttttcatat tctgtcgcgc      540
ggcgacagcc tggacgggct ggaagcagtc ccgacggaga aaattgtgtt cgtacagctg      600
gcggatgcac cgctgctaaa aatggatgtg ctgtcgtgga gtcgccactt ccgctgtttt      660
cccggccagg gcgaattcaa tctgactcag tttatgacgc aactgtcggc gcatggctac      720
cgggatgcct ggtcgctgga aatttttcaac gatggattcc gcgcctcgcc ggtggtgcct      780
accgcgcagg atggttatcg atcgctgctg tggctggagg agcaaacccg tgactggctg      840
gtcggacagc cgctgctgcc gagcgcgctg gcctccctgg ccggggaagg gctgttccac      900
tctgcgcccc agccgccgct gttgtcgctg gagttcattg agtttgccgt cagccacaat      960
gacgctttgg cactcggaca gtggctgacg cagcttggcc tggttcatgc gggcgatcat     1020
cgctccaagc aggtgtcgct gtatcgtaac ggcaaggtgc atgtgattct gaatgcgcag     1080
ccggagagcc aggccagcgg gtattatcat cagcacggta tttcgctgtg tgcggtggcc     1140
tggcgggttc gcgggtcga taagctgatc acgcgcgcgc aggattacgg ttacgccatc     1200
tggcagggga aaaccggccc caacgaacgc cagatcccgg cgttatgtgc gcctgacggc     1260
agcctgattt atctggtgga agatgagcct gccggtcaag acggctacca cagcgacttc     1320
cacttaacgc accgccgcc gccccagcct gcgatgcaga ccatcgacca tctggcgatt     1380
gccctgccgg atgatacgcg cgataactgg attatgttcc tgcgtagcgt gccgggtttt     1440
gtgcaggata ccgagtggga actgcccgat ccgctggggc tggtgcgtag ccgcgtgctg     1500
```

| | |
|---|---:|
| cgaagcccca acgatgcgat tcgcctgccg ctaaacatgt cggtcagtcg ggaaacccag | 1560 |
| atagcccgcg ctttaacgac ctatcagggc gcaggtttgc agcacgtcgc ctttggctgt | 1620 |
| gacgatctgt tcagtgcggt aaaggccgcg cgcgaacgtg ggctgaaaac cttgcacatt | 1680 |
| cccgataact attatcagga cctgatggcg cgtttcgatc tcgacgccga ttttctggcg | 1740 |
| cagctgcagc gttacgatgt gctgtacgat cgggacgaac agggcgggga gctgctgcac | 1800 |
| gtctatacgc ttccctatga aaagggccgc ttcttctttg agctgctgga cgacgtggc | 1860 |
| ggctatcgtg gctttggcgc ggccaatgct cccgtgcggc tgaccgccat gcggtaa | 1917 |

<210> SEQ ID NO 137
<211> LENGTH: 852
<212> TYPE: DNA
<213> ORGANISM: Gluconobacter oxydans

<400> SEQUENCE: 137

| | |
|---|---:|
| atgacgaaac tcccctttccc tttcggcatg aacgaattca cgacccagcc ctggtcgttc | 60 |
| gaggaagacg tggcgcgtta ccgcgacctc ggcgtggatg cgatcgagat ctgtgaagcc | 120 |
| aagcttgatc cggcccgcat tgaggagcag atgtgcctcg tcaggagag cgggctgagc | 180 |
| gtcagtgcgg tccagccgct ggtccggacc ttcttcggaa cgctatggt ccctgaacct | 240 |
| gaagcgactg aagcccgcgt caaacgcctt acccaaagcc tgaaaacgct cgcgcctcat | 300 |
| gtccccggca cgtctttgt gaccaatacc ggcgcgccac ccaagggtaa catgcgccgt | 360 |
| accatggacg agacggtgcg ttacctgaag gagctctgtc cccttgccga ggatctgggt | 420 |
| gtttccctgt cgctggagcc gctcaacccg acctcggtga acaccgaaag cgccatctgg | 480 |
| accatcgagc aggccatgga catcattgag gacgtcggcc atccggcgat gggtctgtgt | 540 |
| ctggattact ggaacatctg gcagcagaag gatgtctgcg cggctatccg tgctgcggga | 600 |
| agcaaaatca acgtccttca ggtcagcgac tggcgcacgc cctattccgc cgccgaccgc | 660 |
| ctgatccccg gcgatggctg cattccgctt catgaaatgc tgcatgccac atgggatgcg | 720 |
| ggctttcgtg gcgcctgcac ggtcgagatc ttttcgtcag atgtgccgga cagccttat | 780 |
| gaccgcgacc tgagcgatgt catccgcttc tgccgcgagg gactggatca ggcctggacc | 840 |
| ggcgaggcct ga | 852 |

<210> SEQ ID NO 138
<211> LENGTH: 1473
<212> TYPE: DNA
<213> ORGANISM: Pseudomonas putida

<400> SEQUENCE: 138

| | |
|---|---:|
| atgcgtctga tgcctgcgct ggtggccttg ctgccactgc tcccctgcc cgccctggcc | 60 |
| gccgcaccgg ccaaccccga aaccctgcgt gtcgagcgct acgctgacga cgaccagctc | 120 |
| ggctcgctgc gctgggccat cgaaaccagt aaccagaacc ccggccacta cagcatcgac | 180 |
| attgccgccg tcgccagcc gccctacgtg atccgcccca gcgtgcgct gccggaaatc | 240 |
| aagggcccgg tgcgcatcac cggcctgcct tgggcccgcg atggccaata catcgccatc | 300 |
| gacggttcgg cctacatcaa ggaccagggc gtacgtacct gccccggcgc cctgcccggc | 360 |
| cagttcggca ctaacgtgcg caccaccacc aaccccgggc tggtgctgcg cgacacccag | 420 |
| ggcgtgcacc tgagcggcct ggaagtgcgc aacttctgca tcggcatcct ggtcaaccgc | 480 |
| gccagcggca acgtgatcga agacaaccgc atcgtcgcca caaaggtgg cgcgggcatc | 540 |
| atgctgaccg gtgacgacgg cgcgggtaac cccaccgcca ccaccacgaa caacaacaag | 600 |

```
gtgctgcgca accaactgat cgacaatggc gacggcctgg agctgacccg cggagcggca      660
ttcaacctgg tggccgacaa tctgttccgc tccacggcgg ccaacccccga accctcgcag     720 ggtatcgaga ttctgctggg caacgacaac agcgtggtgc gcaaccgctt cgagaactac      780
tccgacggcc tgcagatcaa ctggggcaag cgcaactacc tggcggccaa cacccttcagc    840 ggcaactcga tcggcgtcag cgtcaccggc gagggcaaca tcctcgacgg caacctgatc      900
cacggcaacc gcatcggcgt tgcactgcgc ccggaaccgg atgctaccgc cacgcgcctg      960
agcggcaacc gcatctgggg taacagccag gatatccgcc gctgtgaagc gggcggttcg     1020
tgcgtgccgg ccaacgcac cggcgccatc gtgtttggcg tgcctgcgca ggcgcatgcg      1080
ctgtatgtag ttcgcgcgg ggtgggcgcc gacttgccga agaaagacca ggcgatcatc      1140
tgcgatgcca acggcgagcc caagccttgc cagccgctgc ccaaccataa ccagcaggcg      1200
ccaaggctga ttgcgctgga aggcaatgtg ttgcgcggtg aagtacaggg gccggaatcg      1260
agcctgctgc gggtggagtt ctttggcaat gccgaggcga atggcaccga ggcggagcag      1320
tacctcgggg aggtgctggt gaacagtgac agacagggc aagcgcggtt tgcacaagtg      1380
ctggagaaca tcggtgggtt gcgcagcttt accgcgaccg taaccactgc cgatggggca      1440
acctccgagt tgagcctgcc ggttcggcgg taa                                  1473

<210> SEQ ID NO 139
<211> LENGTH: 918
<212> TYPE: DNA
<213> ORGANISM: Rhodopseudomonas palustris

<400> SEQUENCE: 139
atgaaactct cggtctgcac catcacattc cgccatcacc tgctctgctt cagcgagatc       60
gtcgagtgga cgcaacgcaa cggcttcgac ggcgtcgaac tgtggggcgc tcatgcgcgc     120
ggcctgatgc ggacgcaccc ggaatacgat gcagattggc ttcgcagtta cggcctgtcg     180
gtgccgatgc tgagcgatta cctgccgacc gatggcgaca tcacggacac tcgccaccgt     240
gcaatcgagc tctgccggat tgcacagcat tggtcagcgc gaaagatccg cacattcgcc     300
ggtaacagac cgagcgccca gctgtcgcgc gagcagcgca gagcgctggc cggccggatc     360
ggtgagatcg ccggcatcgt ccatgatcac ggcatccggc tgttggtcga gacacacccg     420
aacacgctgg ccgacaacgt cgactcgaca cttggcctgt tggcggatgc caaccacccca    480 ggtctcggta ttaacttcga tgctctgcac gtctgggaag gcggcgacga tcccgttctg     540
gctcgccgca cgctcgcgga cttcatcggg cactatcatc tcaagaacgt ccgatcacgc     600
gacgagctcg gtgtgttcgc ccctgagaac gtctattctg ccgccggctc ccgtgacggc     660
atggtgccgc tgtttgacgg cgcgatggat tacgaaggtt tcctcgcatc cttggcggac     720
gagaccgatg cggaagcgtc gctcgaatgg ttcggtcacg attgcttcga aaccctggcc     780
cgagatcggc tagccatatt cgcacgctcg atatcgacga gggtcgccg cggctcggcg      840 ggcacgcagc aagcgcggct ggcagagtcg cgtgccgccg ccgcgccgc ctcctccaaa      900 ggaccctcat gtatttga                                                   918

<210> SEQ ID NO 140
<211> LENGTH: 1461
<212> TYPE: DNA
<213> ORGANISM: Acinetobacter baylyi

<400> SEQUENCE: 140
```

```
atgaaattaa cttctttacg cgtatcttta ttggcgctgg gcttggtaac atcaggtttt     60
gctgcggcag aaacttatac tgtagatcgt tatcaggatg atagtgaaaa aggctctttg    120
cgttgggcaa ttgaacaatc taatgcaaat agcgcacaag agaatcagat tctgattcag    180
gctgttggta aggcacctta tgtgatcaag gtggataaac cgttaccacc gattaaatca    240
tctgtaaaaa ttattggtac agaatgggat aaaacgggcg aatttattgc gattgatggt    300
tcaaactata tcaagggcga aggcgaaaaa gcatgtccag gtgcaaatcc aggacaatat    360
ggtaccaatg ttcgtaccat gactttacca ggtttggttc tacaagatgt caatggtgtg    420
accctgaaag tcttgatgt tcatcgcttc tgtattggtg tactggtaaa tcgttcaagc     480
aataatttga ttcagcataa ccgtatttca ataattacg gtggcgctgg tgtcatgatc     540
acgggtgatg atggtaaagg taacccaacg tctaccacca ccaataacaa caaagtattg    600
gataatgtgt ttattgacaa tggcgatggt cttgaactga cgcgtggagc agcattcaac    660
ctgattgcta caatctgtt tacatcgacc aaagccaatc cagagccgtc tcaaggcatt     720
gaaattcttt gggggaatga caatgcagtg gtgggtaaca aatttgaaaa ctattcagat    780
ggtctacaaa tcaactgggg taaacgtaat tacatcgctt ataacgaatt gaccaataac    840
tctttgggtt tcaatcttac aggtgatgga acatcttcg atagtaacaa agtgcatggc     900
aatcgtattg gtatcgcaat tcgttctgaa aaagatgcaa atgcacgtat cacacttacc    960
aaaaatcaga tttgggataa tggtaaagat atcaaacgct gtgaggctgg tggttcatgt   1020
gttccaaacc aacgtttagg tgcaattgta tttggtgttc ctgcgcttga gcatgaaggt   1080
tttgtaggct ctcgtggtgg cggtgtagtc attgaacctg caaaattaca aaaaacatgt   1140
acacagccaa atcaacaaaa ctgtaatgcc attccgaacc aaggtattca ggcacctaaa   1200
ctgactgtca gtaaaaaaca acttacagtt gaagttaaag gaacaccaaa ccagcgttac   1260
aacgtagaat tttttggaaa tcgtaatgca tcttcttccg aagctgagca atatttaggt   1320
tcaattgttg tagtgacaga tcatcaaggt cttgcaaaag caaactgggc accaaaagtc   1380
agcatgccat ctgttactgc gaatgtaact gatcacttgg gcgccacttc agagttaagt   1440
tctgcagtga aaatgagata a                                              1461
```

<210> SEQ ID NO 141
<211> LENGTH: 846
<212> TYPE: DNA
<213> ORGANISM: Alteromonas macleodii

<400> SEQUENCE: 141

```
atgaatcttt cagtatgcac tatcactttt aggcaccaac ttatctcaat cgctgaaatt     60
gcaaaatggt ctgtggcaaa tggttttcag gggatcgaat tatggggtgc acatgctacg    120
aatttagaag accaacccga gtatgggaaa gagtggctct caagctacgc gttgaaaaca    180
tccatgctaa gcgattatct gccacttttt gaagggaacg acgctttgta ttttaaggtt    240
catcgccttt gtcgtttggc taaacactgg ggggcaacca agattcgcac atttgctggc    300
aacgaaggca gcgcagccat acctgaagac cgaaaaaccc tgcttttcga gcggttacaa    360
cttgtttgtg attggcttag cgactatggg cttaacttag ttatcgaaac acaccctaat    420
acttacgctg actcggtggg ttctaccatt gaattgtttg aaaaagttaa caaagacaat    480
ttgcaactaa attacgatgt gttgcatgta tgggaatctg gcgctgacat tatttcctct    540
tgtgaacaac tcgcgccata tataaatcat tttcacttta aaaacataag tagcagtaaa    600
cacttaagtg tgtttgctcc agacaatgtg tatgccgcag caggctcgcg agaaggcatg    660
```

| | |
|---|---:|
| gtccccattt tcgacggtgc tgtagattat caaaggttta ttgaatacct gtactcgaaa | 720 |
| acaactctgc gaaatattga ctcttcactc gagtggtttg ggaacaattg caagaatatc | 780 |
| ctcagtcagg acagatataa attacagaaa atgagccagg ccgcgactac cgctcaagcc | 840 |
| atttaa | 846 |

<210> SEQ ID NO 142
<211> LENGTH: 876
<212> TYPE: DNA
<213> ORGANISM: Marinobacter hydrocarbonoclasticus

<400> SEQUENCE: 142

| | |
|---|---:|
| atgattcgct tccacctgtg caccatctcg ttccgccacc agttggtgtc gttaccggaa | 60 |
| ctcgctacct gggctggcgc caccggcttt gacggtattg aactctgggg cgtgcatgcc | 120 |
| tggcacctgt tacagcagcc cggactggat ggccgctggc tgcaaagcca gggactggcc | 180 |
| attcccatgg tcagcgacta cctgccgcta gacggtagcg agcaggaggc tatccactac | 240 |
| acccgcgaac tctgccggct ggcccgacac tggcaggccc ccaaactgcg aacgtttgcc | 300 |
| ggccatcagg gcagcgccga gctcgaccag agacagcgcc aggcccagac ccgacgtctg | 360 |
| cagacgctga cccgttgcgt cgcagatgaa ggcctgaccc tggtggtgga aacacacccc | 420 |
| ggcaccctgg ccgatacggt cgactccacg ctgacgttgc taaccgacgt ggatcacccg | 480 |
| gccctgggta tcaacttcga cgtcttgcat gtctgggaag ccggagcaga cccaaagctg | 540 |
| gcgctgcaac aaatggcgcc ctgggtcaga cattttcact tcaagaatat ccgtcatcgg | 600 |
| gatcagctcg gcgtatttgc tccggctaat gtctactcac cggccggttc ccggcaggga | 660 |
| atggtgcctg tgctggacgg tgcctgtgac taccggccgc tactggacac cctggccggc | 720 |
| tggcaacagt cgcaaaccca tccggcccca ctggacattt ccctggagtg gttcggcccg | 780 |
| gacagctacc gggtgctatg cagcgatctt caccagttgc ggcaaaacgt tcgccagaac | 840 |
| cacgcgcaat ctcaggcgct ggccgtctgc cagtga | 876 |

<210> SEQ ID NO 143
<211> LENGTH: 837
<212> TYPE: DNA
<213> ORGANISM: Methylobacterium extorquens

<400> SEQUENCE: 143

| | |
|---|---:|
| atgagaatcg cgctctgcac catcagcttt cgccaccatc tcgtgtcgat cggcgaactc | 60 |
| gcccgcttcg cccgcggcca cggcttcgac ggcatcgaat tgtggggcgt gcatgcccgc | 120 |
| aatctcggcc ccggcgacca cgctgaatgg ctcgccgcct acggcctgcg cgtgccgatg | 180 |
| ctgagcgact acctgccgct cgacgcgccg ctggaaatcc tgaccgagcg gacggccgaa | 240 |
| ctcgcccggc tcgccgggag ctgggggggcg ccgcggctgc gcaccttcgc cgggaccaag | 300 |
| ggcagtgcgg ccgcctcgct cgacgagcgc gcccatgtcg cccagcgcct gcggatggcg | 360 |
| gcgggccaac tcgccgacca gggcctgcgc ctcgtggtgg agacgcatcc cggcacgctc | 420 |
| gccgacacca ccgcctcgct cctcgacctg ctgatgcgg tcgatcaccc gaacctccgg | 480 |
| gtcaatttcg acacgctcca cgtctgggaa ggcggcgacg acccgctcgc ggcccacgcc | 540 |
| cggctctccc cgcatatcga ctactatcac ctcaagaacg tgcgcagccg cgccgacctg | 600 |
| tcggtgttcg agcggccaa cgtctatgcc gcggccggac ggcgcgaggg catgaccggc | 660 |
| ctgttcgagg gcgcgctgga ttacgccgct ttcctgaaga cgctgccgcc gcaggcggaa | 720 |

```
ggctcgctcg aatggttcgg cgaggccagc ttctcggtcc tgcccaccga ccttttccgc    780
ctgcgcagtg ccactgccgg ccgccgcggg gcgggagccc tccacgccgc gcgctga      837
```

```
<210> SEQ ID NO 144
<211> LENGTH: 1080
<212> TYPE: DNA
<213> ORGANISM: Neurospora crassa

<400> SEQUENCE: 144
```

```
atgccgtcaa agctagccat tagttccatg tccctagggc gctgctttgc cggccactct     60
ctggacagca agcttgatgc cgctcaacga tacggctatc ttggtatcga gcttttttat   120
gaggatctgg tcgacgttgc agagcatttg tcgaacgagc gtccctctcc cgaaggccct   180
tttgtcgaag ctcagatagc cgccgctcgt catattctcc agatgtgtca agccagggcg   240
cttgaggtcg tctgcctcca gcctttcatg cactacgacg gccttaacga cagggcagaa   300
catgagcgtc gtctggagaa gctagcacta tggattgagc tcgctcatga gcttcacacc   360
gacatcattc agatcccagc caacttcctc cctgccaacc aagtcagtga caacctcgac   420
ctgattgtct cagatctttg caaggtggcc gatattggag ctcaagcttt gcccctatc    480 cgctttgcct acgagagtct tgctggagca cccgtgtcg acctctggga gcgctgctgg    540
gacatcgtac aacgcgttga ccgccccaac tttggcattt gccttgacac cttcaacatc   600
ctcggccgca tctatgccga ccctacatct cctagcggta ggacatccaa cgcaaaagag   660
gcagtcagga agtccatcgc caacttggtc tcgcgcgtgg atgtctccaa agtcttctac   720
gtccaggtgg ttgacgccga gaggctgagc aagccactac tgcccggtca cccgtattac   780
aatccagagc agccggcgag gatgagctgg tcgcgcaatt gtagactgtt ctacggcgaa   840
acagaatatg gtgcgtatct tcccgtgaag gaggttgctc gagccctttt tcacggcatt   900
ggtttcgagg ctgggtcag tttggagctt ttcaaccgca gaatgtctga ggagggacct   960
gaagtgccgg aggaacttgc catgagaggc gctatctcgt gggccaagtt ggtgcaagac  1020
ctgaggatac cggtggaggg gccattggtg acgatgcccc gagtctctgc ttcattgtaa  1080
```

```
<210> SEQ ID NO 145
<211> LENGTH: 1116
<212> TYPE: DNA
<213> ORGANISM: Aspergillus niger

<400> SEQUENCE: 145
```

```
atgcccaacc gtctcggcat cgcctccatg tcccttggac gcccaggcat ccactccctc     60
ccctggaagc tccacgaagc cgcccgccac ggctacagcg ggatcgagct cttcttcgac   120
gacctggacc actacgcaac cacccacttc aatggcagcc atcgcggc tgctcacgcc    180 gtgcacgctc tctgcacgac cctcaacctc accatcatct gcctgcaacc cttctccttc   240
tacgaggggc tcgtcgaccg caagcaaacc gagtatctat tgaccgtgaa gctgcccaca   300
tggttccagc tcgctcgcat cctcgacacc gacatgatcc aggtgccctc gaacttcgcg   360
cccgcccagc aaaccacggg tgaccgggac gtgatcgtcg gcgacctcca gcgcctcgca   420
gacatcggcc tggcacagtc cccgcccttc cgcttcgtat acgaagcact ggcctggggc   480
acgcgggtga acctgtggga cgaggcgtac gagatcgtcg aggccgtgga ccgtcccaac   540
ttcggtatct gtcttgatac gtttaacctt gcgggtcggg tgtatgcgca ccctggtcgg   600
caggacggga agacggtcaa cgcggaggcg gatctggctg cgtcgttgaa gaagttgcgc   660
gagacggtgg atgtcaagaa ggtgttctac gtgcaggttg tggatggaga gaggctggag   720
```

| aggccgttgg atgagaccca tccgtttcat gtggaggggc agccggtgcg atgaactgg | 780 |
| agtcgcaatg cgaggttgtt tgcgtttgag gaggatcgcg cgggtatttt gcccattgag | 840 |
| gagaccgcga gggcgttctt tgatacgggg ttcgagggct gggtgtcgtt ggagttgttt | 900 |
| agtcgcacgt tggcggagaa gggcacgggg gtggtcacgg agcatgcgag acgcggggttg | 960 |
| gagtcgtgga aggagttgtg taggaggttg gagtttaagg gggcggagcc gggactggat | 1020 |
| tttgttcctg gggaggtgaa ggtgcagtcg gttgctgtgg ggagtgggaa gggggtggaa | 1080 |
| caggaggaga tgggggttgt gcagcatcgg ttgtag | 1116 |

<210> SEQ ID NO 146
<211> LENGTH: 834
<212> TYPE: DNA
<213> ORGANISM: Mycobacterium smegmatis

<400> SEQUENCE: 146

| atgagtgccg agaggcgact gtcgctgaac accatgacca ccaagcgcct cacgctgcgc | 60 |
| gaggccgtcg aggcaaccgc cgcggccggg ctggagtcca tcggcctgtg gcgtgaccgc | 120 |
| gtagccgaag cgggtgtgga caccgccgcg aaactgatgc acgacaacgg tcttcgcgtg | 180 |
| tccagtctgt gccggggcgg tttcctgacc gggttcgagg aagaccatgc gctcgccgac | 240 |
| aaccggcgcg ccatcgagga ggcggtcacg ctcgggacgc gagagctcgt catggtcgtg | 300 |
| ggcggcatcc cggaccgtga cctcgccgcc gcgagggggac gtgtggctca gcggctcgag | 360 |
| acgctcgtgc cctacgccgt cgaccacggt gtccggctgg cgctggaacc gctgcacccg | 420 |
| gtgttctgcg ccgaccgcgc ggtgatctcc acactggggc aggcgctggc actcgcggcg | 480 |
| ccgtacccgg ccgaggccgt cggcgtcgtc gtcgacacct ccacgtgtg gtgggatccc | 540 |
| gagttggcgg acggcatcgc cgcggcgggc gctcagcacc ggatcagctc gtaccaggtg | 600 |
| tgcgactggc tggtcccgat ggccgccgac ccgctggtgt cgcgcggcat gatgggtgac | 660 |
| ggcgtcatcg acttcggtgc ggtcaccgcg atggtgcggg ccgcgggata cgacggcgac | 720 |
| gtcgaggtcg agatcttcaa cgaggacatc tgggccaccg acgcggccgt cgtcatcgac | 780 |
| accatgaaac agcgctaccg cgatctggtg gcgcctgctc tcacggcagg ctga | 834 |

<210> SEQ ID NO 147
<211> LENGTH: 1875
<212> TYPE: DNA
<213> ORGANISM: Corynebacterium halotolerans

<400> SEQUENCE: 147

| atgcgtacct cgatcgccac cgtctgcttg tccggcaccc tcgcggagaa gctccgggcg | 60 |
| gcggccgacg ccggattcga cggcgtggag atcttcgagc aggatctcac cgtctccccg | 120 |
| cactctccgg agcagatccg gcggcgcgcc gccgacctgg gcctcaccct cgatctcttc | 180 |
| cagcccttcc gtgacttcga gggggtggag gaagcgcagt cgaggcgaa cctgcgccgc | 240 |
| atggaggcga agttcgcgtt gatgaaccgc ctgggcatcg acaccatcct gctgtgctcg | 300 |
| aacgtcgcca ccgccaccat cgacgacgac gggctcttcg ccgcccagct gcgccgcgcc | 360 |
| ggtgaactgg ccgagcgtta cgacgtgcgc atcgcctatg aggcgctggc ctggggccgc | 420 |
| ttcgtcaacg acttcgagca cgcccgacgc atcgtcgacc tggccggcca cccgcgggtg | 480 |
| ggcacctgcc tggacacctt ccacatcctc tcccgcggct ggtccaccga cgcggtggag | 540 |
| gagatcgcgg gcgagaagat cttcttcgtc cagctcgccg acgcccgca gctgagcatg | 600 |

```
gacatcctgt cctggtcgcg ccaccaccgc gtcttcccg gcgaggggga cttcgacctg      660
gtgaagttca tgcgccacct cgcgcgcacc ggctacgacg gtccggtctc gctggagatc     720
ttcaacgact ccttccgcaa ggccgaggtc ggacgcaccg ccgtcgacgg cctgcgttcc     780
ctgcggtggc tggaggacca gacctggcgc gccctgcacg ccgcggggga gggcaaggcc     840
gctgaagccc tggagctgtc cccgctgccc gaggtcgccg accccgaggg cgtggacttc     900
gtggagatct ccaccggccg actgggggag accatcaagg tgctccacca gctcggcttc     960
cgcctcggcg ggtaccaccg cagcaagccc cagttccagg tgtggaccca ggggccggtg    1020
cgcgtcgtca tcggcgaccg cggggccgacc ggggcccccca ccggcatcac ctccctgggc   1080
gtgcggaccc cggaccccggc cgccgcgcag gcccgtgccc acctgctcca ggcccgtccg    1140 gtccccccgcg aacgggccgc gggcgaggtc gagctgcacg gggtgtacgc acccgacggc    1200
accgaagtgt tcttcagcgg tctggccccc gagaccgccc cggcgtggct ggcggaattc     1260
ggcgtcacgg acaacgacct ggagcccgcc ccgctgatca ccggcatcga ccacgtcaat     1320
ctggcccagc cctggcagca ctatgacgag accgtgctgt tctacacctc cctcatggcg    1380
ctggagaccc acagccgcga ggagttcccc agcccatcg ggctgatcag caataaggtc      1440
atgcgttcgg ccaacgacac cgtgcggtta ctgctcagcg tcgcccccga ggacggtgag     1500
cagggtgact tcctggccgc cgcctacccg gagcacatcg ccatcaccac caccgacatc    1560
gtcgcagtgg cgcgtcgtgc gcgacagcgg ggactggcgt tcctgccggt ccccgagaac    1620
tactacgacg acctgcaggc gagattcgac ctgaccccgg ccttcctcgc cgaactgcgc    1680
gagaacgacc tgctctacga ccgcgacgcc gacggcgaat tcctgcactt ctacaccggc    1740
accctgggca cgatgttcat cgaggtcgtc gagcgccgcg gcggtttctc cggctggggc    1800
gagaacaacg cccccggtccg actcgccgcc cagtaccgca acgtgcgcga cgccgaacgc    1860
ggcattccgc agtag                                                    1875
```

<210> SEQ ID NO 148
<211> LENGTH: 1935
<212> TYPE: DNA
<213> ORGANISM: Rhodococcus opacus

<400> SEQUENCE: 148

```
atgggacgac aggttcgtac gagcgttgcc acggtatccc tgagcggatc gctggaggag      60
aaggttaccg cgatcgcggc ggccgggttc gacggattcg aggtgttcga acccgatttc    120
gtgagctcgc cgtggtcgcc gcgtgagctg gcttcccgcg cagcggatct cggactcaca     180
ctcgatctgt atcagccgtt ccgcgatctg gactccgtgg acgacacgac gttcgcgcgc    240
aacctgatcc gagccgagcg caagttcgac atcatggagc agctcggctg cgacacccctg   300 ctggtgtgct cgtcgccgtt gcccgaggcg gtgcgggacg acgctcgcct gaccgagcaa    360
ctccacactc tcgccgagcg cgcacacagc cggggtctcc gcatcgccta cgaggcgctg    420
gcctggggca cgcacgtcaa cacgtaccgg cacgcgtgga agatcgtgca ggacgcggac    480
catcctgccc tcggtacctg cctcgacagc ttccacatcc tctcccgcgg cgacgacccg    540
tccggcatcc gcgacatccc cggggagaag atcttcttcc tccaactcgc cgacgcgccc    600
cgcatgtcga tggacatcct gcagtggagc cggcaccacc ggaacttccc ggggcagggc    660
aacttcgatc tcgcgacgtt cggcgcgcac gtccaggccg ctggatacac cggaccgtgg    720
tcgctcgaga tcttcaacga cacgttccgg cagtcgtcca cggggcgcac ggccgccgac    780
gcgcaccgct cgctgctgta cctccaggag gaggtcgcac gcgtgcaggc cgagcgcggt    840
```

```
gaggacaccg gtcgcggcct gacgctgttc gagccgccgc cgcgcgcacc cctcgaaggc      900
atcgtgtcgc tccggctcgc ggccggtccg ggcaaggatt ccgaccttcg gcaggcgctg      960
cagcacatcg gattccgtct ggtgggccgg caccgcagcc acgacctcca gttgtggcgg     1020
cacggccgga tgaccatcgt ggtcgatgcg accgcgggca cggtgtggac cgctccgggt     1080
ctgcctgcgc acctgccggt gctcacccag atcggtatcc ggtcgagcga tcccgacgcg     1140
tggggtgagc gcgccgcggc gctcgaggtc cggtgcacg aggtcctgtt gcccggtgtc      1200
gacaccgcac ccgaatcgga tgtggtgcgt ctcaagatca ccgacgcgac gtcgctggat     1260
ctgcgcggcc cgggcagcgc cgcgtcgtgg cagtcggcgt tcgatctgta tccgacggag     1320
tcgcgctggc aggatgaggt gcccgtcttc accggtgtcg atcacgtggc gctcgccgtg     1380
ccgtccgaca actgggacgg catcatgctg ctgctccgtt cggtgttcgc gatggcgccg     1440
cacgagggcc tcgatgtcac cgacgcggtc ggaatgatgc gcagtcaggc gctgacgatg     1500
gatcagacgg gtgcggacgg cgtcgaccgt ccgctgcgca tctccctgaa catggttccg     1560
ggtgcggtgt cgggcaactc ccacatcgcc gcggctcggc gcggcggcat cagtcacgtc     1620
gcgttctcgt gcacggacat tttcaccgcc gccgcgacca tgcagtccaa cgggttcgag     1680
ccccttgtga tttcgccgaa ctactacgac gacctcgagg cccgcttcgg gctctcccgc     1740
gaactcctgg accggatgag cgggtcgggc atcatgtacg accgtgatgc gcacggcgag     1800
ttcttccatc tgttcaccca gacggtgggc gccgacctgt tcttcgaggt ggtgcaacgc     1860
gtcggcggtt acgagggata cggggacgcg aactccgcga tgcgtttggc ggcccagttg     1920
cgggcggctg gctga                                                     1935

<210> SEQ ID NO 149
<211> LENGTH: 1101
<212> TYPE: DNA
<213> ORGANISM: Aspergillus oryzae

<400> SEQUENCE: 149
atgcctaacc gtctcggaat tggttccatg tccctggggc gcccgggaat ccacgatctg       60
ccaaccaagc tgcaccaggc ctctcagttc ggctacaagg gcatcgagct attctttgac      120
gaccttgacc acttggccaa gttgctcttt gatggagatc atattttagc tgctcatcat      180
gtacgccagc tttgtgtttc gctgggcctc tctatcatct gtctgcagcc cttttggcac      240
tacgaggggc ttctggatcg cactgagcac gagcgtcttc tcactgaaaa gcttcccaag      300
tggtttgagc ttgcacgcat tctggataca gatctcatcc agatcccatc taactttctc      360
cccgccgatg ctcagacagg ccagccccgc accacaggtg acatgtctgt cattgtctca      420
gatcttcaga agatcgccga tcttggcctt cagcagtctc cccccttttcg ttttgtctac     480 gaagccctag catggggtaa ccacatcaac aaatgggaag actcctggga agttgtagag      540
cgggtcaacc gtccaaactt tggaatttgt cttgacacct tcaatatcgc tggacgggtg      600
tatgccgatc ccacatctcc cacaggaaag acgcctaatg cggaagccga cctccaggca      660
tctatcgccc gcctgcgaac tcgcatcgac ctctcaaagg ttttctatgt tcaaatcgtg      720
gatggcgaac gcctgagtac ccctctggac gaatctcacc cattctatgt caagggtcag      780
ccctcccgca tgaactggtc gcgtaacgca cgcctgtttg cctttgaaga ggaccgtggt      840
ggatacttac ccgtcttgga cgtcgctaaa gccttcttcg atattggctt cgagggctgg      900
gtttccctgg aattgttcaa cagaagcttg gctgatcctg acccatctac gcctcgcaat      960
```

| | |
|---|---|
| catgccaaaa gagggtttga gtcttggaag aaactggtcg ctgccttgaa gctcaatacc | 1020 |
| ggtgatgctt ctatggtgca tggtcttgac ggtacaattt caccatcgac ttctgctttg | 1080 |
| cctgtgcagc atcgccttta g | 1101 |

<210> SEQ ID NO 150
<211> LENGTH: 843
<212> TYPE: DNA
<213> ORGANISM: Bacillus thuringiensis

<400> SEQUENCE: 150

| | |
|---|---|
| atgaaatatt cgctatgtac catttcattt cgtcatcaat taatttcatt tactgatatt | 60 |
| gttcaatttg catatgaaaa cggttttgaa ggaattgaat tgtgggggac tcatgcacaa | 120 |
| aatttgtata tacaagaacg cgaaacgaca gaacgagaat tgacttttct aaaggataaa | 180 |
| aacttagaaa ttacgatgat aagtgattac ttagatatat cattatcagc agattttgaa | 240 |
| aaaacgatag agaaaagtga acaacttgta gtactagcta attggtttaa tacgaataaa | 300 |
| attcgcacgt ttgctgggca aaaagggagc aaggacttct cggaacaaga gagaaaagag | 360 |
| tatgtaaagc gaatacgtaa gatttgtgat gtgtttgctc agcacaatat gtatgtgctg | 420 |
| ttagaaacac atcccaatac actaacagac acattgcctt ctactataga actattagaa | 480 |
| gaagtaaatc atccgaattt aaaaataaat cttgattttc tccatatatg ggagtctggc | 540 |
| gcagatccaa tagacagttt ccatcgatta aagccgtgga cactacatta ccattttaag | 600 |
| aatatatctt cagcggatta tttgcatgtg tttgaaccta ataatgtata tgctgcagca | 660 |
| ggaagtcgta ttggtatggt tccgttattt gaaggtattg taaattatga tgagattatt | 720 |
| caggaagtga gaggtacgga tcttttttgct tccttagaat ggtttggaca taatgcaaaa | 780 |
| gagatattaa agaagaaat gaaagtatta ataaatagaa aattagaagt agtaacttcg | 840 |
| taa | 843 |

<210> SEQ ID NO 151
<211> LENGTH: 2094
<212> TYPE: DNA
<213> ORGANISM: Corynebacterium glutamicum

<400> SEQUENCE: 151

| | |
|---|---|
| ttgacgctgt cacctgaact tcaggcgctc actgtacgca attaccctc tgattggtcc | 60 |
| gatgtggaca ccaaggctgt agacactgtt cgtgtcctcg ctgcagacgc tgtagaaaac | 120 |
| tgtggctccg gccacccagg caccgcaatg agcctggctc ccttgcata cccttgtac | 180 |
| cagcgggtta tgaacgtaga tccacaggac accaactggg caggccgtga ccgcttcgtt | 240 |
| cttctttgtg gccactcctc tttgacccag tacatccagc tttacttggg tggattcggc | 300 |
| cttgagatgg atgacctgaa ggctctgcgc acctgggatt ccttgacccc aggacaccct | 360 |
| gagtaccgcc acaccaaggg cgttgagatc accactggcc ctcttggcca gggtcttgca | 420 |
| tctgcagttg gtatggccat ggctgctcgt cgtgagcgtg gctattcga cccaaccgct | 480 |
| gctgagggcg aatccccatt cgaccaccac atctacgtca ttgcttctga tggtgacctg | 540 |
| caggaaggtc tcacctctga ggcatcctcc atcgctggca cccagcagct gggcaacatc | 600 |
| atcgtgttct gggatgacaa ccgcatctcc atcgaagaca cactgagat cgctttcaac | 660 |
| gaggacgttg ttgctcgtta caaggcttac ggctggcaga ccattgaggt tgaggctggc | 720 |
| gaggacgttg cagcaatcga agctgcagtg gctgaggcta agaaggacac caagcgacct | 780 |
| accttcatcc gcgttcgcac catcatcggc ttcccagctc caaccatgat gaacaccggt | 840 |

```
gctgtgcacg gtgctgctct tggcgcagct gaggttgcag caaccaagac tgagcttgga    900
ttcgatcctg aggctcactt cgcgatcgac gacgaggtca tcgctcacac ccgctccctc    960
gcagagcgcg ctgcagagaa gaaggctgca tggcaggtca agttcgatga gtgggcagct   1020
gccaaccctg agaacaaggc tctgttcgat cgcctgaact cccgtgagct ccagcgggc    1080 tacgctgacg agctcccaac atgggatgca gatgagaagg cgtcgcaac  tcgtaaggcg   1140 tccgaggctg cacttcaggc actgggcaag accttcctg agctgtgggg cggttccgct   1200
gacctcgcag gttccaacaa caccgtgatc aagggctccc cttccttcgg ccctgagtcc   1260
atctccaccg agacctggtc tgctgagcct acggccgta acctgcactt cggtatccgt    1320
gagcacgcta tgggatccat cctcaacggc atttccctcc acggtggcac ccgcccatac   1380
ggcggaacct tcctcatctt ctccgactac atgcgtcctg cagttcgtct tgcagctctc   1440
atggagaccg acgcttacta cgtctggacc cacgactcca tcggtctggg cgaagatggc   1500
ccaacccacc agcctgttga aaccttggct gcactgcgcg ccatcccagg tctgtccgtc   1560
ctgcgtcctg cagatgcgaa tgagaccgcc caggcttggg ctgcagcact tgagtacaat   1620
gaaggcccta agggtcttgc actgacccgc cagaacgttc ctgttctgga aggcaccaag   1680
gagaaggctg ctgaaggcgt tcgccgcggt ggctacgtcc tggttgaggg ttccaaggaa   1740
accccagatg tgatcctcat gggctccggc tccgaggttc agcttgcagt taacgctgcg   1800
aaggctctgg aagctgaggg cgttgcagct cgcgttgttt ccgttccttg catggattgg   1860
ttccaggagc aggacgcaga gtacatcgag tccgttctgc ctgcagctgt gaccgctcgt   1920
gtgtctgttg aagctggcat cgcaatgcct tggtaccgct tcttgggcac ccagggccgt   1980
gctgtctccc ttgagcactt cggtgcttct gcggattacc agaccctgtt tgagaagttc   2040
ggcatcacca ccgatgcagt cgtggcagcg gccaaggact ccattaacgg ttaa         2094

<210> SEQ ID NO 152
<211> LENGTH: 1083
<212> TYPE: DNA
<213> ORGANISM: Corynebacterium glutamicum

<400> SEQUENCE: 152
atgtctcaca ttgatgatct ggcacagctc ggcacttcca cttggctcga cgacctctcc     60
cgcgagcgca ttacttccgg caatctcagc caggttattg aggaaaagtc tgtagtcggt    120
gtcaccacca acccagctat tttcgcagca gcaatgtcca agggcgattc ctacgacgct    180
cagatcgcag agctcaaggc cgctggcgca tctgttgacc aggctgttta cgccatgagc    240
atcgacgacg ttcgcaatgc ttgtgatctg tttaccggca tcttcgagtc ctccaacggc    300
tacgacggcc gcgtgtccat cgaggttgac ccacgtatct ctgcggaccg cgacgcaacc    360
ctggctcagg ccaaggagct gtgggcaaag gttgatcgtc aaacgtcat gatcaagatc     420 cctgctaccc aggttctttt gccagcaatc accgacgctt ggctgagggc atcagtgtt    480 aacgtcacct tgatcttctc cgttgctcgc taccgcgaag tcatcgctgc gttcatcgag   540
ggcatcaagc aggcagctgc aaacggccac gacgtatcca agatccactc tgtggcttcc   600
ttcttcgtct cccgcgtcga cgttgagatc gacaagcgcc tcgaggcaat cggatccgat   660
gaggctttgg ctctgcgtgg caaggcaggc gttgccaacg ctcagcgcgc ttacgctgtg   720
tacaaggagc ttttcgacgc cgccgagctg cctgaaggcg ccaacactca gcgcccactg   780
tgggcatcca ccggcgtgaa gaaccctgcg tacgctgcaa ctctttacgt ttccgagctg   840
```

```
gctggtccaa acaccgtcaa caccatgcca gaaggcacca tcgacgctgt tctggaactg      900
ggcaacctgc acggtgacac cctgtccaac tccgcggcag aagctgacgc tgtgttctcc      960
cagcttgagg ctctgggcgt tgacttggca gatgtcttcc aggtcctgga gaccgagggc     1020
gtggacaagt tcgttgcttc ttggagcgaa ctgcttgagt ccatggaagc tcgcctgaag     1080
tag                                                                   1083

<210> SEQ ID NO 153
<211> LENGTH: 1098
<212> TYPE: DNA
<213> ORGANISM: Corynebacterium glutamicum

<400> SEQUENCE: 153
atgagcgcag cgcagatttt caacaccgtc cacgtcaatg gatcttcccc ctatgatgtc       60
cacattggtt ccggcctcaa cgagctcatt gttcagcgcg cagcggaatc aggcgcggag      120
caggtagcga ttttgcacca gcccagcatg gatgacattg catccgagtt ggatgcagca      180
ctagtcgctg ctggtttgaa ggtcctgcac cttaatgttc ccgatgcgga aaacggcaag      240
tccttggaag tagcggggca gtgctgggat gaattgggtg gcgcagcatt cggccgccgc      300
gatatcgtca tcggacttgg tggcggtgct gccacagatc tcgcgggatt cgtcgctgct      360
gcgtggatgc gtggcgtgcg cgtcattcag gttccaacca ccttgttggc catggtggac      420
gctgcggtgg gcggcaagac tggcatcaat accgccgcag gcaagaacct tgtgggcgcg      480
ttccacgagc ctgacgcagt attcattgac accgaacgcc tagccaccct gcctgacgcg      540
gaaatcatcg cgggatccgc cgaaatcatc aaaactggtt tcatcgccga cccagaaatc      600
ctgcgccttt acgaaactga tcccgcagcc tgcctgaaga agaagtcga aggctcccac      660 ctacctgaac tgatttggcg ctccgtcacc gtcaagggct ccgtggtcgg ccaagacctc      720
aaagaatcta gcctgcgcga atcctcaac tacggacaca cctttgccca cgccgtcgaa      780
ctccgcgaaa acttccgctg gcgccacggc aatgccgttg cagtgggcat gatgttcatc      840
gctaacctct cccacaagct cgggcttatc gacgcgcccc tcctcgagcg ccaccgctca      900
atcctggcgg ccatcggtct gcccacttcc tacgaaggcg gagccttcga cgagctttac      960
gacggcatga cccgcgacaa gaaaaaccgc gacggcaaca tccgcttcgt cgcactgacc     1020
gccgtgggcg aggttacccg cattgagggg ccctcaaaac aagatttaca gagtgcttat     1080
gaggcaatca gccactaa                                                   1098

<210> SEQ ID NO 154
<211> LENGTH: 573
<212> TYPE: DNA
<213> ORGANISM: Corynebacterium glutamicum

<400> SEQUENCE: 154
atggagcgta atgaagtgaa tgatcaaatt cacttagatc atcaatcaga tgacacctct       60
gaatgctcct gcccgatcgt ggttcttgtg ggtttgccag gagctggaaa atccaccatt      120
ggacgtcgat tagcgcgcgc cttaaacact gaactcgtcg actccgacga actcattgag      180
cgcgccaccg gaaaagcctg cggcgccgtg ttcagcgagc tcggcgagcc agccttccgc      240
gagctcgagg ccatccacgt ggccgaagca ctgaaatcct ccggagtggt gagcttggga      300
ggcggatctg tgctgacaga atccaccgt gaactgctca aaggccacga cgtggtctgg      360
atcgacgtgc cagtagaaga aggcatcagg cgcaccgcaa cgagcgttc ccgcccgtg       420 ctgcaagccg ccgaccccgc cgagcactac cgcaacctgg tgaaagtgcg caccccgttg      480
```

| | |
|---|---|
| tacgaagagg tggcaaccta ccgacttcgc accaacaacc gcagccccca gcaagtggtg | 540 |
| gcagcagtgt tgcatcatct agaaatcgat taa | 573 |

<210> SEQ ID NO 155
<211> LENGTH: 1293
<212> TYPE: DNA
<213> ORGANISM: Corynebacterium glutamicum

<400> SEQUENCE: 155

| | |
|---|---|
| atggtctttg tgtctgattc gtctatctct ttgcccattt gggatgctcc gcgcgctcgc | 60 |
| ggccccatag tctcggacct ggctatccct ggttccaagt cgatcaccaa ccgcgccctc | 120 |
| atcttggctg cgctcgcatc aactccatcc accatcattg atgtccttcg tagtcgtgat | 180 |
| accgatctca tgactgatgg tctacgcagc ctcggaatca ccattactga agaggcagtc | 240 |
| gatcgctacc gcgttgagcc cggacagttg tctgctggct ccgttgagtg tggtcttgct | 300 |
| ggtacggtca tgcgcttttt gcctcctgtt gctgctttcg ctgatggtcc tgttcatttt | 360 |
| gatggcgatc ctcaagctcg tgttcgtccg atgaccagca tttttggatgc gctgcgttcg | 420 |
| cttggtgtgg aggtggacaa caacaatctg cctttcactg ttaatgctgg tgaggtccct | 480 |
| gagggtggcg tggttgagat tgatgcttcc ggctcatctc agtttgtttc tggtcttttg | 540 |
| ctttcagcgc ctcgttttaa aaatggcgtc accgttaagc acgtcggtgg tcgtctgccg | 600 |
| agcatgccgc atattgagat gaccgtcgat atgcttcgtt ccgcaggcat tgagatcgaa | 660 |
| gagtcagaaa atcagtgggt tgttcatcct ggtgagatct gggtcggac ctggcgcatt | 720 |
| gagccggatc tttctaatgc gactccgttc ctagctgccg ctgcggtcac tggtggaacc | 780 |
| atcaagatta atcactggcc aatcaaaact actcagcctg gcgatgctat tcgttcgatt | 840 |
| cttgagcgca tgggctgcga agttgagctg gttgctcagg gtgaaggtta cgatctgtcg | 900 |
| gtgactggtc cggttgctct caagggcatt gagatcgata tgtccgatat cggtgagttg | 960 |
| accccctaccg tggcggcgtt ggctgcgttg gcgtcgacag agtctcgttt gaccggtatt | 1020 |
| gctcatcttc gtggccatga gacggatcgt ttggctgcgt tgactgcgga gatcaacaaa | 1080 |
| cttggtggaa agtgcactga gcttaaggat ggtctgttga ttgagcctgc gtcgctgcac | 1140 |
| ggtggtgtgt ggcattcata tgctgatcat cgtatggcta ctgctggtgc gatcattggc | 1200 |
| ctcgcggttg atgacgttca ggttgaagac attaagacca cttccaagac tttccctggt | 1260 |
| tttgaaaatg tttgggagga gatggttggc tag | 1293 |

<210> SEQ ID NO 156
<211> LENGTH: 1233
<212> TYPE: DNA
<213> ORGANISM: Corynebacterium glutamicum

<400> SEQUENCE: 156

| | |
|---|---|
| atgctaggca tgcttcgatg gactacagca ggtgaatccc acggccaggc gcttatcgcc | 60 |
| acggttgaac acatgccagc aggcgtgccc gtgactaaag atgaggtctc gtatcaattg | 120 |
| gcgcgccgac gccttggata tggtcgcggc gctcgcatga gtttgagca agacgcgttg | 180 |
| accttcctga ccggcatccg ccacggcctc actttgggta gccccatctc aatcatgatc | 240 |
| ggcaacactg agtgggataa gtggaccacc atcatgtcct ctgacgcttt ggacatggaa | 300 |
| gacccagaca acgttgcggc gatgtcttcg ggtcgcggtg caaaactgac tcgtccgcgt | 360 |
| ccaggccacg cagattacgc aggcatgctc aagtacggat tcgatgatgc ccgcaacgtg | 420 |

```
ctggagcgtt cttcagcccg tgagacggca gctcgcgtgg cagcagcaac cgttgcgcgt      480
tccttcctcc gtgaaacctt gggcgtggag gtgctctctc acgtaatttc cattggtgcg      540
tccgagcctt acgtcggcgc ggagccaacc tttgcagata ttcaagcaat cgatgattcc      600
ccagttcgtg cattcggtaa agacgctgaa aaatccatga tcgcgaaat cgaggccgca       660
```
(Note: line 660 as printed)
```
aagaaagccg gcgataccct cggtggcatc gtggaagtga ttgttgaagg cctacccatc      720
ggtttgggct cacacatttc tggcgaagat cgcctcgatg cgcagatcgc agctgcactc      780
atgggcattc aggccatcaa gggcgtggaa atcggtgacg gtttcgaaga agctcgtcga      840
cgtggctccg aagcccacga tgaagtgttc ctggatgaca acggcgtata ccgcaacacc      900
aaccgtgcag gtggcctcga aggcggcatg accaacggtg aaaccctgcg cgttcgtgct      960
ggcatgaagc caatttctac tgtgcctcgc gccctgaaaa ccattgatat ggaaaacggc     1020
aaggcagcaa ccggaatcca ccagcgttcc gacgtgtgcg ctgttccagc cgccggtgtc     1080
gttgcagaag caatggtcac cctggttctc gcccgcgcag tcctgcagaa attcggcggt     1140
gactccctga gtgaaaccaa gagcaacatt gacacctacc tcaaaaacat tgaggaacga     1200
atgaaattcg aaggtttaga ggatggagcg taa                                  1233
```

<210> SEQ ID NO 157
<211> LENGTH: 1476
<212> TYPE: DNA
<213> ORGANISM: Corynebacterium glutamicum

<400> SEQUENCE: 157

```
atggctagta ccttcattca ggccgacagc cctgaaaaaa gtaagaagct accccactc        60 acagaaggtc cgtatagaaa gcggctgttc tacgttgcac tagttgcgac gtttggtggg      120
ctgctcttcg gatatgacac cggagtaatc aacggtgcac tcaacccaat gacacgtgag      180
ctcggactaa ccgcgttcac cgagggtgtt gtaacttctt ccctgctgtt tggtgcagca      240
gctggtgcga tgttttcgg tcgcatttcc gacaactggg gtcgccggaa acaatcatc        300 tcacttgcag tagctttctt tgtcggcacc atgatctgcg tgtttgctcc atcttttgca      360
gtaatggttg tcggacgtgt gcttcttgga ctcgcagttg gtggcgcttc cactgttgtc      420
cctgtctacc tggctgaact tgctcctttt gaaatccgtg gctcactggc tggccgtaat      480
gagttgatga ttgttgttgg tcagctcgca gctttcgtca tcaatgcgat tattggaaat      540
gttttttgga ccacgcatgg tgtgtggcgc tacatgctgg caattgccgc aatcccagca      600
attgccctct tctttggaat gctccgagtt ccagaatccc cacgctggct tgttgagcga      660
ggacgcattg atgaggctcg cgcagttctt gaaaccattc gccctctaga acgtgcccat      720
gcagaagttg ctgatgttga gcacctagca aaagaagagc acgccatttc cgagaagtcc      780
atgggcttaa gggaaatttt gtccagcaag tggcttgtgc gcatcctcct ggtaggtatc      840
ggattgggtg tcgcacagca gctgactggc atcaactcca tcatgtacta cggccaggtt      900
gttctcattg aggctggttt ctccgaaaat gcagctctga tcgccaacgt ggcgccagga      960
gtgatcgcag ttgtcggtgc atttatcgca ctgtggatga tggatcgcat caaccgccgt     1020
accaccctca ttaccggcta ctctctcact accattagcc acgtgttgat cggcatcgca     1080
tccgtagcat tctcagtcgg cgatccactt cgcccatacg ttattttgac cctagttgtg     1140
atcttcgtag gatccatgca gaccttcctc aacgtagcca cctgggtcat gctctccgag     1200
ctcttcccgc tggcaatgcg aggtttcgca atcggtatct cagtgttctt cctctggatc     1260
gcaaacgcgt tcctcggatt gttcttcccc accatcatgg aagcagtagg actaaccgga     1320
```

```
accttcttca tgttcgccgg aatcggtgtg gttgccttga tcttcatcta cacccaggtt    1380
cctgaaactc gtggacgtac cttggaggag attgatgagg atgttacttc cggtgtcatt    1440
ttcaacaagg acatccgaaa aggaaaggtg cactaa                              1476
```

<210> SEQ ID NO 158
<211> LENGTH: 972
<212> TYPE: DNA
<213> ORGANISM: Corynebacterium glutamicum

<400> SEQUENCE: 158

```
atgccacaaa aaccggccag tttcgcggtg ggctttgaca tcggcggcac caacatgcga      60
gctgggcttg tcgacgaatc cgggcgcatc gtgaccagtt tgtcggcgcc gtcgccgcgc     120
acgacgcagg caatggaaca ggggattttt gatctagtcg aacagctcaa ggccgaatac     180
ccggttggtg ctgtgggact tgccgtcgcg ggattttgg atcctgagtg cgaggttgtt      240
cgatttgccc cgcaccttcc ttggcgcgat gagccagtgc gtgaaaagtt ggaaaacctt     300
ttgggcctgc ctgttcgttt ggaacatgat gccaactcag cagcgtgggg tgagcatcgt     360
tttggtgcag ctcaaggcgc tgacaactgg gttttgttgg cactcggcac tggaattggt     420
gcagcgctga ttgaaaaagg cgaaatttac cgtggtgcat atggcacggc accagaattt     480
ggtcatttgc gtgttgttcg tggcggacgc gcatgtgcgt gtggcaaaga aggctgcctg     540
gagcgttact gttccggtac tgccttggtt tacactgcgc gtgaattggc ttcgcatggc     600
tcattccgca acagcgggct gtttgacaag atcaaagccg atccgaattc catcaatgga     660
aaaacgatca ctgcggcagc gcgccaagaa gacccacttg ctctcgccgt tctggaagat     720
ttcagcgagt ggctgggcga aactttggcg atcattgctg atgtccttga cccaggtatg     780
atcatcattg gtggcggact gtccaatgct gccgaccttt atttggatcg ctcggttaac     840
cactattcca cccgcatcgt cggcgcagga tatcgccctt tggcacgcgt tgccacagct     900
cagttgggtg cggatgctgg catgatcggt gtcgctgatc tggctcgacg ttccgtgttg     960
gaagccaact ag                                                        972
```

<210> SEQ ID NO 159
<211> LENGTH: 912
<212> TYPE: DNA
<213> ORGANISM: Corynebacterium glutamicum

<400> SEQUENCE: 159

```
atgactgatc ccacttgcac ccttgccctt gatattggtg ccacaaagat tgcctacgca      60
ctagtccccg ataacgcccc gacgacaaca ttgtccacgg gacgctggga acaaaagaa      120 ggcgacagcc ctatcgagca gatccggctg gttcttctgg caggcttaaa agctgccgag     180
gaacacggtc tcagtgtcgc ccgcatcggc atgggcgctc tggtgtaat tctgggacca      240 gagggaacca tcgtgtacaa cggtgaaacc ctcacagagt gggcaggcac tgacctgcga     300
ggattatccc gagaagtcct caacgttcca ttcgcggcac acaatgatgt ccgcgtatgg     360
gcctacggtg agcaccactt aggcaccggc aaagacctca ccggcagggt tctctacgtg     420
tccctcggca ctggagtcgg cggagcaatc atcgaagacg aatcatgat gagtagcccc     480 actggaactg cggagaatt cgcagaagtt gtgtgctctg accatgcagg attagccgtt     540
cggtgcgaaa atgtagcaag tggcaccggc ctaaccaggt actacaacga ggccgccgca     600
actcaacttg accttcccgc catcatggag cgcttccacc aaggtgacgg cctggcacag     660
```

```
caaatcatta ctggaaatct ccgaggcttt ggccaagcgc taggcgcatt agtcacagtg      720
ctggaccttt ccgcagtagt agttggaggc ggagtcgcag gcatcggcgc acccgtcatg      780
gatcccatca ccgcagggat tttcgatcga atgttagccc ccaacaaatc cgtacaagtt      840
ttaagcacgt cccttggtgc ccaagcagcc gtcatcgcag cagcaaaata tgcccgcgat      900
aacgcctttt aa                                                         912

<210> SEQ ID NO 160
<211> LENGTH: 1233
<212> TYPE: DNA
<213> ORGANISM: Corynebacterium glutamicum

<400> SEQUENCE: 160
gtggcgcgcg gcggtgtaca gcaccccggt gaccacattg atcacagcac ctgctacgac       60
ctcgccgtcg atcgccgcag cgatcgagac ggcgtattgg ggcaggccat aaaggaagtt      120
gacggtgccg tcaatggggt cgacgatcca ggtaactccg cttatcgacg ccgtccccgt      180
cccttcctcg cctatcagcc cgtctttagg ccgaagttcc tgcaacctat tggcgataaa      240
atcttcagcc aaagtatcta ctatcgtcac cggatcgact gtcgaacttt tggtgttggt      300
gtagtcccac aaattggtga gttcagcacg tttatccctg atacgtgtag cggtaagcgt      360
ggcagtttcc gcggcgatgg cacgcaactc attaaacgat tgttgttcca taagaccatc      420
atcgttgttt ttttagaaaa ttgcctgcca aaagccgaag taatttgtac acttgggcgc      480
atgactgaga ctggatttgg aattgatatc ggtggctccg gcatcaaagg cgcccgcgtt      540
aaccttaaga ccggtgagtt tattgatgaa cgcataaaaa tcgccacccc taagccagca      600
accccagagg ctgtcgccga agtagtcgca gagattattt ctcaagccga atgggagggt      660
ccggtcggaa ttaccctgcc gtctgtcgtt cgcgggcaga tcgcgctatc cgcagccaac      720
attgacaagt cctggatcgg caccgatgtg cacgaacttt ttgaccgcca cctaaatggc      780
cgagagatca ccgttctcaa tgacgcagac gccgccggca tcgccgaagc aacctttggc      840
aacgctgccg cacgcgaagg cgcagtcatc ctgctgaccc ttggtacagg tattggatcc      900
gcattccttg tggatggcca actgttcccc aacacagaac tcggtcacat gatcgttgac      960
ggcgaggaag cagaacacct tgcagcagca gccgtcaaag aaaacgaaga tctgtcatgg     1020
aagaaatggg cgaagcgcct gaacaaggtg ctgagcgaat acgagaaact tttctccccca    1080 tccgtcttca tcatcggtgg cggaatttcc agaaagcacg aaaagtggct tccattgctg     1140
gagctagaca ctgacattgt cccagctgag ctgcgcaatc gagccggaat cgtaggagct     1200
gccatggcag taaaccaaca cctcaccccca taa                                 1233

<210> SEQ ID NO 161
<211> LENGTH: 1005
<212> TYPE: DNA
<213> ORGANISM: Corynebacterium glutamicum

<400> SEQUENCE: 161
atgaccattc gtgttggtat taacggattt ggccgtatcg gacgtaactt cttccgcgca       60
gttctggagc gcagcgacga tctcgaggta gttgcagtca acgacctcac cgacaacaag      120 acccttttcca cccttctcaa gttcgactcc atcatgggcc gccttggcca ggaagttgaa      180
tacgacgatg actccatcac cgttggtggc aagcgcatcg ctgtttacgc agagcgcgat      240
ccaaagaacc tggactgggc tgcacacaac gttgacatcg tgatcgagtc caccggcttc      300
ttcaccgatg caaacgcggc taaggctcac atcgaagcag gtgccaagaa ggtcatcatc      360
```

-continued

```
tccgcaccag caagcaacga agacgcaacc ttcgtttacg gtgtgaacca cgagtcctac      420
gatcctgaga accacaacgt gatctccggc gcatcttgca ccaccaactg cctcgcacca      480
atggcaaagg tcctgaacga caagttcggc atcgagaacg gcctcatgac caccgttcac      540
gcatacaccg gcgaccagcg cctgcacgat gcacctcacg gcgacctgcg tcgtgcacgt      600
gcagcagcag tcaacatcgt tcctacctcc accggtgcag ctaaggctgt tgctctggtt      660
ctcccagagc tcaagggcaa gcttgacggc tacgcacttc gcgttccagt tatcaccggt      720
tccgcaaccg acctgacctt caacaccaag tctgaggtca ccgttgagtc catcaacgct      780
gcaatcaagg aagctgcagt cggcgagttc ggcgagaccc tggcttactc cgaagagcca      840
ctggtttcca ccgacatcgt ccacgattcc cacggctcca tcttcgacgc tggcctgacc      900
aaggtctccg gcaacaccgt caaggttgtt tcctggtacg acaacgagtg gggctacacc      960
tgccagctcc tgcgtctgac cgagctcgta gcttccaagc tctaa                    1005
```

<210> SEQ ID NO 162
<211> LENGTH: 1053
<212> TYPE: DNA
<213> ORGANISM: Escherichia coli

<400> SEQUENCE: 162

```
atgaattatc agaacgacga tttacgcatc aaagaaatca agagttact tcctcctgtc       60 gcattgctgg aaaaattccc cgctactgaa aatgccgcga atacggttgc ccatgcccga     120
aaagcgatcc ataagatcct gaaaggtaat gatgatcgcc tgttggttgt gattggccca     180
tgctcaattc atgatcctgt cgcggcaaaa gagtatgcca ctcgcttgct ggcgctgcgt     240
gaagagctga aagatgagct ggaaatcgta atgcgcgtct attttgaaaa gccgcgtacc     300
acggtgggct ggaaagggct gattaacgat ccgcatatgg ataatagctt ccagatcaac     360
gacggtctgc gtatagcccg taaattgctg cttgatatta cgacagcgg tctgccagcg     420 gcaggtgagt ttctcgatat gatcaccca caatatctcg ctgacctgat gagctggggc     480
gcaattggcg cacgtaccac cgaatcgcag gtgcaccgcg aactggcatc agggctttct     540
tgtccggtcg gcttcaaaaa tggcaccgac ggtacgatta aagtggctat cgatgccatt     600
aatgccgccg gtgcgccgca ctgcttcctg tccgtaacga aatgggggca ttcggcgatt     660
gtgaatacca gcgtaacgg cgattgccat atcattctgc gcggcggtaa agagcctaac     720
tacagcgcga agcacgttgc tgaagtgaaa gaagggctga acaaagcagg cctgccagca     780
caggtgatga tcgatttcag ccatgctaac tcgtccaaac aattcaaaaa gcagatggat     840
gtttgtgctg acgtttgcca gcagattgcc ggtggcgaaa aggccattat tggcgtgatg     900
gtggaaagcc atctggtgga aggcaatcag agcctcgaga gcggggagcc gctgcctac     960 ggtaagagca tcaccgatgc ctgcatcggc tgggaagata ccgatgctct gttacgtcaa    1020
ctggcgaatg cagtaaaagc gcgtcgcggg taa                                 1053
```